United States Patent
Mandal et al.

(10) Patent No.: US 9,927,550 B2
(45) Date of Patent: Mar. 27, 2018

(54) METHOD AND SYSTEM FOR APPLYING NQR PULSE SEQUENCES

(71) Applicant: SCHLUMBERGER TECHNOLOGY CORPORATION, Sugar Land, TX (US)

(72) Inventors: Soumyajit Mandal, Cambridge, MA (US); Yi-Qiao Song, Newton Center, MA (US)

(73) Assignee: SCHLUMBERGER TECHNOLOGY CORPORATION, Sugar Land, TX (US)

( * ) Notice: Subject to any disclaimer, the term of this patent is extended or adjusted under 35 U.S.C. 154(b) by 670 days.

(21) Appl. No.: 14/383,886

(22) PCT Filed: Mar. 7, 2013

(86) PCT No.: PCT/US2013/029533
§ 371 (c)(1),
(2) Date: Sep. 8, 2014

(87) PCT Pub. No.: WO2013/134474
PCT Pub. Date: Sep. 12, 2013

(65) Prior Publication Data
US 2015/0077102 A1    Mar. 19, 2015

Related U.S. Application Data

(60) Provisional application No. 61/608,462, filed on Mar. 8, 2012.

(51) Int. Cl.
*G01V 3/32* (2006.01)
*G01N 24/08* (2006.01)
*G01R 33/44* (2006.01)
*G01V 3/14* (2006.01)

(52) U.S. Cl.
CPC ............ *G01V 3/32* (2013.01); *G01N 24/084* (2013.01); *G01N 24/087* (2013.01); *G01R 33/441* (2013.01); *G01V 3/14* (2013.01)

(58) Field of Classification Search
CPC .. G01N 24/084; G01N 24/087; G01R 33/441; G01V 3/14
See application file for complete search history.

(56) References Cited

U.S. PATENT DOCUMENTS

| | | | |
|---|---|---|---|
| 5,583,437 A | 12/1996 | Smith et al. | |
| 7,847,544 B2 | 12/2010 | Blanz et al. | |
| 9,476,953 B1* | 10/2016 | Zank | G01N 24/084 |

(Continued)

OTHER PUBLICATIONS

"Kerogen", Retrieved from the Internet: http://en.wikipedia.org/wiki/Kerogen, 2011, 5 pages.

(Continued)

*Primary Examiner* — Gregory H Curran

(57) ABSTRACT

A method and system for applying nuclear quadrupole resonance (NQR) sequences to a substance and determining presence of a chemical species within the substance using the sequences are described herein. The method includes applying an NQR pulse sequence to the substance using a non-resonant transmitter circuit. The method further includes detecting a NQR signal within the substance and determining presence of a chemical species within the substance using the NQR signal.

27 Claims, 25 Drawing Sheets

(56) References Cited

U.S. PATENT DOCUMENTS

2006/0273786 A1  12/2006  Smith et al.
2008/0309338 A1  12/2008  Cao et al.
2012/0001629 A1   1/2012  Hopper et al.
2013/0234705 A1   9/2013  Mandal et al.

OTHER PUBLICATIONS

Cantor, et al., "Pulsed spin locking in pure nuclear quadrupole resonance", the Journal of Chemical Physics, vol. 73, 1980, pp. 1054-1064.

Dehmelt, et al., "Nuclear Quadrupole Resonance", American Journal of Physics, vol. 22, No. 3, 1954, pp. 110-120.

Garroway, et al., "Remote sensing by nuclear quadrupole resonance", Geoscience and Remote Sensing, IEEE Transactions on vol. 39, Issue 6, Jun. 2001, pp. 1108-1118.

Lee, et al.,"Spin-1 nuclear quadrupole resonance theory with comparisons to nuclear magnetic resonance", Concepts in Magnetic Resonance, vol. 14, Issue 3, 2002, pp. 155-171.

Luznik, et al., "Zeeman shift—a tool for assignment of 14N NQR lines of nonequivalent 14N atoms in powder samples", Journal of Magnetic Resonance, vol. 212, No. 1, Sep. 2011, pp. 149-153.

Marino, et al., "Multiple spin echoes in pure quadrupole resonance", the Journal of Chemical Physics, vol. 67, 1977, pp. 3388-3340.

Ostroff, et al., "Multiple Spin Echoes and Spin Locking in Solids", Physical Review Letters, vol. 16, Jun. 13, 1966, pp. 1097-1099.

Pound, et al., "Nuclear Electric Quadrupole Interactions in Crystals", Physical Review Letters, vol. 79, No. 4, 1950, pp. 685-705.

Sauer, et al., "Spin dynamics in the pulsed spin locking of nuclear quadrupole resonance", Physical Review B, vol. 74, Nonvember 9, 2006, pp. 174410-11.

Slusher, et al., "Sensitive Detection of Nuclear Quadrupole Interactions in Solids", Physical Review, vol. 166, Issue 2, Feb. 10, 1968, pp. 332-347.

\* cited by examiner

METHOD AND SYSTEM FOR APPLYING NQR PULSE SEQUENCES

TECHNICAL FIELD

This disclosure relates to nuclear quadrupole resonance (NQR) and, more particularly, to using nuclear quadrupole resonance (NQR) for determining properties of substances.

BACKGROUND

Nuclear quadrupole resonance (NQR) is a phenomenon where atomic nuclei generate resonant signals when an oscillating magnetic field at a particular frequency is applied to the nuclei. Some atomic nuclei can generate resonant signals responsive to two or more different applied frequencies. Different atomic nuclei will have different resonant frequencies. For example, the resonant frequencies of nitrogen are different from the resonant frequencies of chlorine. Also, atomic nuclei of the same chemical element that are located within different chemical species can have different resonant frequencies. For example, the nitrogen nuclei located within the chemical species ammonium nitrate will have different resonant frequencies from nitrogen nuclei located within RDX. Furthermore, atomic nuclei of the same chemical element that are located within different sites of a chemical species can also have different resonant frequencies. Such NQR phenomena can be used to determine properties of a substance.

SUMMARY

This summary is provided to introduce a selection of concepts that are further described below in the detailed description. This summary is not intended to identify key or essential features of the claimed subject matter, nor is it intended to be used as an aid in limiting the scope of the claimed subject matter.

Illustrative embodiments of the present disclosure are directed to a method for determining presence of a chemical species within a substance using nuclear quadrupole resonance (NQR). The method includes applying an NQR pulse sequence to the substance using a non-resonant transmitter circuit. The method further includes detecting a NQR signal within the substance and determining presence of a chemical species within the substance using the NQR signal.

In various embodiments, the NQR pulse sequence is applied at a first frequency selected to match at least one known NQR frequency of a first set of atomic nuclei within the chemical species. The NQR pulse sequence generates a first NQR signal within the substance and this signal is detected.

In some embodiments, two different NQR pulse sequences are applied to the same set of atomic nuclei. The frequency of the first NQR pulse sequence is selected to match a first known NQR frequency of the first set of atomic nuclei within the chemical species. A second NQR pulse sequence includes at least one pulse at the first frequency and a pulse sequence segment at a second frequency selected to match a second known NQR frequency of the first set of atomic nuclei.

The second pulse sequence segment generates a second NQR signal within the substance and that second NQR signal is detected. The presence of the chemical species within the substance is determined by comparing the first NQR signal and the second NQR signal. In a particular embodiment, amplitude of the first NQR signal and amplitude of the second NQR signal are compared to determine the presence of the chemical species within the substance.

In yet further illustrative embodiment, two different NQR pulse sequences are applied to different sets of atomic nuclei. The frequency of the first NQR pulse sequence is selected to match a first known NQR frequency of a first set of atomic nuclei within the chemical species. A second NQR pulse sequence is applied at a frequency selected to match at least one known NQR frequency of a second set of atomic nuclei within the chemical species.

The second NQR pulse sequence generates a second NQR signal and that second NQR signal is detected. The presence of the chemical species within the substance is determined using the first NQR signal and the second NQR signal. In some embodiments, the first set of atomic nuclei and the second set of atomic nuclei are different chemical elements. In further specific embodiments, the first set of atomic nuclei and the second set of atomic nuclei are the same chemical elements located at different sites within the chemical species.

Various embodiments of the present disclosure are also directed to a method for applying a nuclear quadrupole resonance (NQR) sequence to a substance. The method includes applying an NQR pulse sequence to the substance using a non-resonant transmitter circuit. The NQR pulse sequence includes a first pulse sequence segment at a first frequency selected to match a first known NQR frequency of a first set of atomic nuclei and a second pulse sequence segment at a second frequency selected to match a second known NQR frequency of a second set of atomic nuclei. The second pulse sequence segment is initiated before the first set of atomic nuclei reach thermal equilibrium.

In some embodiments, the second pulse sequence segment is at least partially interposed within the first pulse sequence segment.

In further specific embodiments, the NQR pulse sequence includes at least three pulse sequence segments that are applied at different frequencies and configured to generate NQR signals in three different sets of atomic nuclei and at least two of the pulse sequence segments are at least partially interposed within the first pulse sequence segment.

Exemplary embodiments of the present disclosure are also directed to a system for applying nuclear quadrupole resonance (NQR) sequences to a substance and determining presence of a chemical species within the substance using the sequences. The system includes a coil for applying NQR pulse sequences to the substance and a NQR transmitter with a non-resonant NQR transmitter circuit electronically coupled to the coil. The system further includes a processor and a memory for storing instructions executable by the processor to perform processes that include providing NQR pulse sequences to the NQR transmitter.

BRIEF DESCRIPTION OF THE DRAWINGS

Further features and advantages will become more readily apparent from the following detailed description when taken in conjunction with the accompanying drawings.

DETAILED DESCRIPTION

Illustrative embodiments of the present disclosure are directed to systems and methods for applying a nuclear magnetic resonance (NQR) sequence to a substance. In particular, various embodiments are directed to using NQR to detect particular chemical species within a substance. To this end, exemplary embodiments apply NQR pulse sequences to the substance using broadband NQR electronics with a non-resonant transmitter circuit. Such broadband NQR electronics can quickly switch between many frequencies and can more efficiently apply NQR pulse sequences to detect particular chemical species within the substance. Details of various embodiments are discussed below.

Broadband NQR electronics can switch between frequencies that are outside a natural resonant frequency bandwidth of a coil with a tuned circuit. In other words, broadband electronics do not depend on tuning a coil to set a particular frequency. In contrast to conventional narrowband systems, which use mechanical switches and banks of fixed capacitors to tune the coil, various embodiments of the broadband electronics described herein achieve multi-frequency operation without a need for hardware modulation (e.g., switching between fixed capacitors or tuning between variable capacitors). In this manner, the broadband electronics are frequency insensitive and allow the pulse sequence frequency to be dynamically varied by a spectrometer while maintaining phase coherence of an output waveform.

In some cases, the broadband NQR electronics can switch between frequencies with a frequency difference (Δf) as great as 10% of an initial applied frequency. In various other embodiments, the frequency can be even greater (e.g., 20% 30% or 50%). Also, in some embodiments, the broadband NQR electronics can switch between frequencies in less than 5 μs. In yet further embodiments, the broadband NQR electronics can switch between frequencies in less than 20 μs or 50 μs. Furthermore, in some embodiments, the broadband NQR electronics can operate within a frequency range of 100 kHz and 3.2 MHz.

Figure 1A:
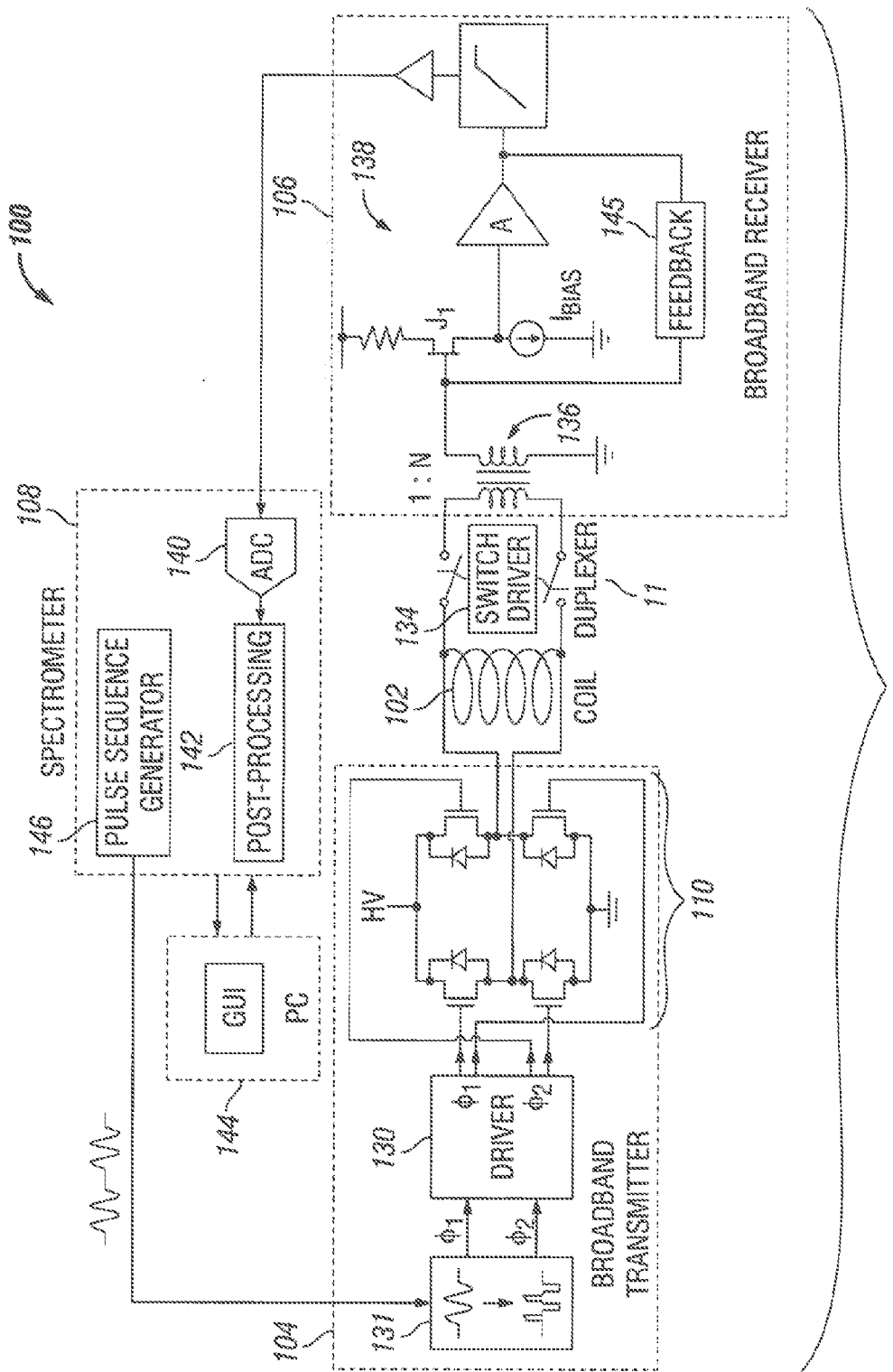
FIG. 1A shows a broadband NQR device in accordance with one embodiment of the present disclosure.

FIG. 1A shows broadband NQR device 100 in accordance with one embodiment of the present disclosure. The broadband NQR device 100 includes a coil 102 that is coupled to broadband NQR electronics 104, 106, 108. A sample substance is located inside and/or outside of the coil 102. The broadband NQR electronics include a broadband transmitter 104 and a broadband receiver 106. Each of the transmitter 104 and the receiver 106 are coupled to the coil 102.

Figure 1B:
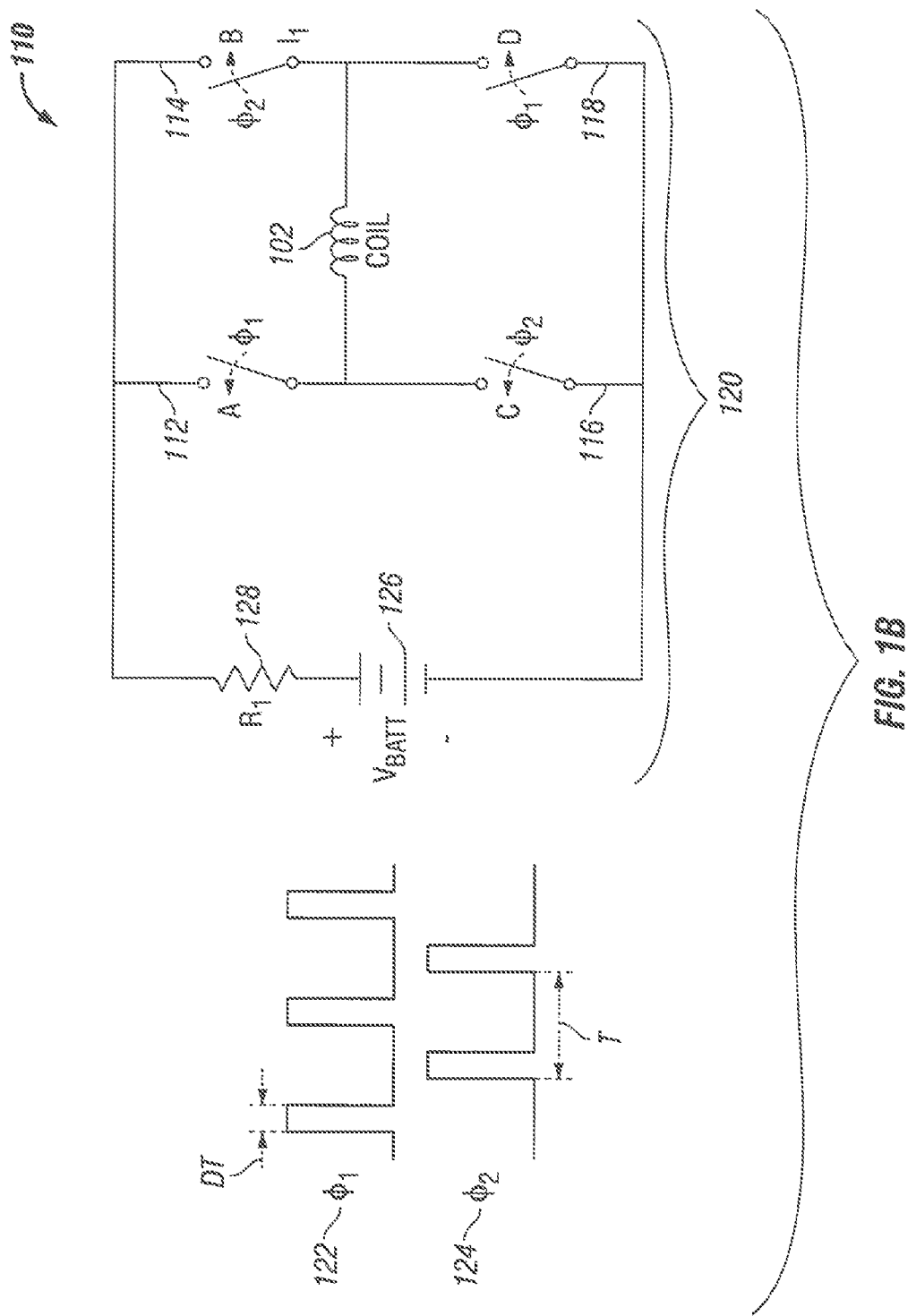
FIG. 1B shows a non-resonant NQR transmitter circuit in accordance with one embodiment of the present disclosure.

The broadband NQR transmitter 104 includes a non-resonant NQR transmitter circuit 110 that is coupled to the coil 102. The transmitter circuit 104 is "non-resonant" because the resonant frequency of the circuit does not need to match the Larmor frequency of interest. In contrast, as explained above, conventional circuits set their resonant frequencies to match the Larmor frequency of interest by selecting a particular capacitance for the circuit. Although the non-resonant transmitter circuit 110 and coil 102 may use capacitors and have some associated capacitance, this capacitance is not specifically selected to match a Larmor frequency of interest. FIG. 1B shows a non-resonant NQR transmitter circuit 110 in accordance with one specific embodiment of the present disclosure. In this specific example, the NQR transmitter circuit 110 includes a set of four switches: A 112, B 114, C 116 and D 118. These switches control the timing and the direction of the current flow in the coil. Turning these switches on and off using a certain switching logic generates an alternating current in the coil and thus produces RF irradiation. The switching logic often includes a period of positive current followed by a period of negative current, simulating a sinusoidal waveform. Repeating this pattern at a given frequency allows the generation of RF power at a particular frequency. In one particular embodiment, the switches 112, 114, 116, 118 are transistors, such as metal-oxide-semiconductor field-effect transistors (MOSFET), insulated gate bi-polar transistors (IGBT), or various other switches based upon the high frequency switching (HFS) family. In various embodiments, the switches can switch at less than 10 ns. The switches 112, 114, 116, 118 are arranged in a circuit 120 known as an H-bridge, as shown in FIG. 1B. In one embodiment, the switches 112, 114, 116, 118 are controlled by two non-overlapping digital signals denoted as $\varphi_1$ and $\varphi_2$ 122, 124. The signals $\varphi_1$ and $\varphi_2$ 122, 124 include a switching logic, which is used to drive the two sets of switches, (A and D) and (B and C), such that a voltage source $V_{batt}$ 126 is connected with alternating polarity across the coil 102 and an oscillatory coil current ($I_1$) is created. A load resistor $R_1$ 128 or fuse can be used in series with the voltage source to limit the current that is applied to the switches 112, 114, 116, 118. The digital signals denoted as $\varphi_1$ and $\varphi_2$ 122, 124 are used to control the switches 112, 114, 116, 118 and a desired frequency of an NQR sequence (e.g., a multi-segment sequence) is achieved by repeating these signals at the desired frequency. In some embodiments, other digital signals can be used to control each of the switches 112, 114, 116, 118 individually. For example, the signals may include high components (e.g., $\varphi_{1H}$ and $\varphi_{2H}$) that control the high-side switches 112, 114 and low components (e.g., $\varphi_{1L}$ and $\varphi_{2L}$) that control the low-side switches 116, 118.

The broadband NQR transmitter 104 also includes a driver 130 that is coupled to the non-resonant NQR transmitter circuit 110. In one particular embodiment, the driver 130 can be a computer processor. The driver 130 is used to control the switches 112, 114, 116, 118 within the transmitter circuit 110. The driver 130 switches the switches 110 according to the switching logic within the digital signals (e.g., $\varphi_1$ and $\varphi_2$). In various embodiments, the driver 130 also receives NQR pulse sequences from an NQR spectrometer 108. In some embodiments, the NQR pulse sequences are sent along a plurality of channels. An adder circuit (not shown) can be used to combine the plurality of channels. Also, in various embodiments, the transmitter 104 includes a comparator 131 for receiving the NQR pulse sequences from the spectrometer 108 and generating a square waveform that is then provided to the driver 130. The NQR pulse sequences can be translated by the driver 130 into the particular switching logic by selecting positive and negative waveforms of the NQR pulse sequences and then conditioning the waveforms to an appropriate voltage. In this manner, modulating hardware, such as a tuning capacitor, is not necessary in order to achieve a particular frequency. Instead, the frequency is modulated directly by the spectrometer 108.

The coil 102 is also coupled to the broadband NQR receiver 104 so that NQR resonant signals can be detected within the sample. The coil 102 is coupled to the broadband receiver 106 using a duplexer 132. The duplexer 132 decouples the receiver 106 from the coil 102 when the coil is operating in a transmitting mode (e.g., transmitting an NQR pulse sequence). In this manner, the duplexer 132 protects the receiver 106 during a transmitting mode. In one particular embodiment, the duplexer 132 includes switches and a switch driver 134 that opens the switches during a transmitting mode and closes the switches during a receiving mode of operation. In various embodiments, the duplexer 132 includes two back-to-back field effect transistors (FETs) that are controlled by an isolated driver circuit. This configuration produces a bidirectional and broadband switch. The switch is bidirectional because the state of the switch is independent of the polarity of the voltage on the coil. For example, such a switch will remain OFF regardless of whether the voltage across the coil is positive or negative. The switch is broadband because a reference voltage for the driver is not connected to the same ground terminal as the remainder of the driver circuit. Control signals can be passed to the switch using various isolated signal transmission methods, such as magnetic transmission methods (e.g., using a transformer) or optical transmission methods (e.g., using an optoisolator). In some embodiments, a duplexer is not used when the device 100 includes separate transmit and receive coils.

Figure 1C:
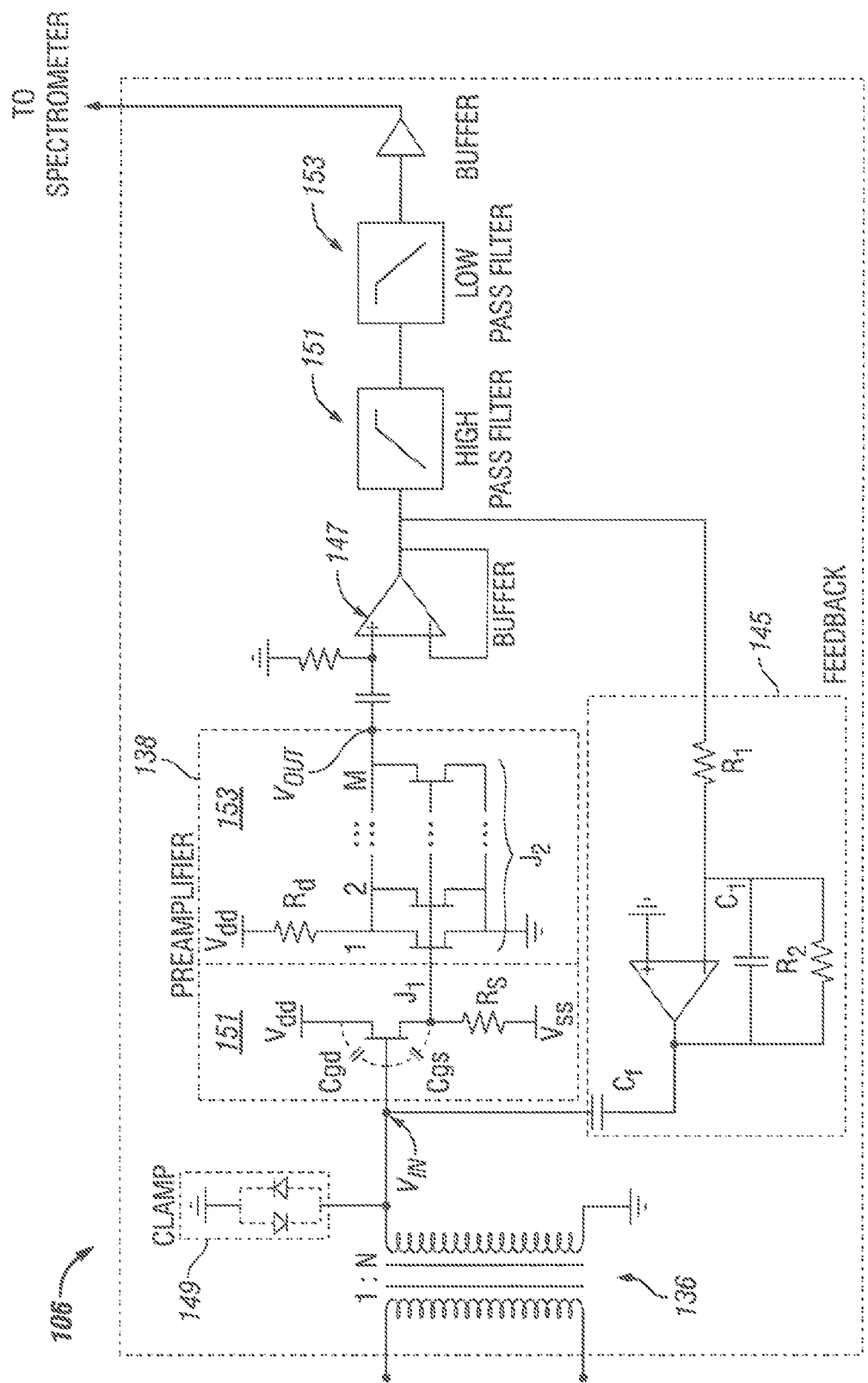
FIG. 1C shows a broadband NQR receiver in accordance with one embodiment of the present disclosure.

FIG. 1C shows the broadband NQR receiver 106 in more detail. The broadband NQR receiver can receive and process resonant NQR signals over a broad frequency range. In some embodiments, the ratio of the highest operating frequency and lowest operating frequency is greater than 5. In various embodiments, this ratio is as great as 30 or 50. The highest operating frequency and lowest operating frequency are defined by the frequency range over which the performance of the receiver is satisfactory for its application. For example, in one case, the frequency range is the range over which the input-referred noise of the receiver is less than that of a 1-Ω resistor. This level of noise is considered adequate for NQR coils with resistance of 1Ω or larger. In various embodiments, the frequency range satisfying this condition is 3 MHz to 0.1 MHz Various embodiments of the broadband NQR receiver 106 include a transformer 136 that receives the NQR resonant signal from the coil 102 and amplifies the signal by proving a voltage gain. In some embodiments, the transformer is directly coupled to the duplexer 132. The transformer 136 may be a step-up transformer with a turn ratio of 1:N. The turn ratio may be in the range of 1:2 to 1:10. However, in some embodiments, higher turn ratios can also be used. For low frequency operation (e.g., below 5 MHz), the transformer 136 may include a soft magnetic core to increase the inductance and performance of the transformer. For higher frequency operation (e.g., above 5 MHz), a transformer 136 without a magnetic core can be used. In illustrative embodiments, the transformer 136 includes a low insertion loss and a bandwidth that significantly exceeds the highest operating frequency of the receiver 106. In some embodiments, for transformers 136 with magnetic cores, a magnetic shield may be installed around the transformer. The shield reduces the magnetic field projected from the NQR magnet into the transformer 136, which improves the performance of the transformer.

The receiver 106 also includes a preamplifier 138 that follows the transformer 136. In some embodiments, the preamplifier is directly coupled to the transformer 136. The transformer 136 provides a broadband passive and low-noise voltage gain of a NQR signal that is detected at the coil 102. This voltage gain occurs before the preamplifier 138. In some cases, such a transformer-coupled topology results in a low noise figure (NF) over a wide frequency range. In one specific example, the transformer 136 has a turn ratio of 1:10 to amplify an input signal above a noise floor of the preamplifier 138. Such a configuration can produce a low input-referred noise at frequencies up to 10 MHz (e.g., 0.1 nV/Hz$^{1/2}$, which is equal to the thermal noise produced by a 0.6Ω resistor at 300 K). After the transformer, the NQR signal is passed to the preamplifier 138, which further amplifies the NQR signal.

The preamplifier 138 includes a common-drain amplifier stage 151 and a common-source amplifier stage 153. In FIG. 1C, the common-drain amplifier stage 151 includes a transistor ($J_1$) that is configured as a common-drain amplifier. The transistor ($J_1$) has an input signal fed at the gate of the transistor and an output signal taken from the source of the transistor (e.g., also known as a source follower). In one specific embodiment, the transistor ($J_1$) is a junction gate field-effect transistor (JFET). A gate-source capacitance ($C_{gs}$) and a gate-drain capacitance ($C_{gd}$) are intrinsic to the transistor ($J_1$). By configuring the transistor ($J_1$) as a source follower, the preamplifier 138 advantageously applies the gate-drain capacitance ($C_{gd}$) at an input terminal of the transistor. The gate-drain capacitance ($C_{gd}$) is much smaller than the gate-source capacitance ($C_{gs}$) when the transistor ($J_1$) is biased in its usual region of operation (e.g., known as saturation). The maximum RF frequency that can be amplified by the preamplifier 138 with low noise (e.g., useful bandwidth of the preamplifier) is proportional to:

$$1/\sqrt{C_{input}}$$ Eq. 33 where $C_{input}$ is the total capacitance at the input of the transistor ($J_1$). The transistor ($J_1$) contributes a significant portion of total capacitance at the input of the transistor ($C_{input}$), so reducing its contribution from the gate-source capacitance ($C_{gs}$) to the gate-drain capacitance ($C_{gd}$) significantly increases the bandwidth of the preamplifier.

In FIG. 1C, a single transistor is shown within the common-drain amplifier stage 151 of the preamplifier 138. In other embodiments, however, the common-drain amplifier stage 151 can include a plurality of common-drain amplifiers that are, for example, coupled in parallel (e.g., a plurality of transistors configured as source followers and coupled in parallel).

Once the NQR signal passes the common-drain amplifier stage 151, the NQR signal is further amplified by the common-source amplifier stage 153, which provides a voltage gain to the signal. In the embodiment shown in FIG. 1C, the common-source amplifier stage includes 153 a number (M) of transistors that are coupled in parallel. In some embodiments, the number of transistors (M) can be between 2 and 10. The common-source stage 153 reduces the noise that the stage contributes to a level that is 1/M times that contributed by the common-drain amplifier stage 151 (in power units). By making M much larger than 1, the noise contributed by the stage can be reduced, thus minimizing the noise floor of the preamplifier 138.

The examples above use JFETs (e.g., as $J_1$ and as $J_2$), however, other types of transistors can also be used, such as bipolar junction transistors (BJT) and/or metal oxide field effect transistors (MOSFET). In various embodiments, the transistors have low current and voltage noise, and also include small capacitances between their terminals.

Figure 1D:
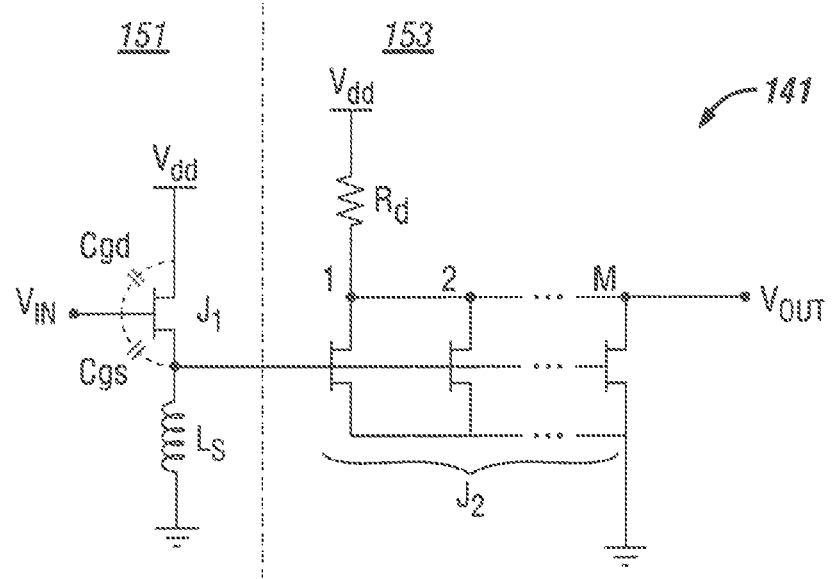
FIG. 1D shows a preamplifier in accordance with one embodiment of the present disclosure.

FIG. 1D shows another embodiment of a preamplifier 141 that can be used with the NQR receiver 106. The preamplifier 138 of FIG. 1C uses a resistor ($R_s$) at the source of the transistor ($J_1$) to set a DC bias current through the transistor. A negative power supply ($V_{SS}$) is applied at an end of the resistor ($R_S$) because of a DC voltage drop across the resistor. In one specific embodiment, the resistor is 820Ω and the power supply is −5 V. In contrast to the preamplifier 138 of FIG. 1C, the preamplifier 141 of FIG. 1D replaces the resistor ($R_S$) with a large inductor ($L_S$) that is coupled to the transistor ($J_1$). In one specific embodiment, the inductor has an inductance of 470 µH. By using such an arrangement, the preamplifier 141 of FIG. 1D can omit the use of the power supply ($V_{SS}$).

Figure 1E:
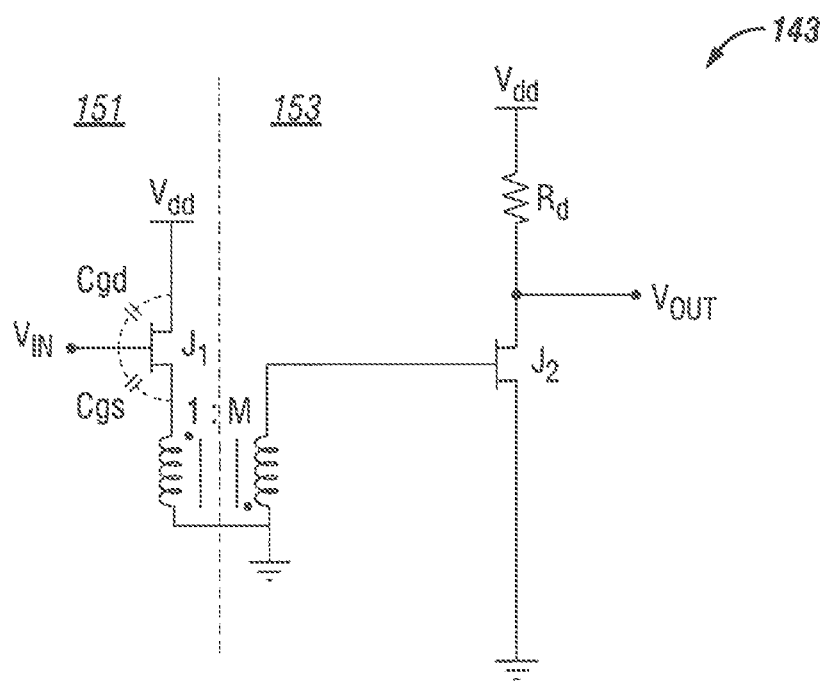
FIG. 1E shows a preamplifier in accordance with another embodiment of the present disclosure.

FIG. 1E shows yet another embodiment of a preamplifier 143 that can be used with the NQR receiver 106. In this embodiment, the preamplifier 143 includes a second transformer that is coupled between the common-drain amplifier stage 151 and the common-source amplifier stage 153. The second transformer amplifies the NQR signal by providing a voltage gain to the signal. In some embodiments, the voltage gain provided by the transformer is substantially noiseless. The transformer may be step-up transformer with a turns ratio of 1:M (e.g., between 1:2 and 1:10). In some embodiments, the second transformer includes a magnetic core, while, in other embodiments, a core is not used. If a magnetic core is used, then the transformer may be enclosed with a magnetic shield. The shield prevents the magnetic field of the NQR magnet from penetrating the transformer core.

This second transformer is followed by the common-source amplifier stage 153. In this specific embodiment, the common-source amplifier stage 153 includes a single transistor ($J_2$) configured as a common-source amplifier. Other embodiments, however, may include additional transistors.

The second transformer reduces the noise contributed by the common-source amplifier stage 153 to a level that is $1/M^2$ times that contributed by the common drain amplifier stage 151 (in power units). Thus, the noise contribution of the common-source amplifier stage 153 and later stages can be made insignificant for relatively small values of M, and, in this manner, the configuration creates a very low-noise preamplifier. For example, in an embodiment where M is 4, the total input-referred noise of the preamplifier is only 6.25% larger than that of the common drain amplifier stage alone. In various embodiments, the preamplifier 143 also advantageously saves a significant amount of power. In particular, the resistor or the inductor at the transistor ($J_1$) can be omitted because the primary side of the second transformer sets the DC bias point for the transistor ($J_1$) and the secondary side of the transformer does not need to consume DC power.

In various embodiments, the preamplifiers 138, 141, 143 described herein have increased bandwidth (e.g., over 3 MHz for a NQR coil of inductance 15 μH), improved settling time, and similar input-referred noise, as compared to conventional preamplifiers. One conventional example of a transformer-coupled preamplifier for low frequency operation (e.g., less than 50 kHz) is the SR-554, which can be obtained from Stanford Research Systems™.

As shown in FIG. 1C, the broadband receiver 106 includes a DC blocking network 147 that is disposed after the preamplifier 138. The DC blocking network 147 sets an output ($V_{out}$) of the preamplifier 138 to ground, which maximizes the overall dynamic range of the receiver 106.

In the specific embodiment of FIG. 1C, the broadband receiver 106 also includes a feedback network 145. The feedback network is coupled to the preamplifier 138 and configured to reduce settling time of the preamplifier. In this case, the feedback network is coupled to an input ($V_{in}$) of the preamplifier 138 at one end and after the DC blocking network 147 at the other end. The feedback network 145 removes unwanted high-frequency resonances between inductive impedance at the NQR coil 102 and capacitive input impedance ($C_{input}$) at the preamplifier 138. These resonances are produced by RF pulses that are applied to the coil 102 by the transmitter 104 and can adversely affect the settling time of the receiver 106. To reduce the settling time, without adding noise, the particular feedback network 145 shown in FIG. 1C uses an op-amp based integrator circuit followed by a small feedback capacitor ($C_f$). The feedback network 145 produces a noiseless damping resistance ($R_{damp}$) between the input of the preamplifier ($V_{in}$) and ground to remove these resonances. The noiseless damping resistance ($R_{damp}$) can be defined by:

$$R_{damp} = \tau/(AC_f),$$ Eq. 34 where $\tau = R_1 C_1$ is the time constant of the integrator circuit, and A is the overall voltage gain of the preamplifier. Other types of feedback networks can also be used. For example, a feedback resistor ($R_f$) can replace the capacitor ($C_f$) and a voltage gain circuit can replace the integrator circuit.

In various embodiments, the settling time of the receiver can be further improved by limiting the signal amplitude at various locations within the receiver 106 using diode clamps. In the embodiment shown in FIG. 1C, a diode clamp 149 is coupled between the transformer 136 and the input ($V_{in}$) of the preamplifier 138 (e.g., at the gate of the transistor ($J_1$)). The diode clamp 149 includes a pair of cross-coupled diodes that limit maximum signal amplitude across the diodes to approximately a threshold voltage of each diode ($V_{on}$). Values of the threshold voltage ($V_{on}$) for silicon diodes can range from 0.6 V to 0.7 V. Similar diode clamps can also be used at other locations within the receiver 106, such as after the output ($V_{out}$) of the preamplifier and/or between the common-drain stage (J1) and common-source stage (J2).

The broadband NQR electronics 104, 106, 108 also include a spectrometer 108. In some embodiments, the output of the preamplifier 138 is passed through further stages of analog filtering before being sent to the spectrometer 108. For example, high-pass and low-pass filters can set the minimum and maximum detectable NQR frequency, respectively. The cutoff frequencies of these filters can be varied based on the application.

In some embodiments, the detected resonant signal is output by the broadband receiver 138 in analog form. In such embodiments, the spectrometer 108 may include a digitizer 140 for converting the detected resonant signal into digital data. Furthermore, in various embodiments, demodulation of the NQR signal can occur within the spectrometer 108. In various other or alternative embodiments, however, demodulation of the NQR signal can also occur within the broadband NQR receiver 106. The spectrometer 108 also includes a post-processor 142 that is used to interpret the detected digital resonant data and to determine NQR properties from the detected data. This data can be presented to a user using an operator module 144 with a graphical user interface (GUI). In various embodiments of the present disclosure, the operator interface 144 and the GUI are not part of the broadband NQR electronics 104, 106, 108. The spectrometer 108 also includes a pulse sequence generator 146. The pulse sequence generator 146 generates NQR sequences based upon parameters selected by an operator at the operator module 144. The pulse sequence generator 146 provides the sequences to the transmitter 104. In one particular embodiment, the spectrometer 108 is a Kea™, which can be obtained from Magritek™. The spectrometer 108 can be controlled from the operator module 144 using Prospa™ software, which can also be obtained from Magritek™.

Further details of broadband electronics (e.g., non-resonant NMR systems) are described in U.S. Publication No. 2012/0001629 published on Jan. 5, 2012, which application is incorporated herein, in its entirety, by reference.

Figure 2:
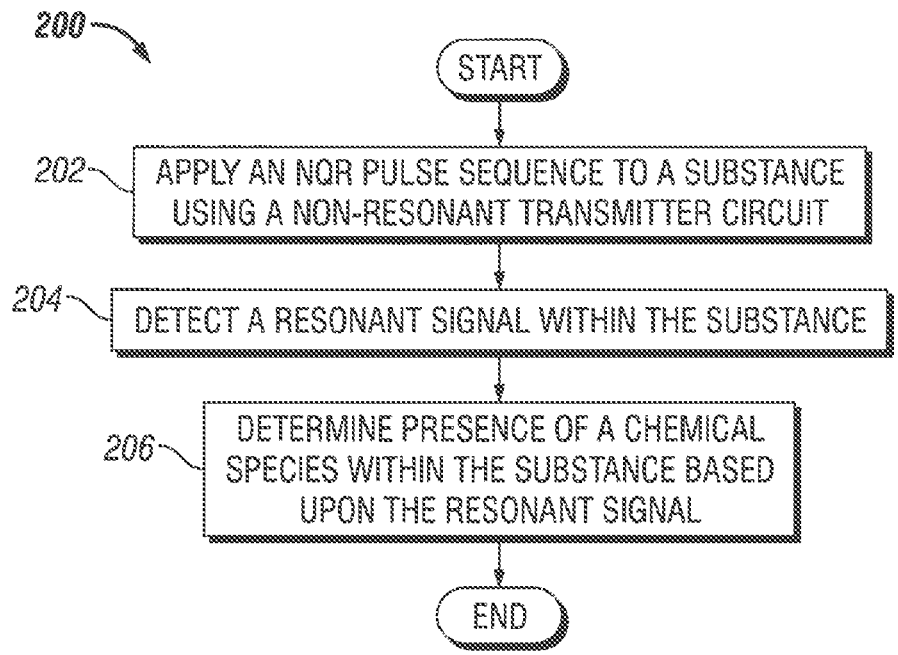
FIG. 2 shows a method of applying an NQR pulse sequence in accordance with one embodiment of the present disclosure.

FIG. 2 shows a method 200 of applying an NQR pulse sequence in accordance with one embodiment of the present disclosure. The method 200 includes applying a NQR pulse sequence to the substance using a non-resonant NQR transmitter circuit. In some case, the NQR pulse sequence is applied to the substance in the presence of a static magnetic field. In other embodiments, the NQR pulse sequence is applied without a static magnetic field.

Figure 3:
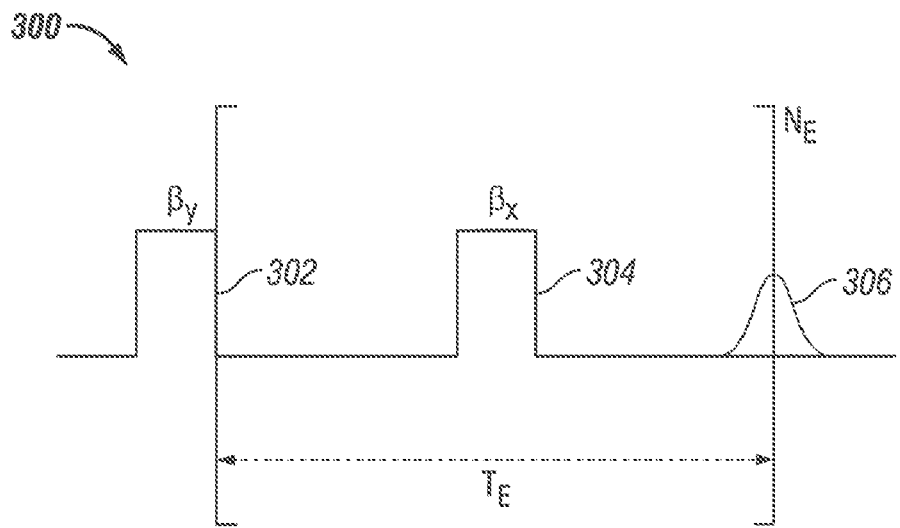
FIG. 3 shows an NQR spin-locked spin echo (SLSE) pulse sequence in accordance with one embodiment of the present disclosure.
Figure 7:
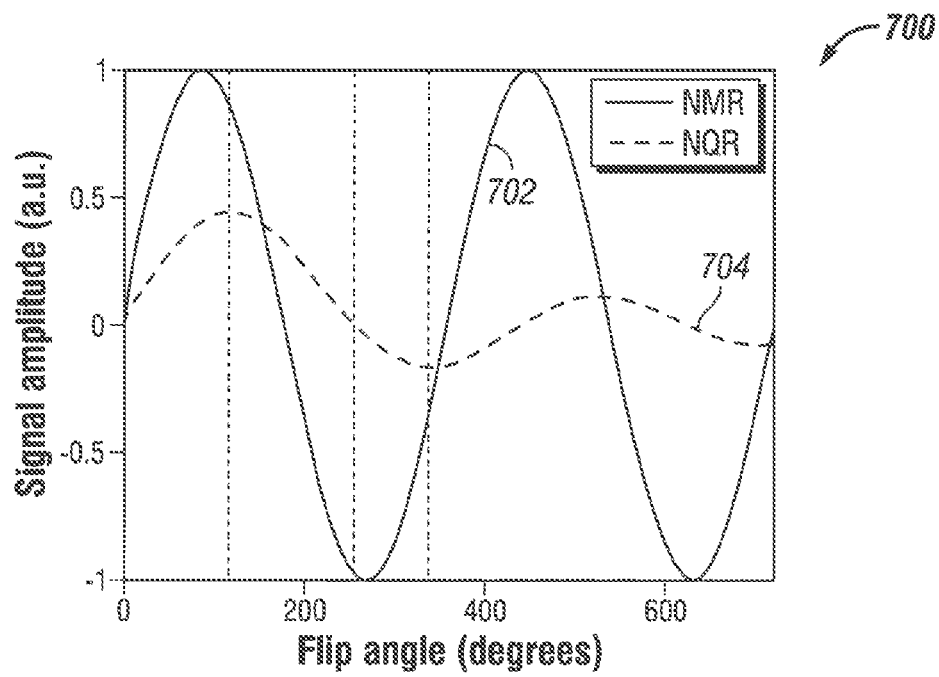
FIG. 7 shows a plot of NMR and NQR signal amplitude versus nutation angle in accordance with one embodiment of the disclosure.

FIG. 3 shows an NQR pulse sequence 300 in accordance with one embodiment of the present disclosure. The NQR pulse sequence 300 includes a single excitation pulse 302 followed by a number ($N_E$) of refusing pulses 304 and corresponding echoes 306. In one specific example, the excitation pulse 302 is phase-shifted 90 degrees with respect to the refocusing pulses 304 and the nutation angle β is set as 119 degrees. As shown in FIG. 7, a high amplitude signal is obtained when the nutation angle is set at 119 degrees. Various other embodiments are not limited to such specific phases and nutation angles. For example, the phase may vary between 0 degrees and 360 degrees and the nutation angle can vary between 0 degrees and 360 degrees.

In one specific embodiment, the NQR pulse sequence is a spin-locked spin echo (SLSE) pulse sequence. In many cases, such SLSE pulse sequences produce echo decay that is bi-exponential. The echo decay includes fast-decaying and slow-decaying components. A time constant ($T_{SLSE}$) of the slow-decaying component approaches $T_{1\rho}$ as echo spacing ($T_E$) approaches zero. $T_{1\rho}$ is the spin-lattice relaxation in a rotating frame that is rotating along with the applied oscillating field ($B_1$). The value of the time constant ($T_{SLSE}$) decreases as the echo spacing increases, but the time constant is often much larger than $T_2$ relaxation time, which is very short in solids. Given these constraints, various embodiments of the method add echoes together to improve signal to noise ratio (SNR). The qualitative behavior of the SLSE sequence can be determined by using a model which assumes that a steady-state condition is reached after the first few refocusing pulses (e.g., 5 refocusing pulses). Under such a model, the spectrum of the pulse train consists of a carrier signal of amplitude $\overline{B_1}$ and a set of sidebands separated from the carrier by integral multiples of $1/T_E$, where $T_E$ is the echo spacing. $\overline{B_1}$ can be determined by:

$$\overline{B_1} = B_1(T_P/T_E) \qquad \text{Eq. 1}$$

where $T_P$ is the refocusing pulse length. When $T_E/T_2$ is small, the sidebands are non-secular and can be ignored, so the conditions for spin locking in the field $\overline{B_1}$ are satisfied. As a result, the signal decays with a time constant that approaches $T_{1\rho}$. Various embodiments of the present disclosure are not limited to SLSE sequences. In another specific example, a steady-state free precession (SSFP) sequence can be used.

In various embodiments of the present disclosure, the NQR pulse sequence is applied to the substance at a particular frequency. The frequency is selected to match a known resonant frequency of a set of atomic nuclei to be detected within the substance. The presence or absence of the atomic nuclei can be used to determine the presence or absence of a chemical species within the substance because atomic nuclei located within a particular chemical species will have a particular set of resonant frequencies. For example, a set of nitrogen atomic nuclei located within the chemical compound glycine will have resonant frequencies at 737 kHz and 1052 kHz. In one specific embodiment, the method includes applying the NQR pulse sequence at 737 kHz to detect the presence of glycine within the substance.

According to FIG. 2, the method also includes detecting a resonant signal within the substance 204. In some cases, the applied NQR pulse sequence will generate a resonant signal within the substance. This resonant signal can be detected using the NQR system with the coil and electronics. In illustrative embodiments of the present disclosure, NQR pulse sequences are applied to the substance using a single coil. Also, the resonant signals generated by the NQR sequences are detected by the single coil. In some embodiments, separate coils and electronics can be used to apply sequences and detect resonant signals.

The resonant signals generated at the substance can be used to determine NQR properties for the substance (e.g., NQR frequencies, $T_1$ relaxation time, and/or $T_2$ relaxation time) 206. In turn, the NQR properties can be used to determine physical properties of the substance, such as the chemical composition of the substance and/or the presence of a solid crystalline phase or a powder phase.

Figure 4:
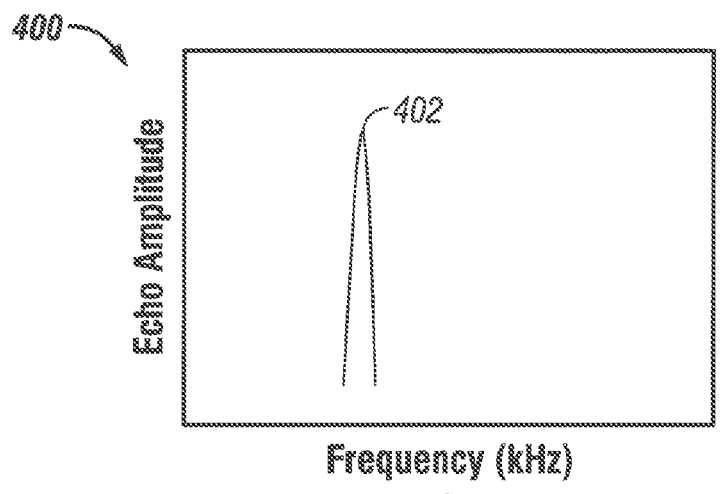
FIG. 4 shows a peak of a detected resonant signal in accordance with one embodiment of the present disclosure.

Furthermore, the resonant signal can be used to determine the presence of a specific chemical species within the substance. In the glycine example, if a resonant signal at 737 kHz is detected, this may indicate the presence of glycine within the substance. FIG. 4 shows a plot 400 of echo amplitude versus frequency in accordance with one embodiment of the present disclosure. The plot 400 shows a peak 402 within the detected resonant signal at 737 kHz. The peak 402 indicates the presence of glycine within the sample. In contrast, the absence of a peak at 737 kHz indicates the absence of glycine within the substance.

Figure 5:
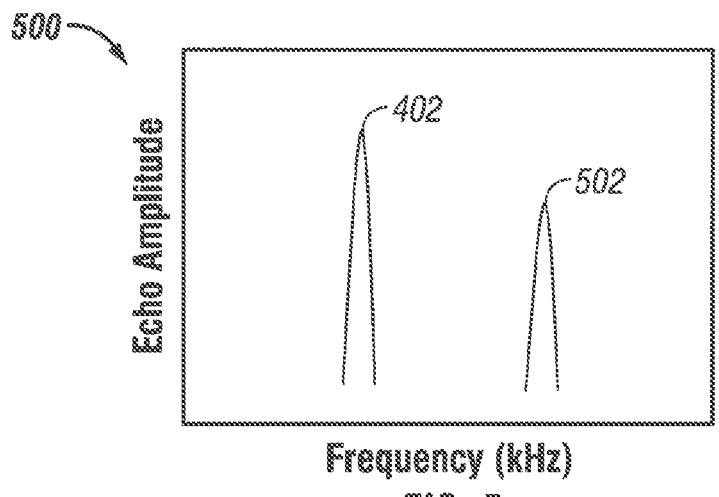
FIG. 5 shows a second peak of a detected resonant signal in accordance with one embodiment of the present disclosure.

In various embodiments, after process 206, the method is complete and the presence or absence of a particular chemical species can be communicated to an operator of the NQR system. In further exemplary embodiments, a second NQR pulse sequence at a second frequency is applied to the sample. Applying additional NQR sequences at other frequencies can improve the accuracy of determining the presence or absence of a chemical species. In the glycine example, a second NQR pulse sequence is applied at 1052 kHz. If a resonant signal at 737 kHz is detected, this may further indicate and confirm the presence of glycine within the substance. FIG. 5 shows a plot 500 of echo amplitude versus frequency in accordance with one embodiment of the present disclosure. The plot 500 shows a second peak 502 within the detected resonant signal at 1052 kHz. The presence of both peaks 402, 502 indicates the presence of glycine within the sample. In contrast, the absence of one or both of the peaks indicates the absence of glycine within the substance. This determination can then be communicated to the operator of the NQR system.

In further illustrative embodiments, additional measurements are made. In various embodiments 4, 6, 10, and even 20 such NQR pulse sequences at different frequencies can be applied to the substance. The additional measurements can be used to detect atomic nuclei within different sites of the chemical species. Atomic nuclei of the same chemical element that are located within different sites of a chemical species can have different resonant frequencies. For example, TNT (2,4,6-trinitrotoluene) includes six sites for nitrogen atomic nuclei. The nitrogen atomic nuclei at each different site have different resonant frequencies. To determine the presence of such multi-site chemical species, a first NQR sequence can be applied at a first frequency to detect the presence of a set of nitrogen nuclei at a first site within the chemical species. The first frequency is selected to match a known resonant frequency of nitrogen nuclei at the first site (e.g., 842 kHz or 751 kHz for TNT). In some embodiments, a second NQR sequence can be applied at a second frequency to detect the presence of a set of nitrogen nuclei at a second site. The second frequency is selected to match a known resonant frequency of nitrogen nuclei at the second site (e.g., 859 kHz or 768 kHz for TNT). Next, a third NQR sequence can be applied at a third frequency to detect the presence of a set of nitrogen nuclei at a third site within the chemical species (e.g., 837 kHz or 743 kHz for TNT). In some embodiments, the measurements continue until each site of the atomic nuclei within the chemical species is investigated. With respect to TNT, at least some or all of the six possible nitrogen sites can be measured.

In additional or alternative embodiments, additional measurements can be used to detect different atomic nuclei within the same chemical species. Atomic nuclei of different chemical elements can have different resonant frequencies. For example, Cocaine Hydrochloride ($C_{17}H_{21}NO_4 \cdot HCL$) includes two sites for nitrogen atomic nuclei and a single site for chlorine atomic nuclei. To determine the presence of such chemical species within the substance, a first NQR sequence can be applied at a first frequency to detect the presence of a set of nitrogen nuclei within the chemical species. The first frequency is selected to match a known resonant frequency of nitrogen nuclei within the chemical species (e.g., 961 kHz or 806 kHz for Cocaine Hydrocloride). In some embodiments, a second NQR sequence can be applied at a second frequency to detect the presence of a set of chlorine nuclei within the chemical species. The second frequency is selected to match a known resonant frequency of chlorine nuclei within the chemical species (e.g., 2530 kHz for Cocaine Hydroclorice).

In exemplary embodiments of the present disclosure, the set of atomic nuclei to be detected can be any one of nitrogen, chlorine, and/or copper. Also, the chemical species can be a single chemical element such as nitrogen, chlorine, and copper, or a chemical compound, such as glycine, ammonium nitrate, TNT (2,4,6-trinitrotoluene), RDX (hexahydro-1,3,5-trinitro-1,3,5-triazine), cocaine hydro-chloride, and/or heroin hydro-chloride (3,6-diacetoxy-7,8-dehydro-4,5-epoxy-N-methylmorphinan hydrochloride monohydrate). Table 1 shows the spectral lines for nitrogen and chloride at each site within several chemical species. The column headings are described below.

"Chemical Species" is a particular chemical species of interest;

"Site #" is a position of an atomic nucleus within a particular chemical species;

"Type" is an atomic nucleus at a site (e.g., chemical element and isotope);

"Weight %" is a contribution of a site to a total weight of a molecule of a chemical species;

"QCC" is a quadrupole coupling constant for a site;

"η" is a symmetry parameter for a site;

"NQR Frequency" is a known resonant frequency of an atomic nucleus within a particular site within a chemical species;

"FWHM" is an NQR line width for a particular NQR frequency (full-width at half-maximum);

"$T_1$" is a $T_1$ relaxation time for an atomic nucleus at a particular site;

"$T_2$" is a $T_2$ relaxation time for an atomic nucleus at a particular site; and "dv/dT" is a temperature coefficient for a particular NQR frequency.

TABLE 1

| Chemical Species | Sites | | | | Spectral Lines At Each Site | | | | |
| --- | --- | --- | --- | --- | --- | --- | --- | --- | --- |
| | Site # | Type | Weight % | QCC | η | NQR Frequency (kHz) | FWHM (kHz) | $T_1$ (ms) | $T_2$ (ms) | dv/dT (kHz/° C.) |
| Glycine ($C_2H_5NO_2$) | 1 | amine-$^{14}$N | 18.7 | 1193 | 0.528 | 1052 | 2.8 | 43.4 | 12.5 | −.0195 |
| | | | | | | 737 | 0.8 | 50.0 | 17.1 | −.205 |
| Sodium Nitrite (NaNO$_2$) | 1 | nitro-$^{14}$N | 20.2 | 5497 | 0.378 | 4642 | 0.16 | 90.3 | 5.3 | −1.6 |
| | | | | | | 3604 | 0.12 | 280 | 3.3 | −1.2 |
| | | | | | | 1038 | 0.10 | 328 | 5.1 | −0.4 |
| Potassium Nitrate (KNO$_3$) | 1 | nitro-$^{14}$N | 13.9 | 751 | 0.022 | 567 | 0.11 | 20.1 (s) | — | −0.23 |
| | | | | | | 559 | 0.11 | 24.5 (s) | — | −0.19 |
| | 2 | $^{39}$K | 36.0 | 1326 | 0.171 | 665 | 0.80 | 1.9 (s) | — | −0.58 |
| Ammonium Nitrate ($H_4N_2O_3$) | 1 | nitro-$^{14}$N | 17.5 | 613 | 0.241 | 497 | 0.05 | 14 (s) | — | −0.46 |
| | | | | | | 423 | 0.06 | 16.6 (s) | — | 0.12 |
| L-proline ($C_5H_9NO_2$) | 1 | amine-$^{14}$N | 12.2 | 1495 | 0.975 | 1486 | 0.50 | 1.2 (s) | — | −0.546 |
| | | | | | | 757 | 0.12 | 2.4 (s) | — | −0.335 |
| | | | | | | 729 | 0.37 | 1.4 (s) | — | −0.211 |
| RDX ($C_3H_6N_6O_6$) | 1 | amine-$^{14}$N | 6.3 | 5735 | 0.622 | 5192 | 0.2 | 12.6 | 8.2 | −0.43 |
| | | | | | | 3410 | 0.4 | 11.1 | 6.2 | −0.06 |
| | | | | | | 1782 | — | — | — | −0.37 |
| | 2 | amine-$^{14}$N | 6.3 | 5799 | 0.615 | 5240 | 0.43 | 12.3 | 7.1 | −0.47 |
| | | | | | | 3458 | 0.54 | 12.1 | 5.7 | −0.33 |
| | | | | | | 1782 | — | — | — | −0.14 |
| | 3 | amine-$^{14}$N | 6.3 | 5604 | 0.602 | 5047 | 0.45 | 13.3 | 6.8 | −0.43 |
| | | | | | | 3359 | 0.43 | 14.6 | 6.3 | −0.27 |
| | | | | | | 1688 | — | — | — | −0.16 |
| | 4 | nitro-$^{14}$N | 6.3 | 394-460 | 1.0-0.41 | 405.1 | 0.25 | 15.9 | 7.3 | — |
| | | | | | | 396.2 | 0.3 | 18.1 | 6.2 | — |
| | | | | | | 381.4 | 0.3 | 13.5 | 7.5 | — |
| | 5 | nitro-$^{14}$N | 2 × 6.3 | 597 | 0.36 | 502.3 | 0.15 | 15.9 | 6.6 | −0.18 |
| | | | | | | 500.5 | 0.15 | 13.8 | 8.2 | −0.2 |
| | | | | | | 405.1 | 0.25 | 15.9 | 7.3 | — |
| | | | | | | 396.2 | 0.3 | 18.1 | 6.2 | — |
| | | | | | | 381.4 | 0.3 | 13.5 | 7.5 | — |
| | 6 | nitro-$^{14}$N | 2 × 6.3 | 597 | 0.36 | 502.3 | 0.15 | 15.9 | 6.6 | −0.18 |
| | | | | | | 500.5 | 0.15 | 13.8 | 8.2 | −0.2 |
| | | | | | | 405.1 | 0.25 | 15.9 | 7.3 | — |
| | | | | | | 396.2 | 0.3 | 18.1 | 6.2 | — |
| | | | | | | 381.4 | 0.3 | 13.5 | 7.5 | — |
| TNT ($C_7H_5N_3O_6$) | 1 | nitro-$^{14}$N | 3.1 | 1062 | 0.171 | 842 | 0.8 | 3.5 (s) | — | −0.181 |
| | | | | | | 751 | 0.7 | 2.2 (s) | — | −0.241 |
| | 2 | nitro-$^{14}$N | 3.1 | 1085 | 0.168 | 859 | 1.3 | 3 (s) | — | −0.223 |
| | | | | | | 768 | 0.7 | 9.8 (s) | — | −0.19 |
| | 3 | nitro-$^{14}$N | 3.1 | 1053 | 0.178 | 837 | 0.9 | 2.1 (s) | — | −0.122 |
| | | | | | | 743 | 0.4 | 3 (s) | — | −0.148 |
| | 4 | nitro-$^{14}$N | 3.1 | 1059 | 0.204 | 848 | 0.4 | 9.6 (s) | — | −0.151 |
| | | | | | | 740 | 1 | 5.5 (s) | — | −0.169 |
| | 5 | nitro-$^{14}$N | 3.1 | 1039 | 0.25 | 844 | 0.8 | 4.7 (s) | — | −0.121 |
| | | | | | | 714 | 0.7 | 4.3 (s) | — | −0.094 |
| | 6 | nitro-$^{14}$N | 3.1 | 1056 | 0.295 | 870 | 0.5 | 4 (s) | — | −0.109 |
| | | | | | | 714 | 0.7 | 4.3 (s) | — | −0.094 |

TABLE 1-continued

| Chemical Species | Sites | | | | | Spectral Lines At Each Site | | | | |
|---|---|---|---|---|---|---|---|---|---|---|
| | Site # | Type | Weight % | QCC | $\eta$ | NQR Frequency (kHz) | FWHM (kHz) | $T_1$ (ms) | $T_2$ (ms) | dv/dT (kHz/° C.) |
| Cocaine Hydrochloride ($C_{17}H_{21}NO_4 \cdot$ HCL) | 1 | amine-$^{14}$N | 4.3 | 1178 | 0.263 | 961 806 | 4 5 | 2000 700 | 0.3 1.5 | −0.004 −0.032 |
| | 2 | $^{35}$Cl | 7.7 | 3800-5060 | — | 2530 | 20 | 57 | 0.15 | — |
| Heroin Hydrochloride ($C_{21}H_{23}NO_5 \cdot$ HCl•H20) | 1 | amine-$^{14}$N | 3.3 | 1080-1440 (at 20° K) | | 1080 (at 20° K) | — | — | — | — |

Illustrative embodiments described herein are not limited to detecting the chemical species described in Table 1. The chemical species presented in Table 1 are presented as non-limiting examples.

Figure 6:
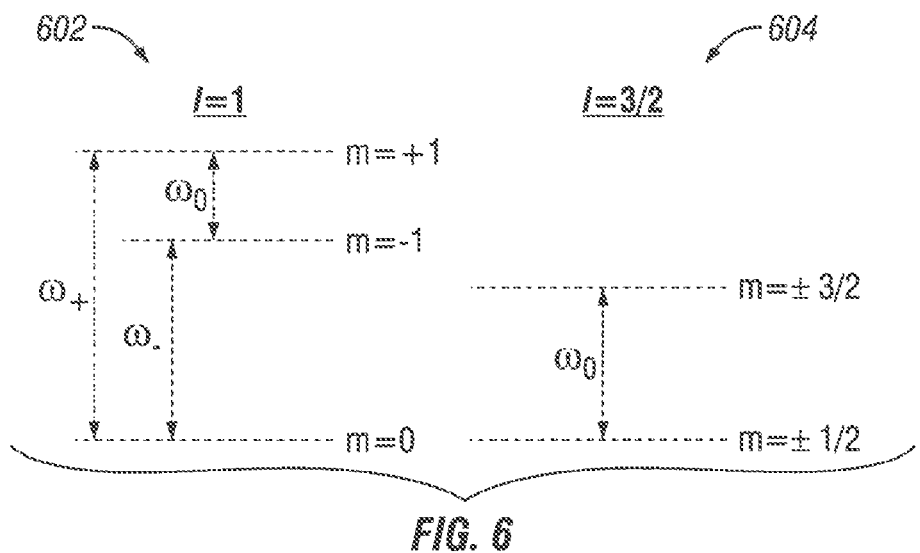
FIG. 6 shows energy levels for I=1 and I=3/2 in accordance with one embodiment of the present disclosure.

Illustrative embodiments of the present disclosure are also directed to determining NQR resonant frequencies of various atomic nuclei within a chemical species. To this end, a Hamiltonian characterizing the quadrupolar interaction of an atomic nucleus can be written in a principal axis system (PAS) of an electric filed gradient (EFG) tensor around the nucleus. Such a Hamiltonian is given by:

$$H_Q = \frac{\omega_Q}{3}\left[3I_z^2 - I(I+1) + \frac{\eta}{2}(I_+^2 + I_-^2)\right]. \quad \text{Eq. 2}$$

where $\omega_Q$ is the NQR coupling constant; $\eta$ is the asymmetry parameter of the EFG tensor $I_x$, $I_y$, and $I_z$ are spin operators; and $I_\pm \equiv I_x \pm iI_y$. A nucleus with spin I has (2I+1) eigenvalues (e.g., energy levels). Each energy level corresponds to a value of m, where m is the secondary (or projection) spin quantum number that runs from {−I, −I+1, . . . +I}. Some of these levels may be degenerate. FIG. 6 shows energy levels for I=1 602 and I=3/2 604 in accordance with one embodiment of the present disclosure. A shown in FIG. 6, for I=1, three distinct transitions can occur between the three levels resulting in a NQR spectrum with three lines. The frequencies of these lines are given by:

$$\omega_\pm = \frac{3\omega_Q}{4}\left(1 \pm \frac{\eta}{3}\right) \quad \text{Eq. 3, Eq. 4}$$

$$\omega_0 = \omega_+ - \omega_- = \frac{\eta\omega_Q}{2},$$

When the EFG is symmetric (e.g., when $\eta=0$), the m=±1 energy levels become degenerate and the three NQR transitions become a single line with a frequency of $3\omega_Q/4$. FIG. 6 also shows that spins with I=3/2 have four energy levels. The ±1/2 and ±3/2 energy levels energy are degenerate in the absence of an external magnetic field. This phenomenon results in a single NQR line with a frequency that can be determined by:

$$\omega_0 = \frac{\omega_Q}{2}\sqrt{1 + \frac{\eta^2}{3}} \quad \text{Eq. 5}$$

NQR transition frequencies for higher spin numbers can be derived using a perturbation approach.

Illustrative embodiments of the present disclosure are also directed to calculating NQR signal amplitude for various atomic nuclei within a chemical species. In various embodiments, NQR signal strengths for various atomic nuclei within a solid sample can be determined by estimating the density of the nuclear spins in the sample with respect to another substance (e.g., water). The density of the spins can be determined by:

$$\rho_s = \frac{f_s N_s N_A \rho}{MW}, \quad \text{Eq. 6}$$

where MW is the molecular weight, $f_s$ is the isotope fraction (abundance) of the nucleus of interest, $N_S$ is the number of nuclear spins of interest per molecule, $\rho$ is the density (specific gravity) of the sample, and $N_A$ is Avogadro's number. Equation 6 can be derived as follows:

$$\rho_s = f_s N_s \times \frac{N_A}{MW} \times \rho \quad \text{Eq. 7}$$

where $f_S N_S$ is the number of spins per cubic centimeter, $N_A/MW$ is the number of molecules per gram, and $\rho$ is the density in grams per cubic centimeter of the sample. Table 2 shows several spin densities for chemical species calculated in accordance with various embodiments of the present disclosure.

TABLE 2

| Compound | Spins per molecule | Natural abundance | Density, $\rho$ (gm/cc) | Molecular weight | Relative density of spins |
|---|---|---|---|---|---|
| Water | 2 ($^1$H) | 99.98% | 1 | 18 | 1 |
| KNO$_3$ (potassium nitrate) | 1 ($^{39}$K) | 93.1% | 2.109 | 101.1 | 0.175 |

TABLE 2-continued

| Compound | Spins per molecule | Natural abundance | Density, ρ (gm/cc) | Molecular weight | Relative density of spins |
|---|---|---|---|---|---|
| $NaNO_2$ (sodium nitrite) | 1 ($^{14}N$) | 99.64% | 2.168 | 69.00 | 0.283 |
| $C_2H_5NO_2$ (glycine) | 1 ($^{14}N$) | 99.64% | 1.607 | 75.07 | 0.193 |
| $C_5H_9NO_2$ (L proline) | 1 ($^{14}N$) | 99.64% | 1.35 | 115.13 | 0.106 |

As shown in Table 2, the chemical species have spin densities that are 10% to 20% of the spin density of water.

As in nuclear magnetic resonance (NMR), a nutation angle of a rectangular pulse of length ($T_p$) can be determined by:

$$\beta = \omega_1 T_p = \gamma B_1 T_p \qquad \text{Eq. 8}$$

where $\omega_1$ is the nutation frequency, $B_1$ is the amplitude of an applied oscillating magnetic field, and $\gamma$ is the gyromagnetic ratio of the atomic nucleus of interest. In contrast to NMR, where magnetization is circularly polarized, in NQR, the magnetization is linearly polarized. For this reason, in NQR, the effective amplitude ($B_1$) of a linearly-polarized oscillating magnetic field is doubled, as compared to NMR (e.g., $B_1 = 2B_{1c}$, where $B_{1c}$ is the amplitude of the circularly-polarized component that is useful for NMR). For similar coil and transmitter currents, nutation angles of pulses in NMR and NQR are given by:

$$\frac{\beta_{NQR}}{\beta_{NMR}} = \frac{\gamma_{NQR} B_1 T_{p,NQR}}{\gamma_{NMR} B_{1c} T_{p,NMR}} \qquad \text{Eq. 9}$$

$$= \frac{\gamma_{NQR}(2B_{1c}) T_{p,NQR}}{\gamma_{NMR} B_{1c} T_{p,NMR}}$$

$$= \frac{2\gamma_{NQR} T_{p,NQR}}{\gamma_{NMR} T_{p,NMR}}$$

$$\Rightarrow \frac{T_{p,NQR}}{T_{p,NMR}} = \left(\frac{\gamma_{NMR}}{2\gamma_{NQR}}\right) \frac{\beta_{NQR}}{\beta_{NMR}}$$

where $\gamma_{NMR}$ is the gyromagnetic ratio of the atomic nucleus of interest with respect to NMR and $\gamma_{NQR}$ is the gyromagnetic ratio of the atomic nucleus of interest with respect to NQR. According to equation 9, to generate similar nutation angles, NQR pulses are ($\gamma_{NMR}/2\gamma_{NQR}$) times as long as NMR pulses. For example, if $\gamma_{NMR}/\gamma_{NQR} \approx 14$, then $^{14}N$ NQR pulses are approximately 7 times as long as proton NMR pulses.

An NMR signal in a homogenous magnetic field varies with the nutation angle as $S(\beta) \propto \sin(\beta)$, where $\beta \equiv \omega_{1c} t$ is the nutation angle and t is the duration of the pulse. By contrast, in NQR, nutation angles vary as a function of the crystal orientation relative to the applied oscillating field ($B_1$). In one specific example, a nominal nutation angle can be defied as $\beta \equiv \omega_1 t$ and a local nutation frequency varies as $\omega_{z1} = \omega_1 \cos(\varphi)$, where $\varphi$ is an angle between applied oscillating field ($B_1$) and a principal axis of an electric field gradient (EFG) tensor (e.g., z-axis). In the specific example described, a local signal amplitude varies as:

$$S(\beta, \phi) = \frac{\omega_{z1} e^{i\psi}}{2} \sin(\omega_{z1} t) = \frac{\omega_1 \cos(\phi) e^{i\psi}}{2} \sin(\beta \cos(\phi)), \qquad \text{Eq. 10}$$

Where the initial $\cos(\varphi)$ factor accounts for a receptivity pattern of a coil being used to apply the oscillating field, $\psi$ is the phase of the pulse, and $\theta$ is an angle between the x-axis and the projection of $B_1$ on the x-y plane. The total NQR signal amplitude can be obtained by summing over the possible values of the angles $\varphi$ and $\theta$. In the case where $\eta \neq 0$, the local signal amplitude varies as:

$$S(\beta) = \frac{1}{4\pi} \int_0^{2\pi} \int_0^{\pi} S(\beta, \phi) d\phi d\theta \qquad \text{Eq. 11}$$

$$= \frac{\omega_1 e^{i\psi}}{8} \int_0^{\pi} \sin(2\phi) \sin(\beta \cos(\phi)) d\phi$$

$$\propto \sqrt{\frac{\pi}{2\beta}} J_{3/2}(\beta),$$

where $J_{3/2}$ is the Bessel function of the first kind and order 3/2. A different relationship occurs in the case where $\eta=0$.

FIG. 7 shows a plot 700 of signal amplitude versus nutation angle in accordance with one embodiment of the disclosure. In particular, FIG. 7 shows NMR 702 and NQR 704 signal amplitudes for the case where $n \neq 0$. The locations of a first NQR signal maximum (0.436 at 119 degrees), zero-crossing (257 degrees), and minimum (−0.168 at 340 degrees) are marked with dashed lines. A maximum NQR signal (corresponding to an optimum excitation pulse) occurs at a nutation angle of approximately 119 degrees and the NQR signal reaches 43.6% of an NMR process at a similar nutation angle. Similarly, a first zero crossing (corresponding to the optimum inversion pulse) occurs at a significantly larger nutation angle (257 degrees) than in an NMR process.

Amplitudes of the maximum nuclear magnetization in NMR and NQR can be determined by:

$$M_{NMR}(\omega_0) = \rho_s \left(\frac{\gamma^2 \hbar^2 I(I+1)}{2kT}\right) B_0, \qquad \text{Eq. 12, Eq. 13}$$

$$= \rho_s \left(\frac{\gamma \hbar^2 \omega_0}{kT}\right)\left(\frac{I(I+1)}{3}\right)$$

$$M_{NQR}(\omega_0) = 0.44 \rho_s \left(\frac{\gamma \hbar^2 \omega_0}{kT}\right)\left(\frac{I(I+1) - mm'}{2I+1}\right),$$

$$|m - m'| = 1.$$

where m and m' are the secondary (or projection) spin quantum numbers of the NQR energy levels between which transitions are detected. These numbers are selected from the set $\{-I, -I+1, \ldots +I\}$ with (2I+1) elements. Unlike in NMR, the restriction |m−m'|=1 is not fundamental, and similar expressions can be derived for NQR signals for which |m−m|≠1. The factor of 0.44 is obtained from the sample average, as shown in FIG. 6 (e.g., 0.436 at 119 degrees). As shown in equation 13, NQR signal intensity at a given frequency is proportional to the gyromagnetic ratio of the atomic nucleus of interest ($\gamma$).

Table 3 shows nuclear magnetizations for several chemical species calculated in accordance with various embodiments of the present disclosure. In particular, Table 3 shows calculated nuclear magnetizations for several chemical species for NQR measurements as compared to a calculated nuclear magnetization for water for an NMR measurement. The frequency across measurements was kept constant. With respect to potassium nitrate, the 3/2→1/2 transition was used to determine the values within Table 3.

TABLE 3

| Compound | Experiment | Relative spin density | Spin quantum number | Relative nuclear magnetization |
|---|---|---|---|---|
| Water | 1H NMR | 1 | 1/2 | 100% |
| $KNO_3$ (potassium nitrate) | $^{39}K$ NQR | 0.175 | 3/2 | 1.07% |
| $NaNO_2$ (sodium nitrite) | $^{14}N$ NQR | 0.283 | 1 | 2.38% |
| $C_2H_5NO_2$ (glycine) | $^{14}N$ NQR | 0.193 | 1 | 1.62% |
| $C_5H_9NO_2$ (proline) | $^{14}N$ NQR | 0.106 | 1 | 0.89% |

Table 3 shows that the volumetric sensitivity of NQR is low. Signal strengths corresponding to an effective water-filled NMR porosity of 1% to 2% are expected for common compounds. In various embodiments, an active volume of the measurement is large to compensate for the low intrinsic sensitivity of the NQR measurement. In some embodiments, NQR measurements are performed without a static magnetic field. If this is the case, an active volume of the measurement may be limited by the inhomogeneous nature of the oscillating magnetic field.

Figure 8:
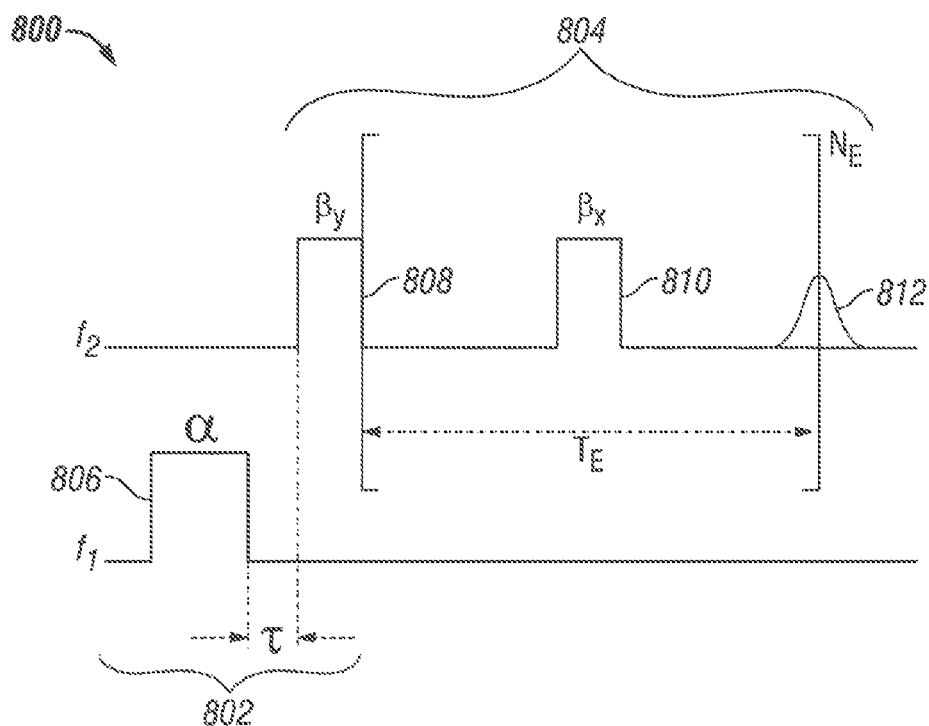
FIG. 8 shows an NQR perturbation-detect sequence in accordance with one embodiment of the present disclosure.

Illustrative embodiments of the present disclosure are also directed to NQR pulse sequences that include perturbation segments for improving the accuracy of NQR measurements and determinations. FIG. 8 shows an NQR perturbation-detect sequence 800 in accordance with one embodiment of the present disclosure. The perturbation-detect sequence includes a perturbation segment 802 followed by a detect segment 804. The perturbation segment 802 is applied at a first frequency ($f_1$) and the detect segment 804 is applied at a second frequency ($f_2$). The first frequency is selected to match a known resonant frequency of a set of atomic nuclei at a site within a chemical species (e.g., 737 kHz for glycine), while the second frequency is selected to match a known resonant frequency of the set of atomic nuclei at the same site within the chemical species (e.g., 1052 kHz for glycine). In the specific example of FIG. 8, the perturbation segment 802 includes a single pulse 806 with a nutation angle of α. In some embodiments, the nutation angle can vary between 90 degrees and 180 degrees. The detect segment 804 includes an excitation pulse 808 followed by a number ($N_E$) of refocusing pulses and corresponding echoes 812. In specific embodiments, the detect segment 804 is one of an SLSE or SSFP pulse sequence as described above. A time interval of τ is located between the perturbation segment 802 and the detect segment 804. In one example, the time interval is selected to avoid relaxation of the atomic nuclei of interest. In a specific example, the time interval is selected to be less than or equal to the product of (1) the $T_1$ relaxation time of the atomic nuclei of interest and (2) the frequency of the perturbation segment ($f_1$) 802 (e.g., τ=$T_1$ ($f_1$)).

Figure 9:
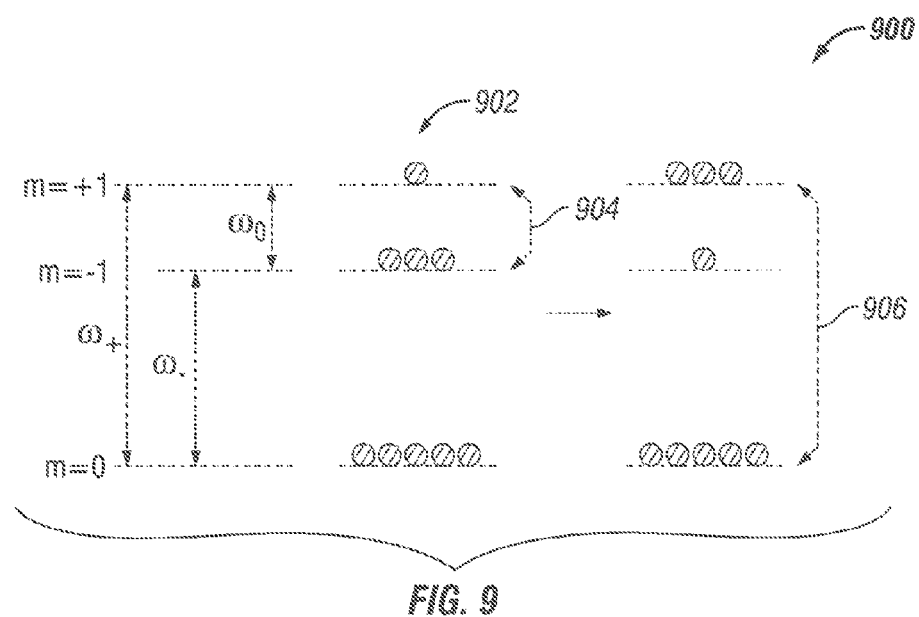
FIG. 9 shows an energy-level diagram for atomic nuclei with a spin quantum number equal to 1 in accordance with one embodiment of the present disclosure.

In various embodiments of the present disclosure, such an NQR perturbation-detect sequence 800 can improve the accuracy of NQR measurements and determinations by modulating the energy levels of atomic nuclei at a particular site within a chemical species. FIG. 9 shows an energy-level diagram 900 in accordance with one embodiment of the present disclosure. In particular, the energy-level diagram 900 represents energy states for atomic nuclei with a spin quantum number equal to 1. For this reason, the energy level diagram includes NQR lines for I=+1, −1, and 0. At thermal equilibrium 902, each energy level includes a certain population of atomic nuclei. The frequency of the perturbation segment ($f_1$) 904 is selected to match a known resonant frequency ($\omega_0$) of atomic nuclei within two energy levels. When this perturbation segment 904 is applied to the substance, the atomic nuclei within lines +1 and −1 switch energy states. As a result, the populations between lines +1 and −1 are inverted before a detect segment 906 is applied. The detect segment ($f_2$) 906 is selected to match another known resonant frequency ($\omega_+$) of the atomic nuclei. The resonant signal generated by the perturbation segment 904 and the detect segment 906 are detected by the NQR system. As shown in FIG. 9, the perturbation segment 904 causes a change within the population of line +1. In particular, the population of line +1 is now increased to three atomic nuclei. This change in population is detected by applying the detect segment 906 to the substance and detecting a resonant signal with decreased amplitude. The signal has decreased amplitude because the difference between populations between line +1 and line 0 is smaller, as compared with the difference at thermal equilibrium 902. In this manner, various embodiments of the present disclosure can detect the presence of one NQR transition (e.g., at $f_1$) by observing signals produced by another transition (e.g., at $f_2$).

Figure 10:
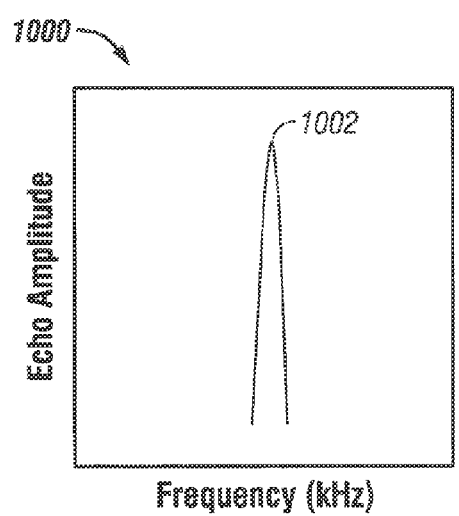
FIG. 10 shows a first peak in a detected resonant signal in accordance with one embodiment of the present disclosure.
Figure 11:
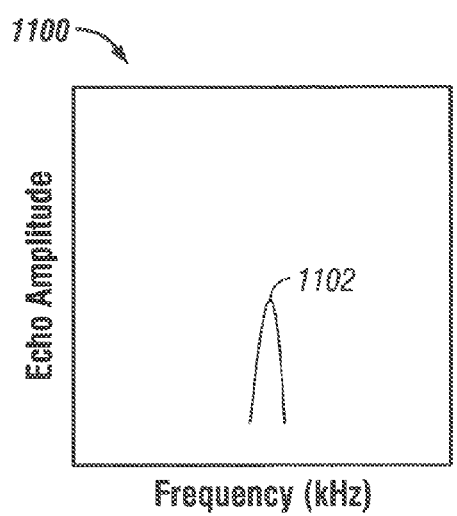
FIG. 11 shows a second peak in a detected resonant signal in accordance with one embodiment of the present disclosure.

In exemplary embodiments of the present disclosure, such NQR perturbation-detect sequences can be used with other NQR sequences to improve the accuracy of NQR measurements and determinations by confirming the presence of a particular atomic nuclei of interest. In one illustrative embodiment, a reference NQR pulse sequence, such as an SLSE sequence, is applied to a substance with a frequency ($f_1$). The frequency ($f_1$) is selected to match a known resonant frequency ($\omega_0$) of a set of atomic nuclei of interest within a chemical species. A reference resonant signal produced by the reference sequence is detected. FIG. 10 shows a plot 1000 of echo amplitude versus frequency in accordance with one embodiment of the present disclosure. The plot 1000 shows a first peak 1002 within the detected resonant signal for the reference NQR pulse sequence. A second NQR pulse sequence is applied to the substance. In an exemplary embodiment, the second NQR pulse sequence is a perturbation-detect sequence as shown in for example FIG. 8. The frequency of the perturbation segment ($f_1$) is selected to match a known resonant frequency ($\omega_0$) of the set of atomic nuclei and the detect segment ($f_2$) is selected to match another known resonant frequency ($\omega_+$) of the atomic nuclei. The resonant signal generated by the perturbation segment and the detect segment are detected by the NQR system. FIG. 11 shows a plot 1100 of echo amplitude versus frequency in accordance with one embodiment of the present disclosure. The plot 1100 shows a second peak 1102 within the detected resonant signal for the NQR perturbation-detect sequence. As compared with FIG. 10, the amplitude for the second peak 1102 is smaller than the first peak 1102 produced by the reference sequence. This decrease in amplitude confirms that the first peak 1002 is representative of the set of atomic nuclei of interest within the particular chemical species. If the first peak 1002 was generated by outside noise and/or by a different chemical species within the substance, then there would likely be no change in the amplitude of the first peak. In this manner, such exemplary embodiments can reduce false-positives and can more accurately identify specific chemical species, such as TNT and RDX within the substance.

In one example, outside noise can come from radio stations. Many NQR lines lie within the broadcast AM band (e.g., 540 kHz to 1.7 MHz). As a result RF interference (RFI) from remote radio stations is common in NQR systems. In addition, internal sources of RFI, such as piezoelectric and magneto-acoustic ringing, contribute to noise and false-positives.

Illustrative embodiments of the present disclosure are not limited to selecting $\omega_0$ as the first frequency ($f_1$) and $\omega_+$ as the second frequency ($f_2$). Many different combinations of known resonant frequencies (e.g., $\omega_0$, $\omega_+$, and $\omega_-$) can be selected to achieve similar results. For example, in some cases, the resonant frequencies can be selected in a manner so that the amplitude produced by the resonant signal increases as compared with reference resonant signal. To this end, Table 4 below shows amplitude changes for various known resonant frequencies.

TABLE 4

|  | $f_2 = \omega_+$ | $f_2 = \omega_-$ | $f_2 = \omega_0$ |
|---|---|---|---|
| $f_1 = \omega_+$ |  | Decrease | Decrease |
| $f_1 = \omega_-$ | Decrease |  | Increase |
| $f_1 = \omega_0$ | Decrease | Increase |  |

FIGS. 12-26 and 30 show various plots in accordance with embodiments of the present disclosure. These plots were determined using broadband NQR electronics in accordance with various embodiments of the present disclosure. Acquired data points from the NQR electronics were integrated using either a rectangular or Hamming weighting function to obtain the amplitude of each echo. The echoes were added together to increase SNR.

Figure 12:
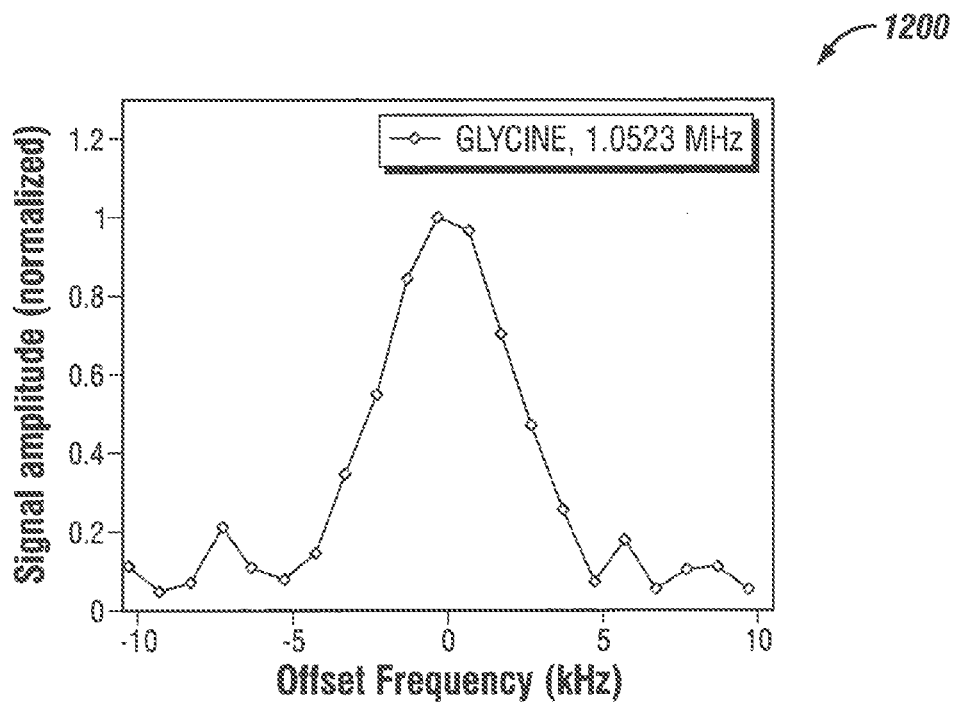
FIG. 12 show a plot of NQR signal amplitude versus frequency offset for an $^{14}$N NQR spectral line for an SLSE pulse sequence applied to a sample of glycine in accordance with one embodiment of the present disclosure.

FIG. 12 shows a plot 1200 of NQR signal amplitude versus frequency offset in accordance with one embodiment of the present disclosure. More specifically, FIG. 12 shows an $^{14}$N NQR spectral line for an SLSE pulse sequence applied to a sample of glycine at 1052 kHz (e.g., $\Delta f=0$ at 1052 kHz). The sequence parameters for FIG. 12 include N=32, $T_E$=800 ms, $N_E$=60, $T_p$=170 µs, and $T_R$=0.4 s, where N is the number of times the sequences are repeated, $T_E$ is the echo spacing, $N_E$ is the number of refocusing pulses and corresponding echoes, $T_p$ is the refocusing pulse length, and $T_R$ is the time between repetitions of the sequences.

Figure 13:
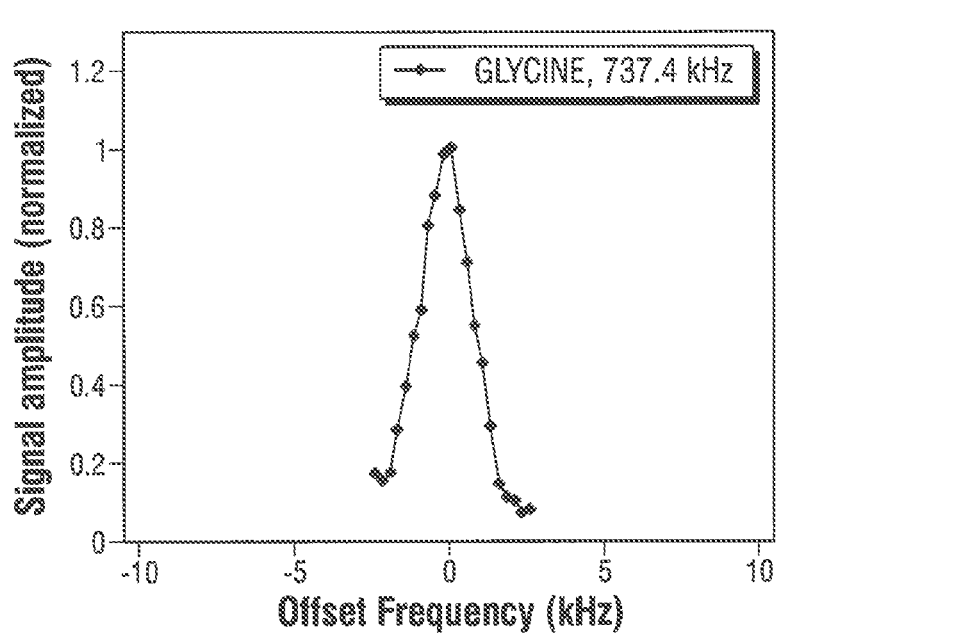
FIG. 13 shows a plot of NQR signal amplitude versus frequency offset for another $^{14}$N NQR spectral line for an SLSE pulse sequence applied to a sample of glycine in accordance with one embodiment of the present disclosure.

FIG. 13 show a plot 1300 of NQR signal amplitude versus frequency offset amplitude in accordance with another embodiment of the present disclosure. More specifically, FIG. 13 shows $^{14}$N NQR spectral lines for an SLSE pulse sequence applied to a sample of glycine at 737 kHz (e.g., $\Delta f=0$ at 737 kHz). For FIG. 13, the sequence parameters include N=32, $T_E$=1350 ms, $N_E$=50, $T_p$=120 µs, and $T_R$=0.4 s.

FIGS. 12 and 13 were obtained using broadband NQR electronics. The Figures show that broadband NMR electronics can be used to apply pulse sequence segments at different frequencies to different spectral lines within the same chemical species.

Figure 14:
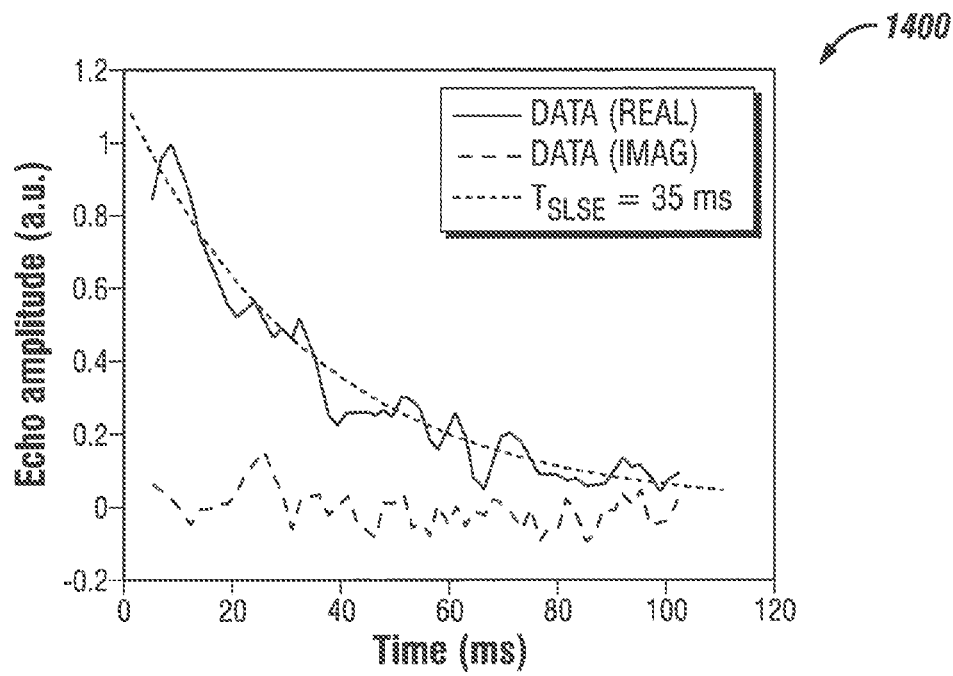
FIG. 14 shows measured decay for an SLSE sequence applied to a glycine sample at a spectral line in accordance with one embodiment of the present disclosure.

FIG. 14 shows a plot 1400 of echo amplitude versus time in accordance with one embodiment of the present disclosure. In particular, FIG. 14 shows a measured decay for an SLSE sequence applied to a glycine sample at 1052 kHz. The measurement was performed in the presence of a small external static magnetic field of magnitude 13 G. The sequence parameters for FIG. 14 include N=4096, $T_E$=1.7 ms, $N_E$=60, $T_p$=700 µs ($\beta\approx$120 degrees), and $T_R$=200 ms.

Figure 15:
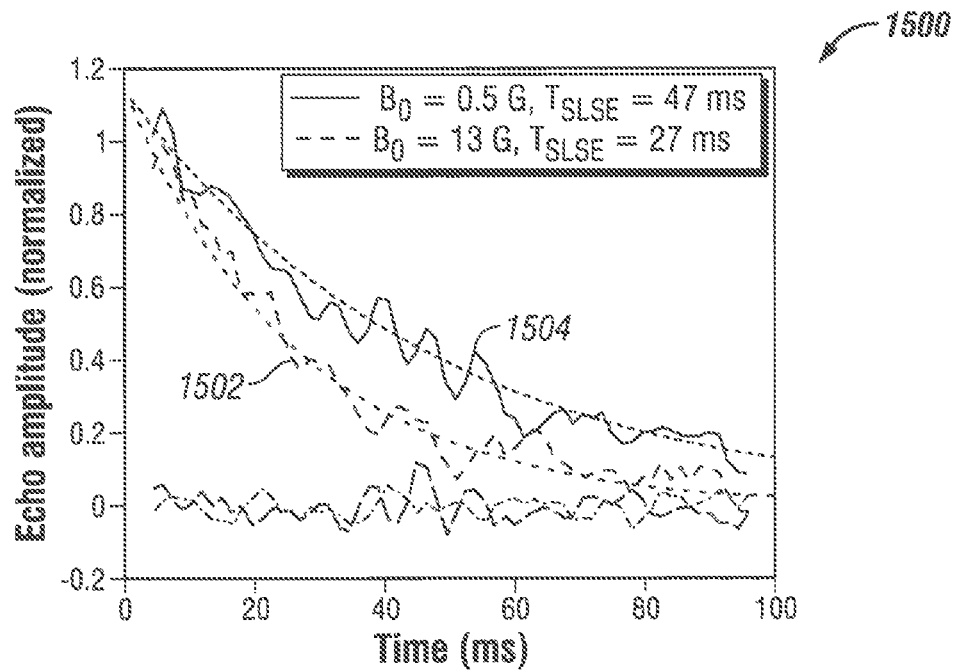
FIG. 15 shows measured decay for an SLSE sequence applied to a glycine at another spectral line in accordance with another embodiment of the present disclosure.

FIG. 15 shows a plot 1500 of echo amplitude versus time in accordance with another embodiment of the present disclosure. In particular, FIG. 15 shows measured decay for an SLSE sequence applied to a glycine sample at 737 kHz in the presence of a small external static magnetic field of magnitude 13 G (1502) and without a static magnetic field (e.g., the remaining 0.5 G comes from the earth's field) (1504). The relaxation rate increases noticeably in the presence of the applied static field. In some cases, this effect is caused by Zeeman broadening of the NQR line in the applied field. The result is a decrease in the values of $T_2$ and the $T_2/T_E$ ratio, which in turn causes $T_{SLSE}$ to decrease. The sequence parameters for FIG. 15 include N=512, $T_E$=1.5 ms, $N_E$=20, $T_p$=480 µs ($\beta\approx$120 degrees), and $T_R$=200 ms.

Figure 16:
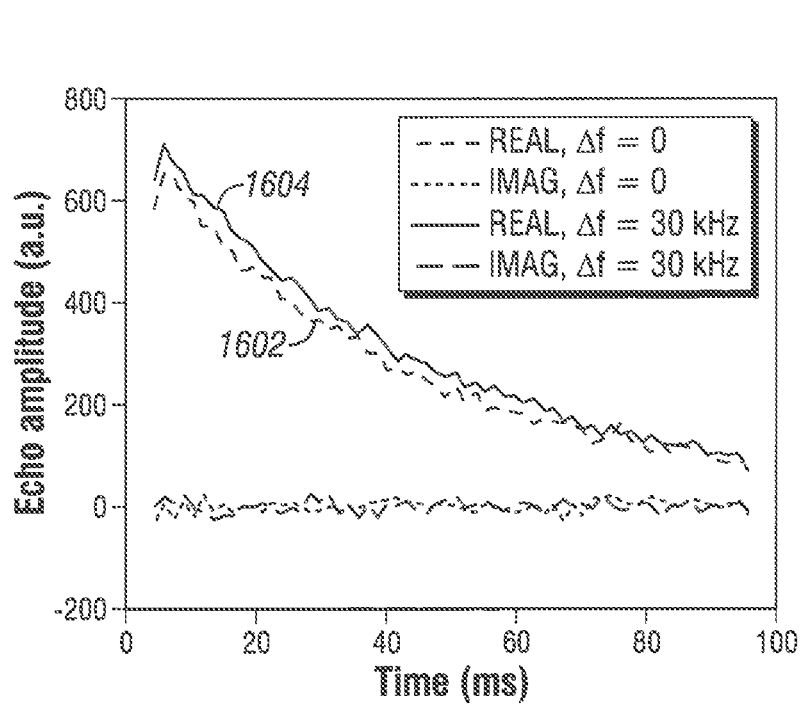
FIG. 16 shows measured decays for a perturbation-detect sequence applied to a glycine sample in accordance with one embodiment of the present disclosure.

FIG. 16 shows a plot 1600 of echo amplitude versus time in accordance with one embodiment of the present disclosure. In particular, FIG. 16 shows measured decays for a perturbation-detect sequence applied to a glycine sample. The perturbation-detect sequence included a perturbation segment and a detect segment. The perturbation segment included one pulse applied at 1052 kHz and the detect segment included an SLSE sequence applied at 737 kHz. The 737 kHz frequency in glycine corresponds to $\omega_-$, while the 1052 kHz frequency corresponds to $\omega_+$. The signal amplitude decreases by approximately 8% when the inversion pulse is resonant with the $\omega_+$ transition ($\Delta f=0$) (1602), relative to its value when the initial pulse is far-off resonance ($\Delta f=30$ kHz) (1604). This decrease in signal amplitude conforms to the amplitude changes listed in Table 4. The nutation angle of the inversion pulse was set to $\alpha=340$ degrees. Other sequence parameters include N=1024, $T_E$=1.5 ms, $N_E$=64, $T_p$=480 µs (($\beta\approx$120 degrees), and $T_R$=200 ms.

Figure 17:
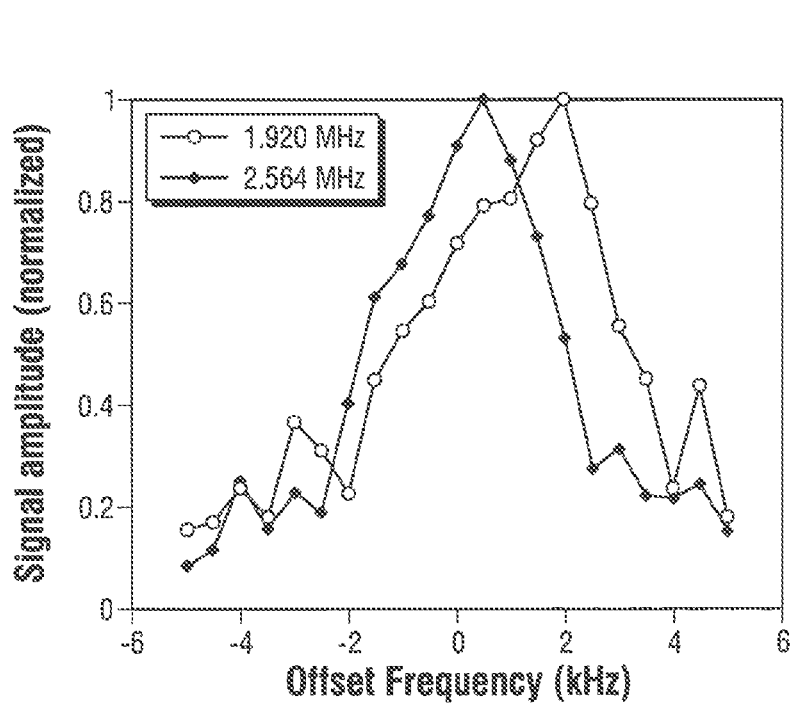
FIG. 17 shows a plot of NQR signal amplitude produced by an NQR pulse sequence applied to a sample of paracetamol in accordance with one embodiment of the present disclosure.

FIG. 17 shows a plot 1700 of echo amplitude versus frequency offset in accordance with one embodiment of the present disclosure. In particular, FIG. 17 shows measured NQR signal amplitude produced by an NQR pulse sequence applied to a sample of paracetamol (e.g., also known as acetaminophen or Tylenol™). The sample contained 100 capsules of paracetamol and each capsule contained 650 mg of the paracetamol. Two NQR signals of this compound (at 1921 kHz and at 2564 kHz) were measured and detected. Detection of multiple resonances makes chemical identification more robust in the presence of noise and external interference. The sequence parameters for FIG. 17 include N=4, $T_E$=1000 µs/1100 µs, $N_E$=1000, $T_p$=320 µs/420 µs, and $T_R$=16 s/19 s.

Figure 18:
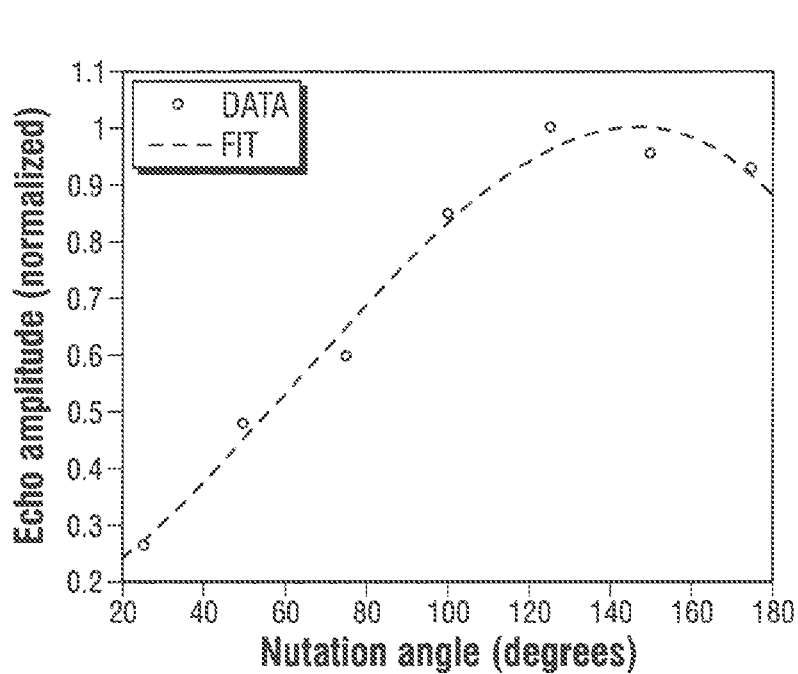
FIG. 18 shows a measured nutation curve of for an SLSE sequence applied to a glycine sample in accordance with one embodiment of the present disclosure.

FIG. 18 shows a plot 1800 of echo amplitude versus nutation angle in accordance with one embodiment of the present disclosure. In particular, FIG. 18 shows a measured nutation curve of for an SLSE sequence applied to a glycine sample at 737 kHz. The plot was obtained by varying the pulse lengths (e.g., nutation angles) of an SLSE sequence. The measured curve matches the curve shown in FIG. 7. In particular, the maximum signal amplitude occurs for $\beta\approx$120 degrees. Sequence parameters for FIG. 18 include N=1024, $T_E$=1.5 ms, $N_E$=20, $T_p$=100 µs-700 µs (($\beta\approx$24 degrees to 168 degrees), and $T_R$=200 ms.

Figure 19:
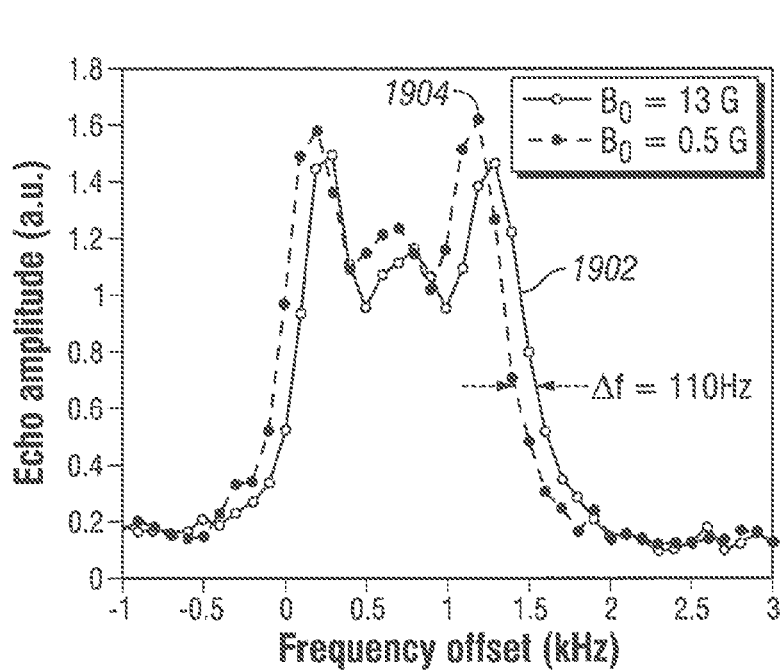
FIG. 19 shows a measured $^{14}$N NQR spectral line for an SLSE pulse sequence applied to a sodium nitrite sample in accordance with one embodiment of the present disclosure.

FIG. 19 shows a plot 1900 of echo amplitude versus frequency offset in accordance with one embodiment of the present disclosure. In particular, FIG. 19 shows a measured $^{14}$N NQR spectral line for an SLSE pulse sequence applied to a sodium nitrite sample at 1038 kHz (e.g., $\Delta f=0$ at 1038 kHz). The figure shows data taken with 1902 and without 1904 a weak external static magnetic field (e.g., approximate magnitude of 13 G). The two line shapes are very similar. Removing the external field causes an overall downward frequency shift of approximately 110 Hz. This shift is caused by a change in temperature. The temperature coefficient of the 1038 kHz line as shown in Table 1 is −0.4 kHz/° C. The measurement is consistent with a 0.25° C. change in sample temperature between the two measurements. FIG. 19 also shows that the shape of the NQR line is complex and contains three peaks. The two outer peaks are the largest. They have almost equal amplitudes and a frequency separation (e.g., splitting) of approximately 1.1 kHz. This behavior may be caused by off-resonant spin dynamics in the SLSE sequence. This conclusion is supported by the fact that the splitting between neighboring peaks is approximately $1/T_E$. The SLSE sequence parameters for FIG. 19 include N=64, $T_E$=1.7 ms, $N_E$=100, $T_p$=700 µs (($\beta \approx$120 degrees), and $T_R$=1 second.

Figure 20:
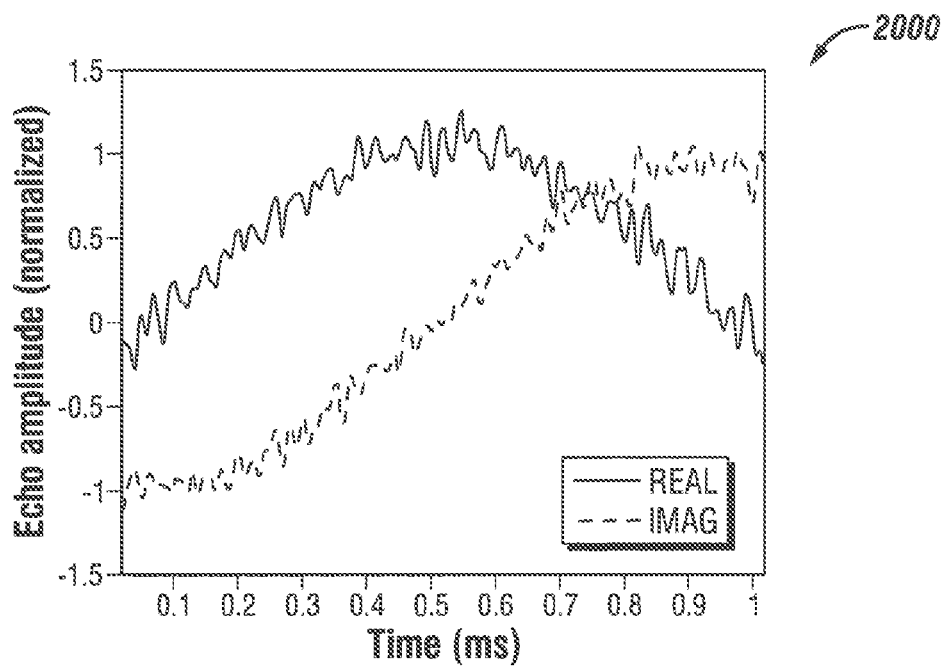
FIG. 20 shows a measured asymptotic time-domain echo shape for an SLSE sequence applied to a sodium nitrite sample in accordance with one embodiment of the present disclosure.

FIG. 20 shows a plot 2000 of echo amplitude versus time in accordance with one embodiment of the present disclosure. In particular, FIG. 20 shows a measured asymptotic time-domain echo shape for an SLSE sequence applied to a sodium nitrite sample at 1038 kHz. The echo is broad, which indicates a narrow NQR line width. The curve shape is sinusoidal with a frequency of approximately 500 Hz. This value matches the frequency offset between the excitation frequency of 1038.25 kHz and the center of the sodium nitrite line, which, as shown in FIG. 19, is approximately 1038.75 kHz. Sequence parameters for FIG. 20 include N=512, $T_E$=2.2 ms, $N_E$=75, $T_p$=700 µs ($\beta \approx$120 degrees), and $T_R$=1 second.

Figure 21:
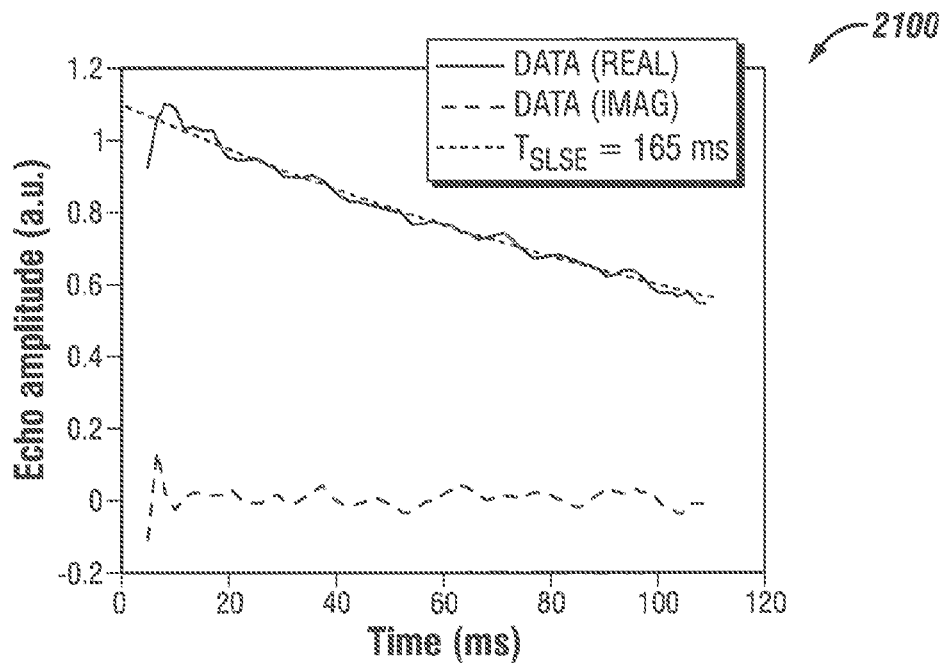
FIG. 21 shows a plot of echo amplitude versus time in accordance with one embodiment of the present disclosure.

FIG. 21 shows a plot 2100 of echo amplitude versus time in accordance with one embodiment of the present disclosure. In particular, FIG. 21 shows measured echo decay for an SLSE sequence applied to a sodium nitrite sample at 1038.25 kHz. The decay, after an initial transient, is closely approximated by an exponential with a decay constant of 165 ms. This value is much larger than $T_2$, which for this transition is approximately 5.1 ms. Sequence parameters for FIG. 21 include N=1024, $T_E$=1.7 ms, $N_E$=64, $T_p$=700 µs (($\beta \approx$120 degrees), and $T_R$=1 second.

Figure 22:
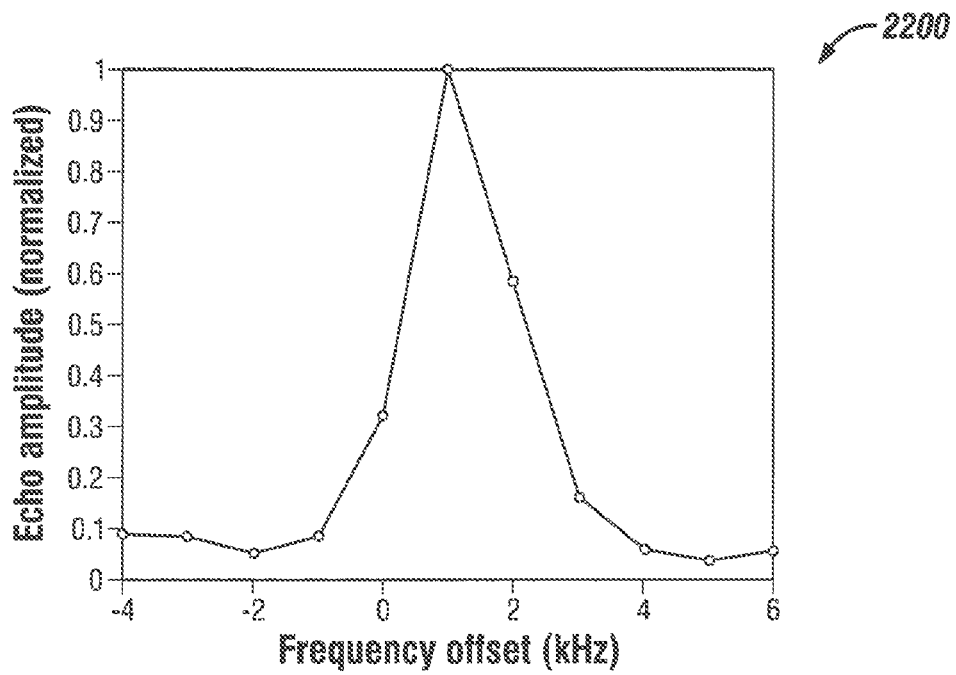
FIG. 22 shows measured echo decay for an SLSE sequence applied to a sodium nitrite sample in accordance with one embodiment of the present disclosure.

FIG. 22 shows a plot 2200 of echo amplitude versus time in accordance with one embodiment of the present disclosure. In particular, FIG. 22 shows a measured $^{39}$K NQR line for an SLSE pulse sequence applied to a potassium nitrate sample at 665 kHz (e.g., $\Delta f$=0 at 665 kHz). The frequency of the spectral line is shifted upward from the tabulated value of 1 kHz because the sample temperature was approximately 2° C. lower than the value at which the tabulated data was collected (e.g., 25° C.). Sequence parameters for FIG. 22 include N=128, $T_E$=2.0 ms, $N_E$=300, $T_p$=500 µs ($\beta \approx$90 degrees), and $T_R$=6 sec.

Figure 23:
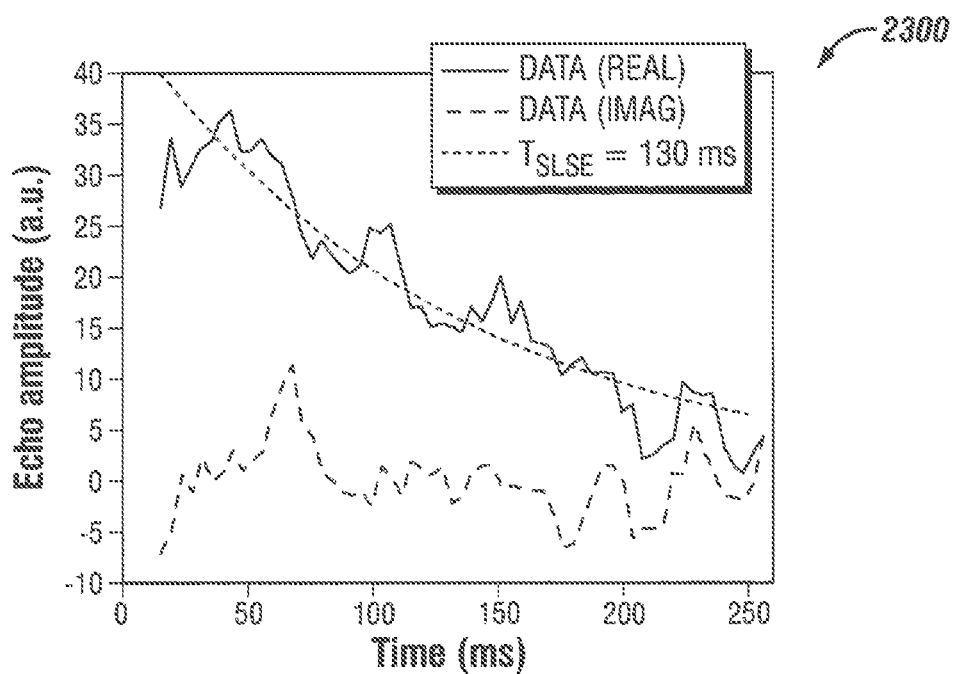
FIG. 23 shows measured echo decay for an SLSE pulse sequence applied to a potassium nitrate sample in accordance with one embodiment of the present disclosure.

FIG. 23 shows a plot 2300 of echo amplitude versus time in accordance with one embodiment of the present disclosure. In particular, FIG. 23 shows measured echo decay for an SLSE pulse sequence applied to a potassium nitrate at 666 kHz. Sequence parameters for FIG. 23 include N=1024, $T_E$=4 ms, $N_E$=64, $T_p$=600 µs ($\beta \approx$108 degrees), and $T_R$=6 seconds.

Figure 24:
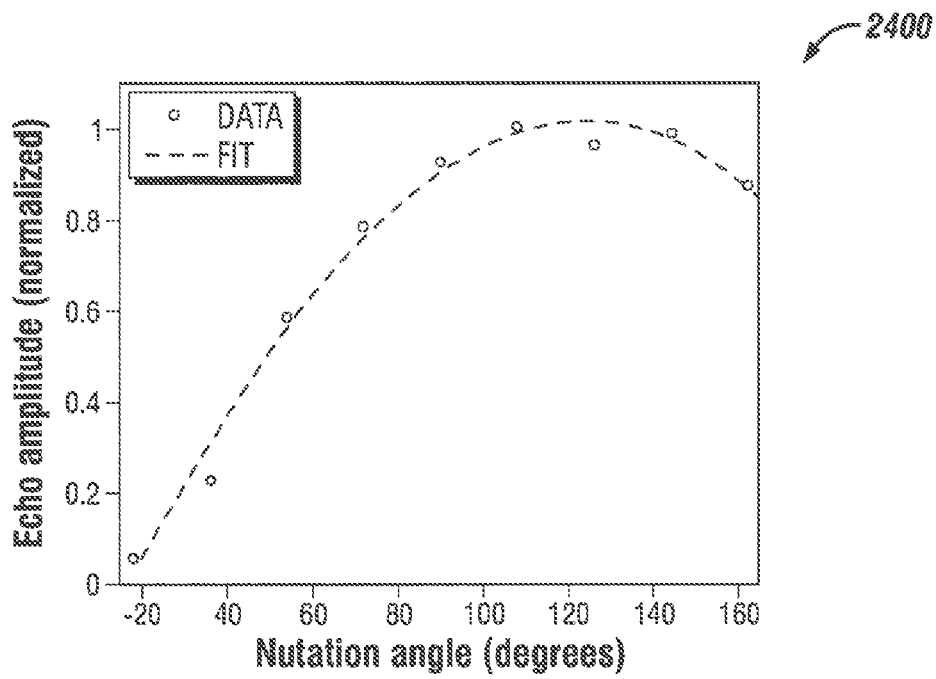
FIG. 24 shows a measured nutation curve for an SLSE sequence applied to a potassium nitrate sample in accordance with one embodiment of the present disclosure.

FIG. 24 shows a plot 2400 of echo amplitude versus nutation angle in accordance with one embodiment of the present disclosure. In particular, FIG. 24 shows a measured nutation curve for an SLSE sequence applied to a potassium nitrate sample at 666 kHz. This plot 2400 was obtained by varying the pulse lengths (e.g. nutation angles) of the SLSE sequence. The measured curve matches the curve shown in FIG. 7. In particular, the maximum signal amplitude occurs for $\beta \approx$120 degrees. The pulse lengths corresponding to these nutation angles are significantly different from those expected for $^{14}$N, which shows that sequence is manipulating $^{39}$K, and not $^{14}$N. Sequence parameters for FIG. 18 include N=1024, $T_E$=2.3 ms, $N_E$=300, $T_p$=100 µs-900 µs ($\beta \approx$18 degrees to 162 degrees), and $T_R$=6 seconds.

Figure 25:
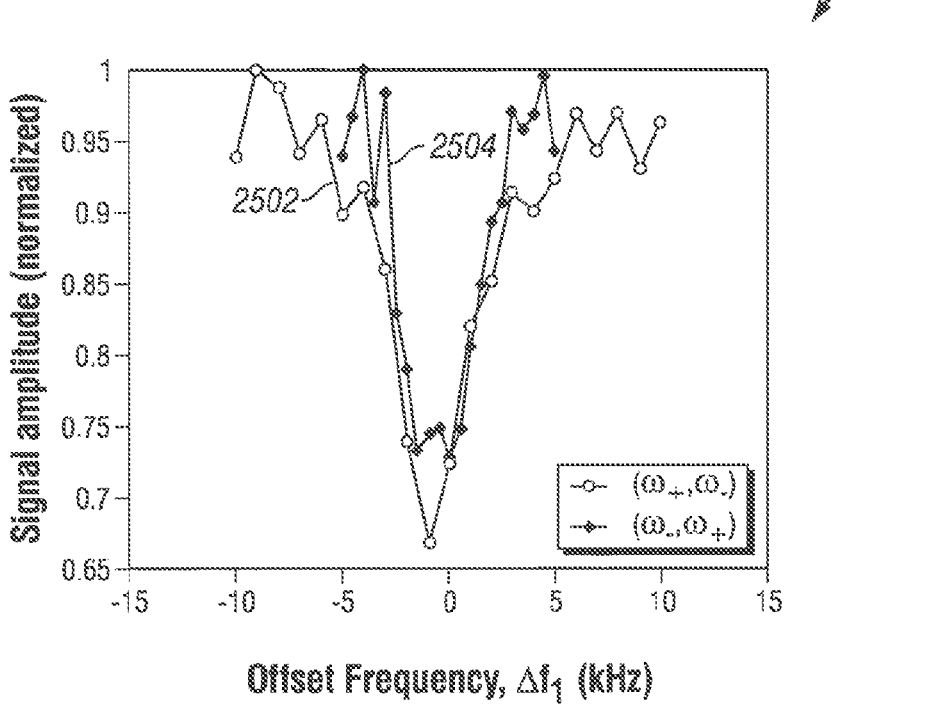
FIG. 25 shows a set of $^{14}$N NQR spectral lines for perturbation-detect pulse sequences applied to a sample of glycine in accordance with one embodiment of the present disclosure.

FIG. 25 show a plot of normalized echo amplitude versus frequency offset in accordance with one embodiment of the present disclosure. More specifically, FIG. 25 shows $^{14}$N NQR spectral lines for perturbation-detect pulse sequences applied to a sample of glycine (e.g., $\omega_+/2\pi$=1052 kHz, $\omega_-/2\pi$=737 kHz, and $\omega_0/2\pi$=315 kHz). The perturbation-detect sequence included a perturbation segment and a detect segment. For the first line 2502, the perturbation segment included one pulse applied at 1052 kHz ($\omega_+$) and the detect segment included an SLSE sequence applied at 737 kHz ($\omega_-$). For the second line 2504, the perturbation segment included one pulse applied at 737 kHz ($\omega_-$) and the detect segment included an SLSE sequence applied at 1052 kHz ($\omega_+$). In both cases, the amplitude of the NQR signal decreases. These decreases in signal amplitude conform to the amplitude changes listed in Table 4. Sequence parameters for FIG. 25 include N=128, $T_E$=760 µs/800 µs, $N_E$=70, $T_p$=360 µs/260 µs for initial pulse and 120 µs/170 µs for later pulses, and $T_R$=0.4 seconds. Echo amplitude has been normalized to echo amplitudes produced by an SLSE sequence without a perturbation segment.

Figure 26:
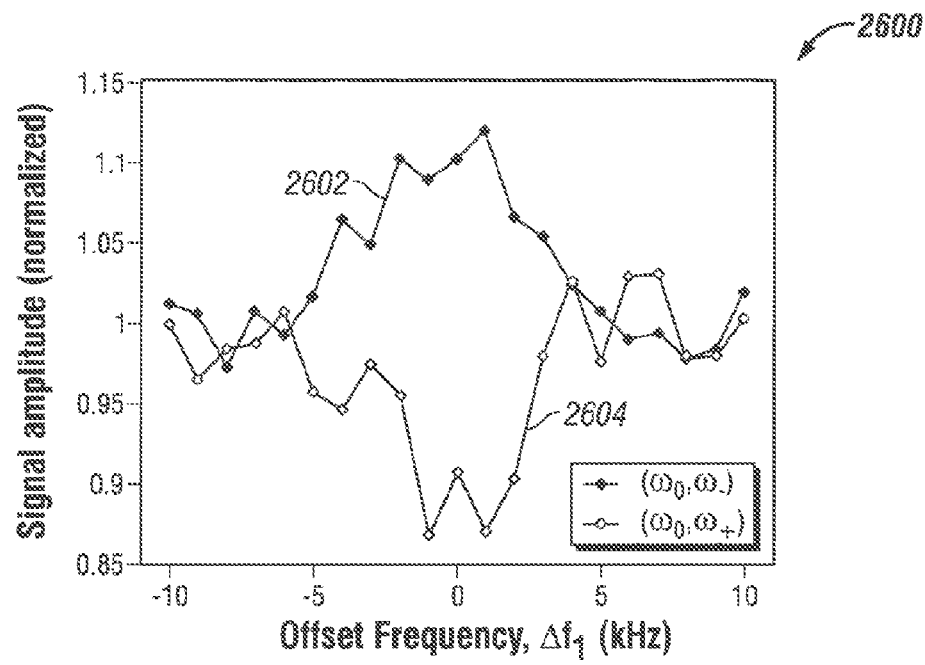
FIG. 26 shows another set of $^{14}$N NQR spectral lines for perturbation-detect pulse sequences applied to the sample of glycine in accordance with one embodiment of the present disclosure.

FIG. 26 show a plot of normalized echo amplitude versus frequency offset in accordance with another embodiment of the present disclosure. More specifically, FIG. 26 shows more $^{14}$N NQR spectral lines for perturbation-detect pulse sequences applied to the sample of glycine (e.g., $\omega_+/2\pi$=1052 kHz, $\omega_-/2\pi$=737 kHz, and $\omega_0/2\pi$=315 kHz). In this case, for the first line 2602, the perturbation segment included one pulse applied at 315 kHz ($\omega_0$) and the detect segment included an SLSE sequence applied at 737 kHz ($\omega_-$). For the second line 2504, the perturbation segment included one pulse applied at 315 kHz ($\omega_0$) and the detect segment included an SLSE sequence applied at 1052 kHz ($\omega_+$). In the first case 2602, the amplitude of the NQR signal increases, while in the second case 2604, the NQR signal decreases. These changes in signal amplitude again conform to the amplitude changes listed in Table 4. Sequence parameters for FIG. 26 include N=256, $T_E$=800 µs/850 µs, $N_E$=70/65, $T_p$=150 µs for initial pulse and 160 µs/225 µs for later pulses, and $T_R$=0.4 seconds. Echo amplitude has been normalized to echo amplitudes produced by an SLSE sequence without a perturbation segment.

Figure 27:
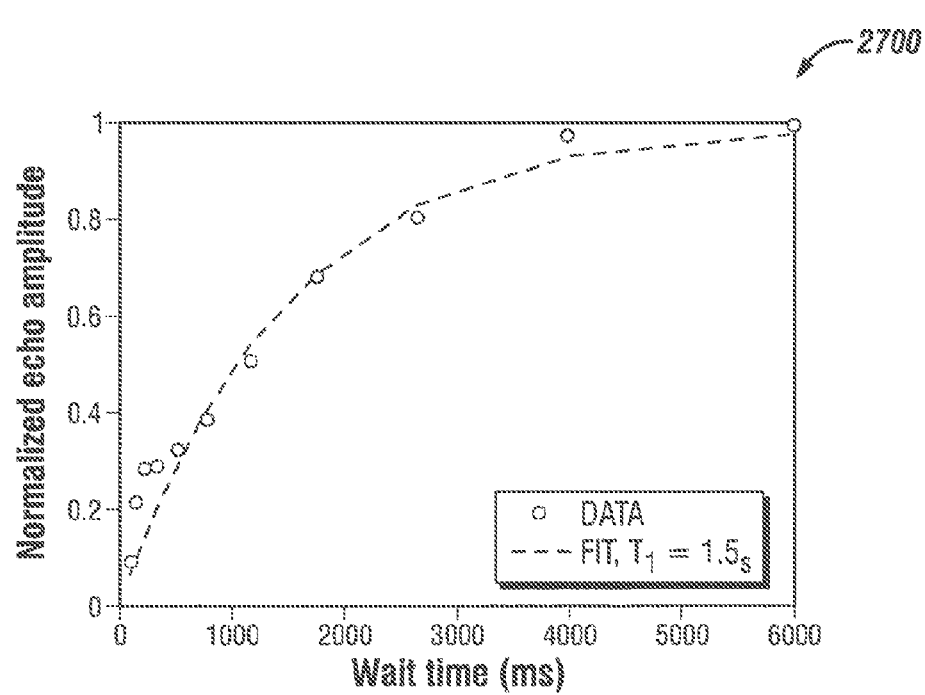
FIG. 27 shows measured results produced by a saturation recovery sequence applied to a sample of L-proline in accordance with one embodiment of the present disclosure.

Various embodiments of the present disclosure are also directed to using an inversion and saturation recovery sequences for measuring a longitudinal relaxation time constant (e.g., $T_1$). FIG. 27 shows a plot 2700 of normalized echo amplitude versus wait time in accordance with one embodiment of the present disclosure. In particular, FIG. 27 shows measured results produced by a saturation recovery sequence applied to the $\omega_0$ transition (e.g., $\omega_0/2\pi$=729 kHz) for L-proline. In one specific example, the $\omega_0$ transition is first saturated by using an SLSE sequence. The magnetization that appears after a variable wait time ($T_W$) is then measured during the next repetition by using the same SLSE sequence. The spin-locked echoes are added together to increase the SNR. The measured SLSE amplitude is then fitted to a saturation-recovery function to extract the value of $T_1$. An example of one such saturation-recovery function is given by:

$$M(T_W) = M_0(1-\exp(-T_W/T_1)) \qquad \text{Eq. 14}$$

where M is signal and $M_0$ is signal obtained when the wait time ($T_W$) is very long (e.g., $T_W > 5T_1$). Using equation 14 in the example of FIG. 27, $T_1$ is determined to be 1.5 seconds, which is similar to the tabulated value of 1.4 seconds for the $\omega_0$ transition as shown in Table 1. Sequence parameters for FIG. 29 include N=512, $T_E$=2 ms, $N_E$=60, and $T_p$=480 µs ($\beta \approx 108$ degrees).

Illustrative embodiments of the present disclosure are directed to systems and methods for applying NQR sequences to a substance that improve the efficiency of NQR measurements. To this end, various embodiments apply an NQR pulse sequence with multiple pulse sequence segments. The multi-segment sequence includes at least a first pulse sequence segment and a second pulse sequence segment. The pulse sequence segments are applied to the substance at different frequencies and generate resonant signals in a first set of atomic nuclei and a second set of atomic nuclei. The second pulse sequence segment is initiated before the first set of atomic nuclei reach thermal equilibrium. In this manner, various embodiments of the present disclosure reduce idle time between NQR measurements.

Figure 28:
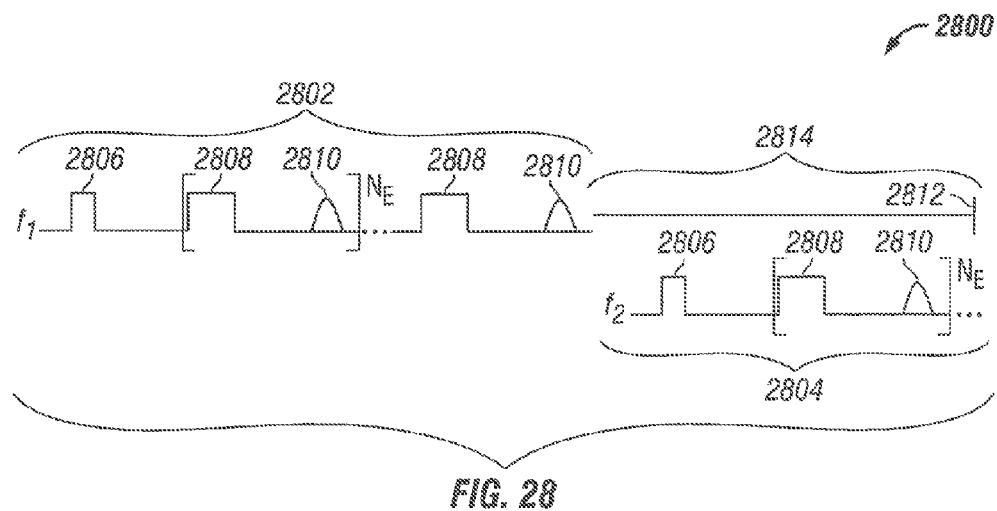
FIG. 28 shows an NQR pulse sequence with multiple pulse sequence segments in accordance with one embodiment of the present disclosure.

FIG. 28 shows an NQR pulse sequence 2800 with multiple pulse sequence segments in accordance with one embodiment of the present disclosure. The NQR pulse sequence 2800 includes at least a first pulse sequence segment 2802 and a second pulse sequence segment 2804. Each segment includes an excitation pulse 2806, a series of refocusing pulses 2808, and a series of echoes 2810. In one specific example, the sequence segments 2802, 2804 are SLSE sequences. In various other embodiments, the sequence segments are 2802, 2804 are SSFP sequences. In various other embodiments, the sequence segments are 2802, 2804 perturbation-detect sequences, as shown in for example FIG. 8. The sequence segments 2802, 2804 can also be any combination of different NQR sequences (e.g., SLSE, SSFP, and/or perturbation-detect sequences).

As shown in FIG. 28, the first segment 2802 is applied to the substance using a first set of frequencies ($f_1$) and the second segment 2804 is applied to the substance using a second set of frequencies ($f_2$). The frequency difference ($\Delta f_0$) between the two sets of frequencies or even frequencies within the same set can be as great as 10%. In various other embodiments, the frequency difference can be even greater (e.g., 20% 30% or 50%). For example, to detect glycine, the first frequency ($f_1$) is applied at 1052 kHz and the second frequency ($f_2$) is applied at 737 kHz. The difference between the two frequencies is 30%.

The term "set" of frequencies means one or more frequencies as used herein. The term "set" is used because the frequency within a segment may not be a single frequency. For example, a segment that is a perturbation-detect sequence will include a first frequency for the perturbation segment and a second different frequency for the detect segment. On the other hand, a segment that is an SLSE sequence may include only a single frequency.

In various embodiments of the present disclosure, the first segment 2802 is selected to match at least one resonant frequency of a first set of atomic nuclei and the second segment 2804 is selected to match at least one resonant frequency of a second set of atomic nuclei. In this manner, the first segment 2802 generates a first resonant signal in the first set of nuclei and the second segment 2804 generates a second resonant signal in the first set of nuclei.

In some embodiments, the first set of atomic nuclei and the second set of atomic nuclei are nuclei of the same chemical element within the same chemical species. For example, the first set of atomic nuclei are nitrogen nuclei within a first site of TNT (e.g., $f_1$=842 kHz or 751 kHz) and the second set of atomic nuclei are nitrogen nuclei within a second site of TNT (e.g., $f_2$=859 kHz or 768 kHz).

In an alternative or additional embodiment, the first set of atomic nuclei and the second set of atomic nuclei are nuclei of the different chemical elements within the same chemical species. For example, the first set of atomic nuclei are nitrogen nuclei within cocaine hydro-chloride (e.g., $f_1$=961 kHz or 806 kHz kHz) and the second set of atomic nuclei are chlorine nuclei within cocaine hydro-chloride (e.g., $f_2$=2530 kHz).

In further alternative or additional embodiment, the first set of atomic nuclei and the second set of atomic nuclei are nuclei within the different chemical species. For example, the first set of atomic nuclei are nitrogen nuclei within a first site of TNT (e.g., $f_1$=842 kHz or 751 kHz) and the second set of atomic nuclei are chlorine nuclei within cocaine hydro-chloride (e.g., $f_2$=2530 kHz).

In various embodiments, the NQR pulse sequences are applied a number of times to the sets of atomic nuclei within the substance (e.g., N=10, N=100, or N=1000) to improve the accuracy of the measurement. Conventional wisdom suggests that the atomic nuclei should reach thermal equilibrium before another pulse sequence is applied. In some cases, atomic nuclei reach thermal equilibrium after several $T_1$ time constants. Pausing measurements to wait for the atomic nuclei to reach thermal equilibrium increases overall measurement time.

Illustrative embodiments of the present disclosure initiate the second pulse sequence segment 2804 before the first set of atomic nuclei reach thermal equilibrium. In this manner, various embodiments speed up NQR measurements and improve SNR. As shown in FIG. 28, the first pulse sequence segment 2802 includes a refocusing pulse 208 and a corresponding echo 2810 that are repeated a number of times (e.g., $N_E$=10, $N_E$=100, $N_E$=1000) to form a series (e.g., train) of refocusing pulses and corresponding echoes. Once the first pulse sequence segment 2802 is complete, the first set of atomic nuclei will reach a point of thermal equilibrium 2812 during a time period 2814. Before this point of thermal equilibrium 2812, the second pulse sequence segment 2804 is initiated and applied to the second set of atomic nuclei. The term "thermal equilibrium" should be considered in the context of the NQR art. Many NQR systems do not apply a subsequent pulse sequence to a set of atomic nuclei until most (e.g., 90%) of the nuclei of interest are sufficiently recovered to thermal equilibrium. In one example, a set of nuclei reach thermal equilibrium over a time period (e.g., 2814) that is five times $T_1$. The time period begins when the prior pulse sequence (e.g., 2802) is completed. In another specific example, the time period (e.g., 2814) is less than five times $T_1$ (e.g., four times $T_1$).

In accordance with the method 200 shown in FIG. 2, the first resonant signal generated at the first set of nuclei and the second resonant signal generated at the second set of nuclei are detected. As explained with respect to FIGS. 2, 4, 5, 10, and 11, the detected signals can be used to determine the presence or absence of the chemical species within the substance (e.g., TNT or RDX).

Figure 29:
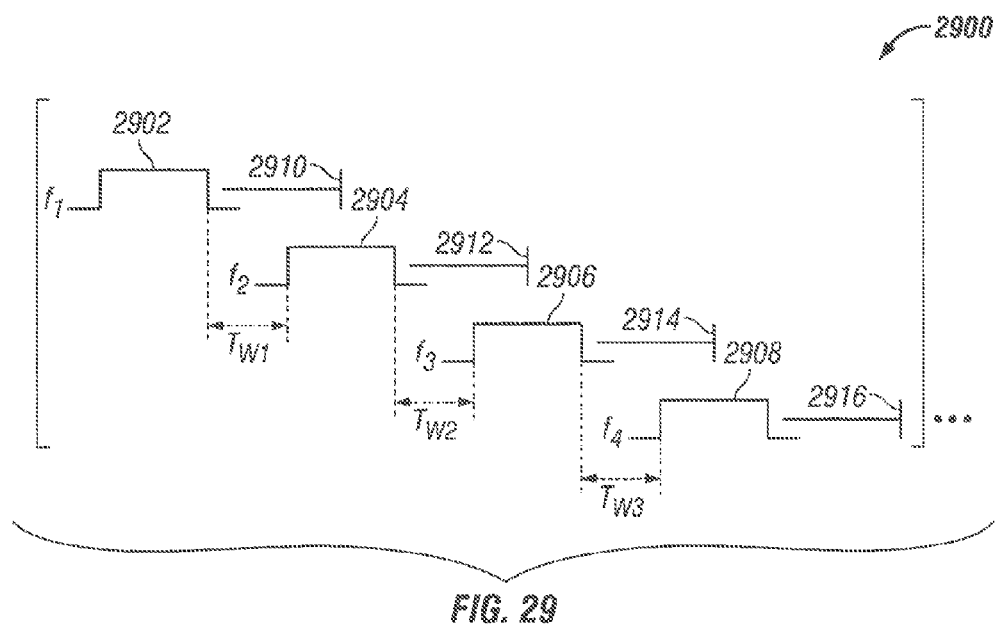
FIG. 29 shows an NQR pulse sequence with multiple pulse sequence segments in accordance with another embodiment of the present disclosure.

FIG. 29 shows an NQR pulse sequence 2900 with multiple pulse sequence segments in accordance with another embodiment of the present disclosure. In FIG. 29, the NQR pulse sequence 2900 includes four pulse sequence segments. A first segment 2902 is applied to the substance with a first set of frequencies ($f_1$), a second segment 2904 is applied to the substance with a second set of frequencies ($f_2$), a third segment 2906 is applied to the substance with a third set of frequencies ($f_3$), and a fourth segment 2908 is applied to the substance with a fourth set of frequencies ($f_4$). The frequencies of each of the four segments 2902, 2904, 2906, 2908 are selected to match a resonant frequency of four different sets of atomic nuclei.

As shown in FIG. 29, the second segment 2904 is initiated before a first set of atomic nuclei reaches a point of thermal equilibrium 2910. The third segment 2906 is initiated before the second set of nuclei reaches a point of thermal equilibrium 2912. The fourth segment 2908 is initiated before the third set of atomic nuclei reaches a point of thermal equilibrium 2914. At this point, in some embodiments, the NQR measurement stops. In various other embodiments, the NQR pulse sequence is repeated and the first segment 2902 is initiated before the fourth set of nuclei reaches a point of thermal equilibrium 2916.

Illustrative embodiments of the present disclosure are not limited to two, three, or four pulse sequence segments. Exemplary embodiments of the NQR pulse sequences may include five, six, nine, or more such pulse sequence segments. Overall time for a single repetition of a multi-segment pulse can be determined by:

$$T_{PS} = \sum_i (T_{si} + T_{wi})$$ Eq. 15 where $T_{si}$ is the total length of for the i-th segment and $T_{wi}$ is the wait time between the i-th and (i+1)-th segment, such as in for example FIG. 29. In various embodiments, this value ($T_{PS}$) is chosen to be large enough for each NQR line (e.g., different set of atomic nuclei) to have sufficient longitudinal relaxation times between repetitions of the sequence. In this manner, various embodiments can acquire signals from multiple NQR lines in a short time span, whereas conventional approaches only acquire a single line within a similar time span. The resultant speed up can be particularly significant for detection of substances with very long $T_1$ relaxation times, such as TNT, RDX, and ammonium nitrate. Various embodiments of the broadband NQR electronics advantageously enable the resultant speed up.

Figure 30:
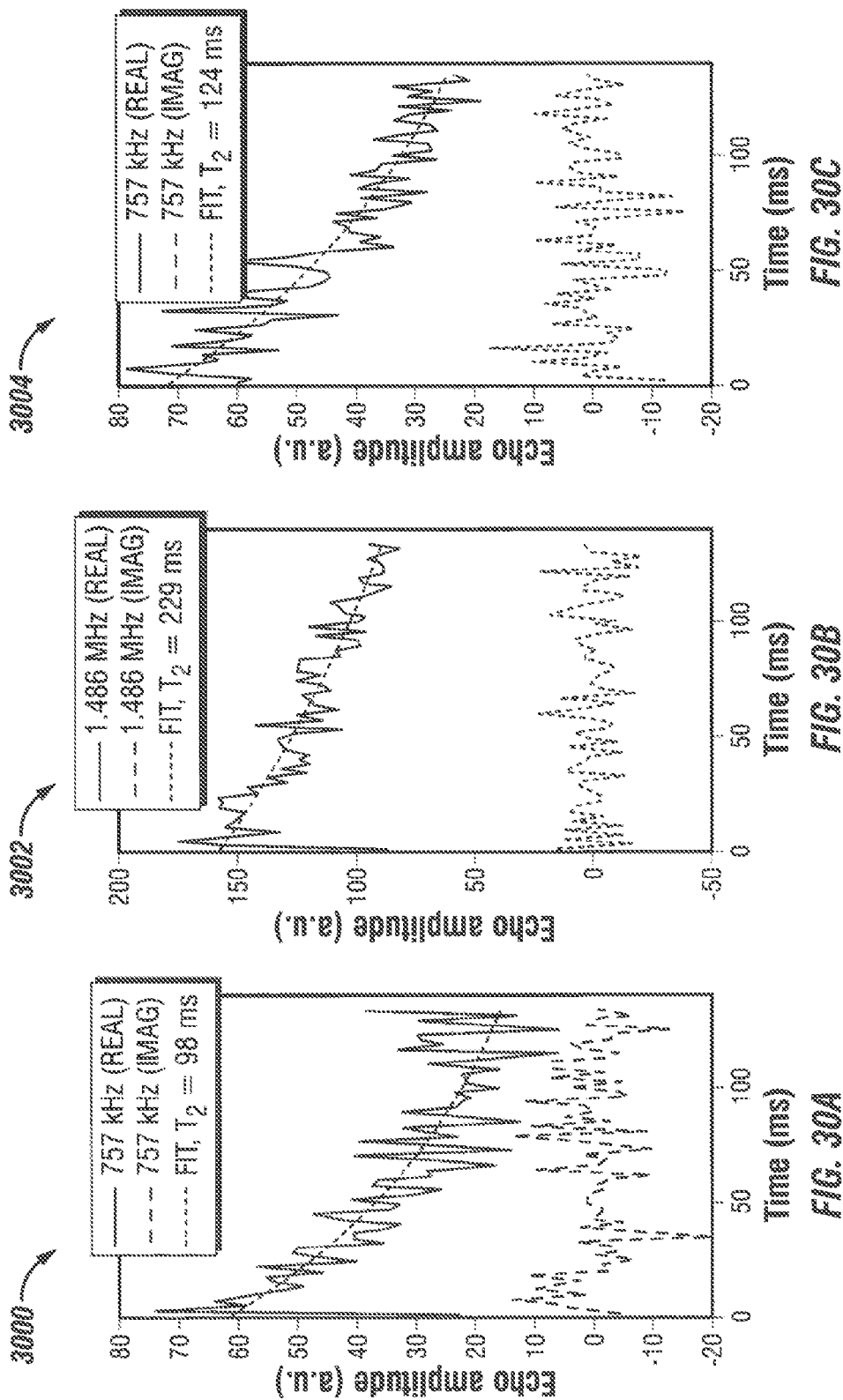
FIGS. 30A-C show echo amplitudes for a multi-segment sequence applied to sample of L-proline in accordance with some embodiment of the present disclosure.

FIGS. 30A-C shows plots 3000, 3002, 3004 of echo amplitude versus time in accordance with some embodiment of the present disclosure. In particular, the plots 3000, 3002, 3004 show the echo amplitude for a multi-segment sequence applied to L-proline. The multi-segment sequence included three segments applied at three different $^{14}N$ NQR spectral lines: 757 kHz; 1.486 MHz; and 729 kHz. Each segment was an SLSE sequence. The measurement using the multi-segment sequence sped up the measurement by a factor of three as compared to conventional approaches, which sit idle between repetitions of a sequence. The plots 3000, 3002, 3004 show that each spectral line has a different value of $T_{SLSE}$. In some embodiments, the initial amplitudes of the nuclear magnetization for the three spectral lines are seen to be approximately equal once the frequency-dependent nature of inductive detection is compensated. The sequence parameters for FIG. 30 include N=1024, $T_E$=2.1 ms, $N_E$=64, $T_p$=900, 500, 500 µs respectively ($\beta \approx 108$ degrees), and $T_W$=2 seconds.

Illustrative embodiments of the present disclosure are directed to multi-segment sequences that further improve the efficiency of NQR measurements. To this end, various embodiments apply at least two pulse sequence segments to a substance. The NQR pulse sequence segments are applied at two different frequencies and are interposed within each other. In this manner, such various interposed sequences perform measurements in parallel, whereas in many conventional systems, the measurements are performed in series.

Figure 31:
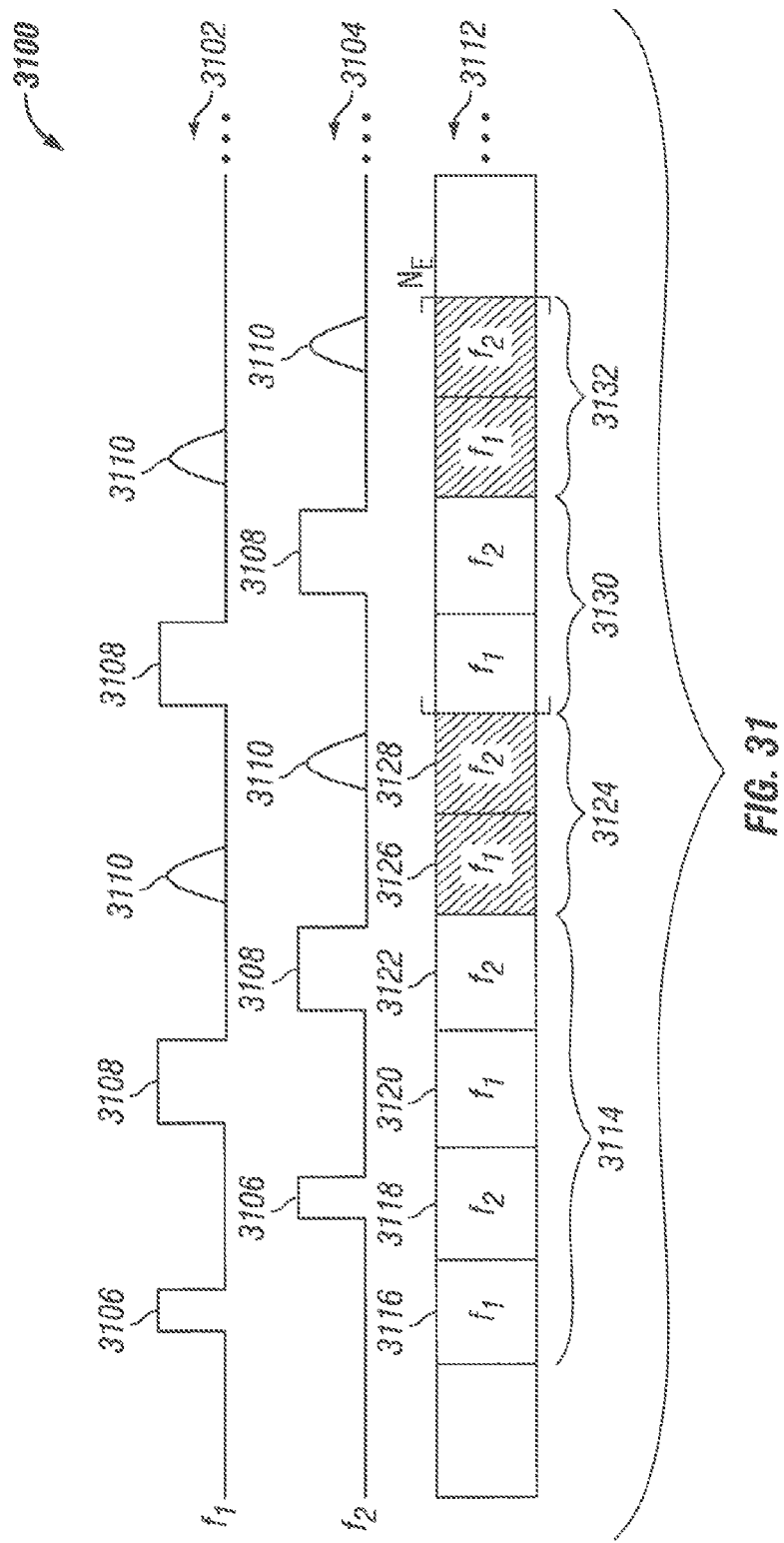
FIG. 31 shows an NQR pulse sequence with interposed pulse sequence segments in accordance with one embodiment of the present disclosure.

FIG. 31 shows an NQR pulse sequence 3100 with interposed pulse sequence segments in accordance with one embodiment of the present disclosure. The NQR pulse sequence 3100 includes at least a first pulse sequence segment 3102 and a second pulse sequence segment 3104. Each segment includes an excitation pulse 3106, a series of refocusing pulses 3108, and a series of echoes 3110. In one specific example, the sequence segments 3102, 3104 are SLSE sequences. In various other embodiments, the sequence segments are 3102, 3104 are SSFP sequences. In various other embodiments, the sequence segments are 3102, 3104 perturbation-detect sequences, as shown in for example FIG. 8. The sequence segments are 3102, 3104 can also be any combination of different NQR sequences (e.g., SLSE, SSFP and/or perturbation-detect sequences).

As shown in FIG. 31, the second segment 3104 is interposed within the first segment 3102. In other words, at least one pulse or detected echo of the second sequence segment 3104 occurs before the first pulse sequence segment 3102 is completed. The first segment 3102 is applied to the substance with a first set of frequencies ($f_1$) and the second segment 3104 is applied to the substance with a second set of frequencies ($f_2$). The frequency difference ($\Delta f_0$) between the two sets of frequencies or even frequencies within the same set can be as great as 10%. In various other embodiments, the frequency can be even greater (e.g., 20% 30% or 50%).

In various embodiments of the present disclosure, the first segment 3102 is selected to match at least one resonant frequency of a first set of atomic nuclei (e.g., a first site of nitrogen in TNT at 842 kHz) and the second segment 3104 is selected to match at least one resonant frequency of a second set of atomic nuclei (e.g., a second site of nitrogen in TNT at 768 kHz). In this manner, the first segment 3102 generates a first resonant signal in the first set of nuclei and the second segment 3104 generates a second resonant signal in the second set of nuclei.

In a specific example, the interposed pulse sequence segments are perturbation-detect sequences. In such an embodiment, the sequence segments 3102, 3104 may include four different frequencies. The first segment 3102 includes a first frequency for the perturbation segment and a second frequency for the detect segment, while the second segment 3104 includes a third frequency for the perturbation segment and a fourth frequency for the detect segment. In another example, if four such perturbation-detect sequences are applied as segments, then the entire resulting sequence may include eight different frequencies.

In accordance with the method 200 shown in FIG. 2, the first resonant signal generated at the first set of nuclei and the second resonant signal generated at the second set of nuclei are detected. As explained with respect to FIGS. 2, 4, 5, 10, and 11, the detected signals can be used to determine the presence or absence of the chemical species within the substance (e.g., TNT or RDX).

Figure 32:
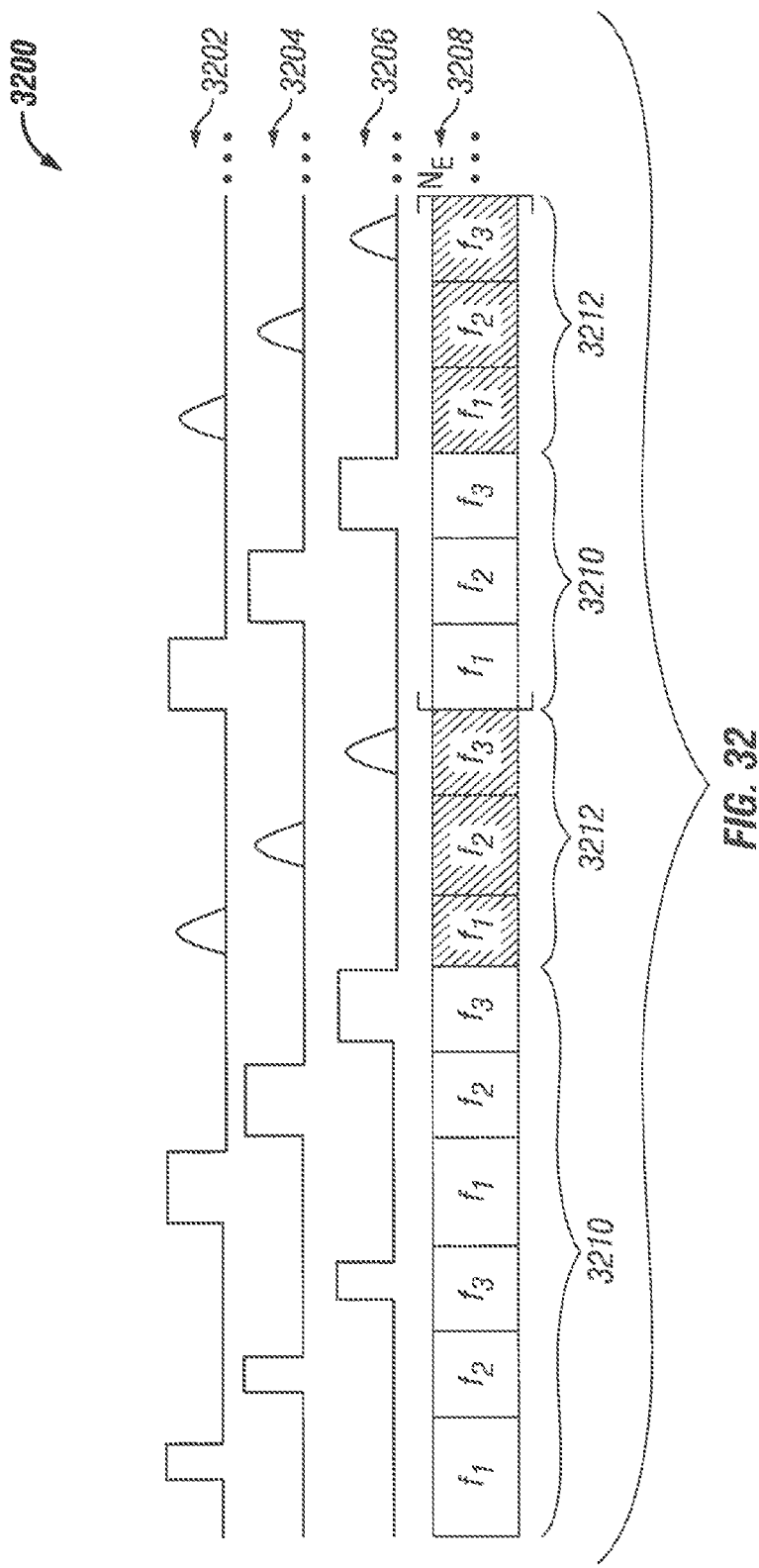
FIG. 32 shows an NQR pulse sequence with interposed pulse sequence segments in accordance with another embodiment of the present disclosure.

FIG. 32 shows an NQR pulse sequence 3200 with interposed pulse sequence segments in accordance with another embodiment of the present disclosure. In FIG. 32, the NQR pulse sequence 3200 includes three pulse sequence segments. A first segment 3202 is applied to the substance with a first set of frequencies ($f_1$), a second segment 3204 is applied to the substance with a second set of frequencies ($f_2$), and a third segment 3206 is applied to the substance with a third set of frequencies ($f_3$). Each of the second segment 3204 and the third segment 3206 are interposed within the first segment 3202. In various embodiments of the present disclosure, the first segment 3202 is selected to match a resonant frequency of a first set of atomic nuclei (e.g., a first site of nitrogen in TNT at 842 kHz), the second segment 3204 is selected to match a resonant frequency of a second set of atomic nuclei (a second site of nitrogen in TNT at 768 kHz), and the third segment 3206 is selected to match a resonant frequency of a third set of atomic nuclei (e.g., chlorine within cocaine hydro-chloride at 2530 kHz).

Illustrative embodiments of the present disclosure are not limited to two or three interposed pulse sequence segments. Exemplary embodiments may include 4, 5, 9, or more interposed pulse sequence segments.

Figure 33:
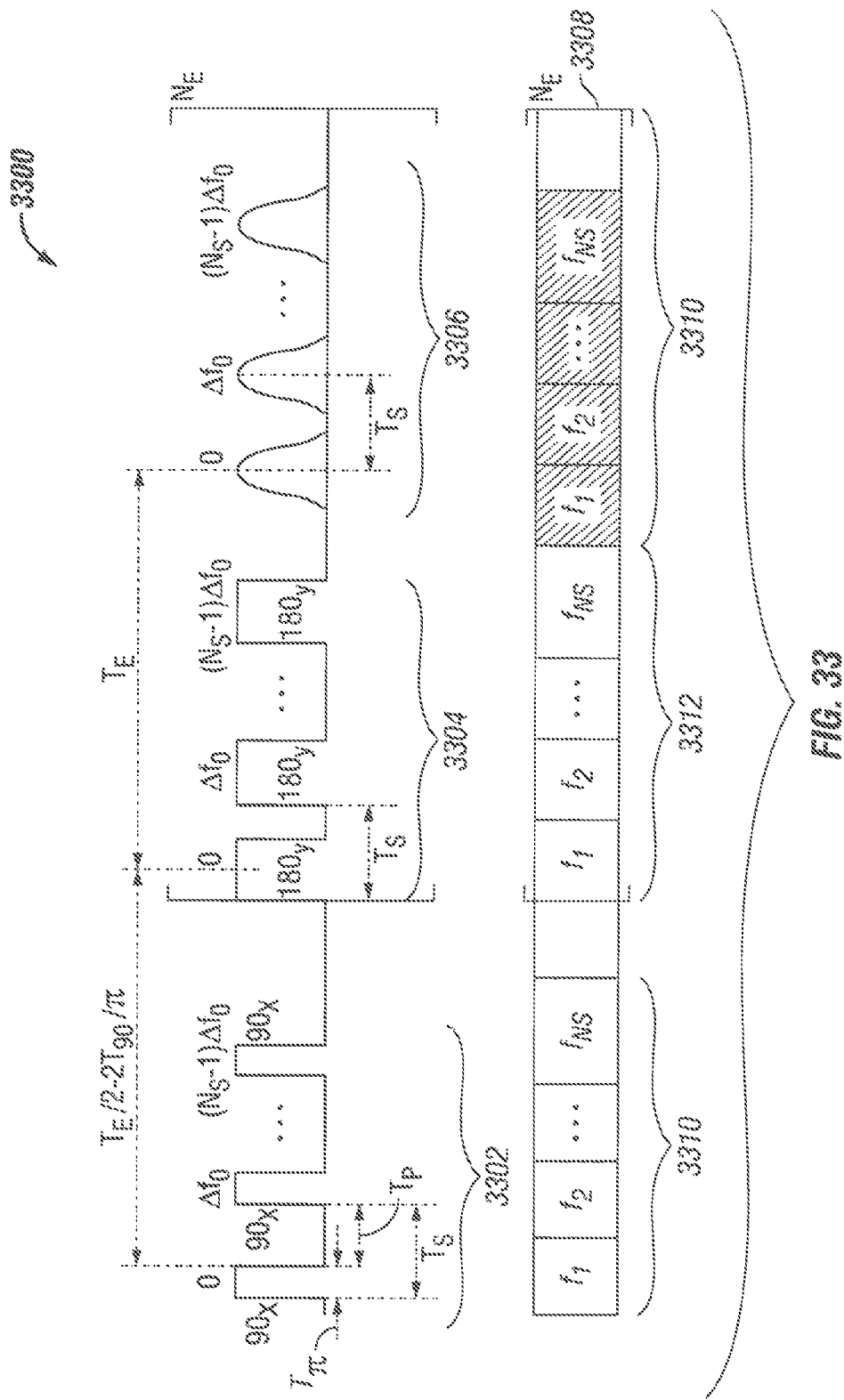
FIG. 33 shows an NQR pulse sequence with greater than two interposed pulse sequence segments in accordance with one embodiment of the present disclosure.

FIG. 33 shows an NQR pulse sequence 3300 with greater than two interposed pulse sequence segments in accordance with one embodiment of the present disclosure. The NQR pulse sequence 3300 includes a number of pulse sequence segments ($N_S$). Each segment includes an excitation pulse 3302, a series of refocusing pulses 3304, and a series of echoes 3306. Furthermore, each segment is applied at a frequency selected to match a resonant frequency of a set of atomic nuclei.

As shown in FIG. 33, echoes form sequentially in time (e.g., separated by $T_S$, where $T_S$ is the length of each refocusing interval and excitation interval). Given this phenomenon, the echoes can be distinguished from each other based upon their placement in time. In additional or alternative embodiments, the echoes can be distinguished from each other based upon their frequency content.

In various embodiments, the multi-segment sequences described herein are applied at a plurality of different frequencies. In some embodiments, the segments within each sequence are interposed. To apply the sequences and detect resonant signals, various embodiments of the present disclosure are directed to NQR electronics that are configured to switch between a transmitting mode and a receiving mode. In various embodiments, the switching of frequencies is performed according to a particular schedule.

FIG. 31 shows a switching schedule 3112 for the NQR pulse sequence 3100 in accordance with one embodiment of the present disclosure. In the specific example, the switching schedule 3112 begins with a first set of time intervals 3114. During the first set of time intervals 3114, the broadband NQR electronics are set to a transmitting mode. The first set of time intervals includes four time intervals 3116, 3118, 3120, 3122. During the first time interval 3116, the electronics generate a first frequency ($f_1$) so that the coil can apply the first excitation pulse 3106 of the first pulse sequence segment 3102. During the second time interval 3118, the electronics generate a second frequency ($f_2$) so that the coil can apply the first excitation pulse 3106 of a second pulse sequence segment 3104. During the third time interval 3118, the electronics generate the first frequency ($f_1$) so that the coil can apply the first refocusing pulse 3108 of the first pulse sequence segment 3102. During the fourth time interval 3122, the electronics generate the second frequency ($f_2$) so that the coil can apply the first refocusing pulse 3108 of the second pulse sequence segment 3104.

Following the first set of time intervals 3114, a second set of timer intervals 3124 begins. During the second set of time intervals 3124, the broadband NQR electronics switch to a receiving mode of operation. The second set 3124 includes two time intervals 3126, 2828. The first time interval 3126 is used to detect a resonant signal at the first frequency ($f_1$) generated by the first pulse sequence segment 3102 (e.g., within the first set of atomic nuclei) or absence thereof. In the embodiment shown in FIG. 31, a single echo 3110 is detected at the first frequency. The second time interval 3128 is used to detect a resonant signal at the second frequency ($f_2$) generated by the second pulse sequence segment 3104 (e.g., within the second set of atomic nuclei) or absence thereof. Again, in this example, a single echo 3110 is detected at the second frequency.

Next, a third set of time intervals 3130 follows. During the third set of time intervals 3130, the broadband NQR electronics are switched back to a transmitting mode of operation. During this set of time intervals 3130, one more refocusing pulse 3108 is applied at each of the two different frequencies (e.g., $f_1$ and $f_2$). Then, a fourth set of time intervals 3132 follows. During the fourth set of time intervals 3132, the broadband NQR electronics are switched to a receiving mode of operation. During the fourth set of time intervals 3132, resonant signals (e.g., echoes) 3110 are detected at each of the two different frequencies (e.g., $f_1$ and $f_2$). The third and fourth sets of time intervals 3130, 3132 can be repeated a plurality of times (e.g., N=10, N=100, and N=1000). In some embodiments, the time intervals have equal lengths across the switching schedule. In other embodiments, the time intervals have varying lengths. In various embodiments, the time intervals are at least as long as the excitation pulse and/or refocusing pulse that they are dedicated to applying. Also, the time intervals are at least as long as the echoes that they are dedicated to detecting. In further embodiments, the length of the time intervals is no greater than 5 ms. In yet further embodiments, the length of the time intervals is no greater than 100 ms.

FIGS. 32 and 33 show two switching schedules 3208, 3308 for NQR pulse sequences, 3200, 3300 in accordance with embodiments of the present disclosure. In FIG. 32, the switching schedule 3208 also modulates between a transmitting mode 3210 and a receiving mode 3212. In this case, in a transmitting mode, the broadband NQR electronics apply three different frequencies (e.g., $f_1$, $f_2$, and $f_3$). Similarly, in FIG. 33, the switching schedule 3308 also modulates between a transmitting mode 3310 and a receiving mode 3312 and, within the transmitting mode, the broadband NQR electronics apply $N_S$ number of different frequencies (e.g., $f_1$, $f_2$, $f_3$, . . . $f_{Ns}$). In this manner, various embodiments of the present disclosure apply pulse sequence segments at various different frequencies and detect resonant signals from a plurality of different sets of atomic nuclei.

Illustrative embodiments of the present disclosure use broadband NQR electronics to apply multi-segment sequences at different frequencies and/or to detect resonant signals at different frequencies. Further details of multi-segment and interposed sequences are described in U.S. patent application Ser. No. 13/774,457, entitled "Method and System for Applying NMR Pulse Sequences Using Different Frequencies" and filed on Feb. 22, 2013, which application is incorporated herein, in its entirety, by reference.

Figure 34:
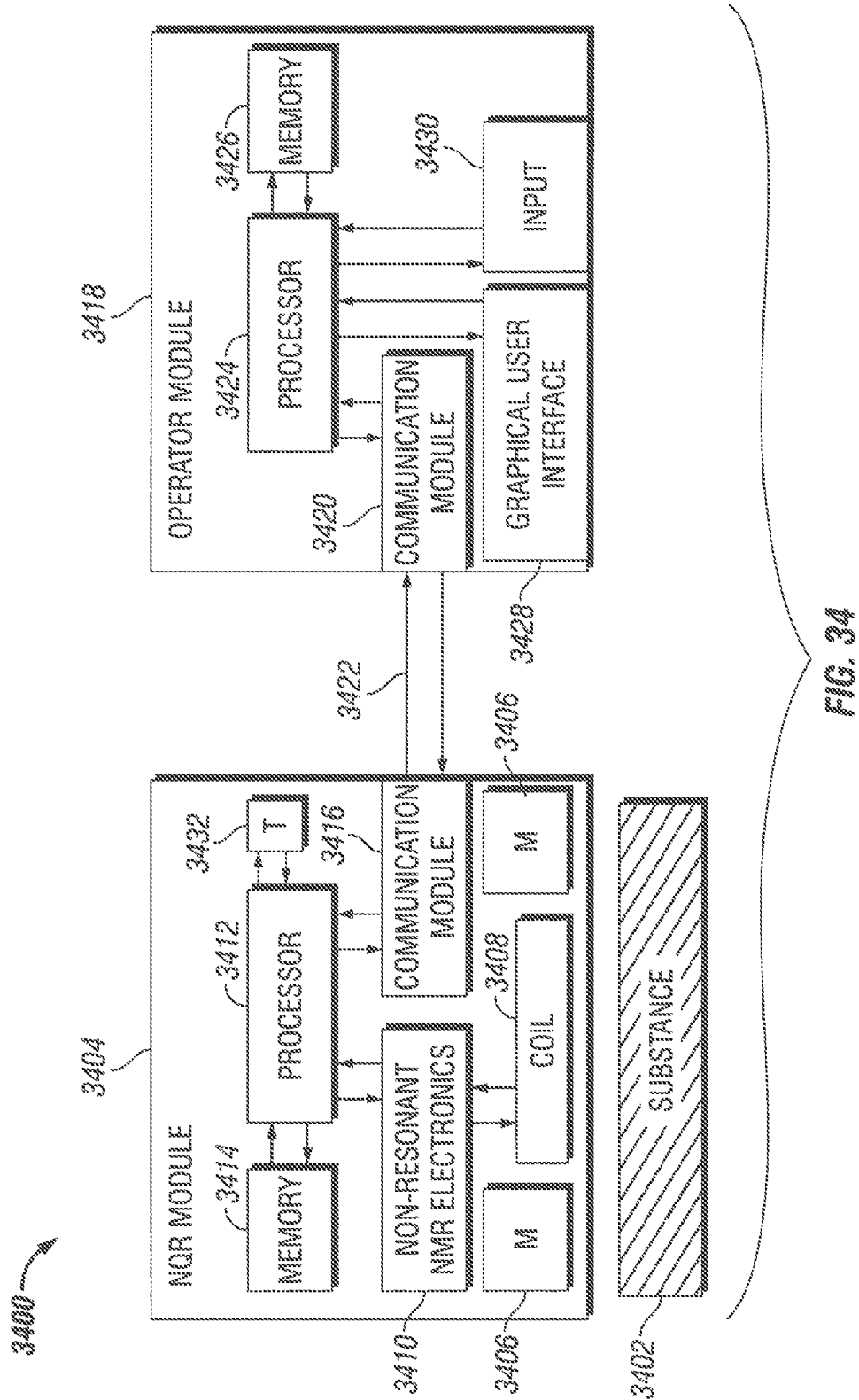
FIG. 34 shows a broadband NQR system for applying NQR sequences to a substance in accordance with one embodiment of the present disclosure.

FIG. 34 shows a broadband NQR system 3400 for applying NQR sequences to a substance 3402 in accordance with one embodiment of the present disclosure. Such an NQR system can be used as part of an explosive detection system, a drug detection system, or a borehole logging system. The system 3400 includes an NQR module 3404.

In various embodiments, the NQR module 3404 includes an electro-magnetic device 3406 for applying a static magnetic field to the substance 3402. In some embodiments, the electro-magnetic device 3406 is a magnet or an array of magnets. The magnets can be formed from a samarium-cobalt magnetic material. In other embodiments, no electromagnetic device 3406 is provided for applying a static magnetic field.

The NQR module 3404 also includes at least one coil (e.g., antenna) 3408 and broadband NQR electronics 3410 electronically coupled to the coil. The coil 3408 and broadband NQR electronics 3410 apply an oscillating field to the substance 3402 (e.g., a radio frequency (RF) field). In accordance with exemplary embodiments of the present disclosure, the oscillating field applied to the substance can include any of the NQR sequences described herein (e.g., a multi-segment sequence, an interposed segment sequence, SLSE sequence, and/or perturbation-detect sequence). The coil 3408 and broadband NQR electronics 3410 are also used to detect resonant signals that originate within the substance 3402. In the embodiment shown in FIG. 34, the substance of interest 3402 is positioned outside of the coil 3408. In additional or alternative embodiments, the substance 3402 can also be positioned within the coil 3408.

The broadband NQR electronics 3410 are electronically coupled to a processor 3412 and a memory 3414 (e.g., a computer system). The memory 3414 can be used to store computer instructions (e.g., computer program code) that are interpreted and performed by the processor 3412. The memory 3414 may be a digital memory such as a random-access memory, a flash drive, a hard drive, or a disc drive.

In alternative or additional embodiments, the NQR sequences described herein may be implemented as a series of computer instructions fixed either on a tangible medium, such as a computer readable medium (e.g., a diskette, CD-ROM, ROM, field-programmable array (FPGA) or fixed disk) or transmittable to a computer system, via a modem or other interface device, such as a communications adapter connected to a network over a tangible medium (e.g., optical or analog communications lines). The series of computer instructions can embody all or part of the NQR sequences described herein.

The NQR sequences described herein and various other NQR pulse sequences may be stored within the memory 3414 as software or firmware. The processor 3412 may be configured to retrieve the sequences from memory 3414 and provide instructions to the broadband NQR electronics 3410 to apply the sequences to the substance 3402. The detected resonant signals may also be communicated from the broadband electronics 3410 to the processor 3412 for storage on the memory 3414.

The NQR module 3404 may also include a temperature sensor 3432 coupled with the processor 3412 so that the NQR system 3400 can correctly determine resonant frequencies of atomic nuclei in an environment with dynamic temperatures. Many NQR transition frequencies depend upon temperature.

The processor 3412 is also electronically coupled to a communications module 3416. The communications module 3416 communicates with an operator module 3418. The operator module 3418 also includes a communications module 3420 so that the operator module 3418 can communicate with the NQR module 3404. A communications link 3422 between the operator module 3418 and the NQR module 3404 can be established using, for example, a hard-wired link, an optical link, acoustic link, and/or a wireless link. The operator module 3418 includes a processor 3424 and a memory 3426 (e.g., a computer system). The processor 3424 and memory 3426 support a graphical user interface (GUI) 3428, such as a monitor, a touch screen, a mouse, a keyboard, and/or a joystick. The GUI 3428 allows an operator to control and communicate with the NQR module 3404. The processor 3424 is also electronically coupled to one or more information input devices 3430. In some embodiments, the input device 3430 is a port for communicating with a removable medium (e.g., a diskette, CD-ROM, ROM, USB, and/or fixed disk). In additional or alternative embodiments, the input device 3430 is a modem and/or other interface device that is in communication with a computer network (e.g., Internet and/or LAN).

In various embodiments, the NQR module 3404 and the operator module 3418 can be used to perform functions selected from the following non-limiting list:

Communicate instructions to the NQR module 3404 to initiate and/or terminate NQR measurements;

Communicate instructions to change parameters of NQR sequences to the NQR module 3404 (e.g., pulse amplitude of sequences, pulse lengths, timing between pulses, shape of pulses, and/or frequency of pulses);

Communicate detected resonant signal data from the NQR module 3404 to the operator module 3418;

Communicate NQR pulse sequences from the operator module 3418 to the NQR module 3404;

Perform analysis of detected resonant signal data to determine NQR properties of substances at the operator module 3418 and/or the NQR module 3404;

Display various plots of NQR properties to the operator at the operator module 3418; and Download NQR pulse sequences from the operator module 3418 to the NQR module 3404.

Illustrative embodiments of the present disclosure are not limited to the system shown 3400 in FIG. 34. Various modifications can be made to the system 3400. For example, in one specific embodiment, the NQR module 3404 lacks the processor 3412 and the memory 3414. In such an embodiment, the processor 3424 and memory 3426 on the operator side 3418 support the broadband NQR electronics 3410. Furthermore, in some embodiments, the NQR module 3404 and the operator module 3418 can be physically located in two separate locations. For example, in a borehole application, the NQR module 3404 can be located downhole, while the operator module 3418 is located at the surface. In various other embodiments, the NQR module 3404 and the operator module 3418 can be physically located in the same place as a single system. This may be the case when the system is used in a surface environment, such as a building or laboratory (e.g., a bomb detection system or a drug detection system). Furthermore, in various embodiments, the NQR system 3400 can operate between an NQR mode and a NMR mode. In other words, the NQR system can apply both NQR pulse sequences and NMR pulse sequences to a substance of interest.

Various embodiments of the present disclosure have application in non-invasive detection of chemical species. In various embodiments, the NQR system and NQR sequences described herein (e.g., a multi-segment sequence, an interposed segment sequence, SLSE sequence, and/or perturbation-detect sequence) can be used for detection of explosives, such as ammonium nitrate, TNT, and/or RDX. In one example, the NQR system is used to detect explosives concealed in luggage at airports or border crossings. In another example, the NQR system is used to detect landmines in a battlefield environment. In further embodiments, the NQR system and NQR sequences described herein can be used for detection of illegal drug detection, such as heroin hydro-chloride and/or cocaine hydro-chloride. It can also be used for detecting counterfeit or adulterated versions of legal drugs, such as metformin and paracetamol, as described above with reference to FIG. 17.

Illustrative embodiments of the present disclosure are also directed to oil and gas field applications. For example, in one specific example, the NQR system and NQR sequences described herein can be used to detect and determine the composition of kerogen. Kerogen contains nitrogen which can be detected according to the illustrative embodiments described herein. Kerogen is a solid mixture of organic chemical compounds that make up a portion of the organic matter in sedimentary rocks. Oil shale, an organic-rich fine-grained sedimentary rock, contains significant amounts of kerogen, from which liquid hydrocarbons called shale oil can be produced. Kerogen is a mixture of organic materials, rather than a specific chemical, and therefore does not have a unique chemical formula. The chemical composition of kerogen can vary distinctively from sample to sample. As an example, kerogen from the Green River Formation oil shale deposit of western North America contains elements in the following proportions: carbon 215:hydrogen 330:oxygen 12:nitrogen 5:sulfur 1. Thus, the fraction of nitrogen by weight is 5/563=0.89% in this case. However, analysis of a variety of other kerogen samples shows that this fraction can vary between 0.8% and 2%. Oil shale contains a lower percentage of organic matter than coal. In commercial grades of oil shale, the ratio of organic matter to mineral matter lies approximately between 0.75:5 and 1.5:5 (13% and 23%). Thus, the fraction of nitrogen in oil shale ranges from 0.12% to 0.46% (approximately 1 in 800 to 1 in 200). The resultant NQR resonant frequencies for shales can be determined by identifying where so-called "quadrupole dips" occur in measurements of biological samples using field cycling NMR spectrometers. A quadrupole dip is a reduction in proton $T_1$ relaxation time (e.g., 10%-15% reduction) due to cross-relaxation between protons and adjacent nitrogen atoms in proteins and amino acids. These dips can be centered at 650 kHz, 2.1 MHz, and 2.75 MHz. Further exemplary embodiments of oil and gas field applications are described below.

Figure 35:
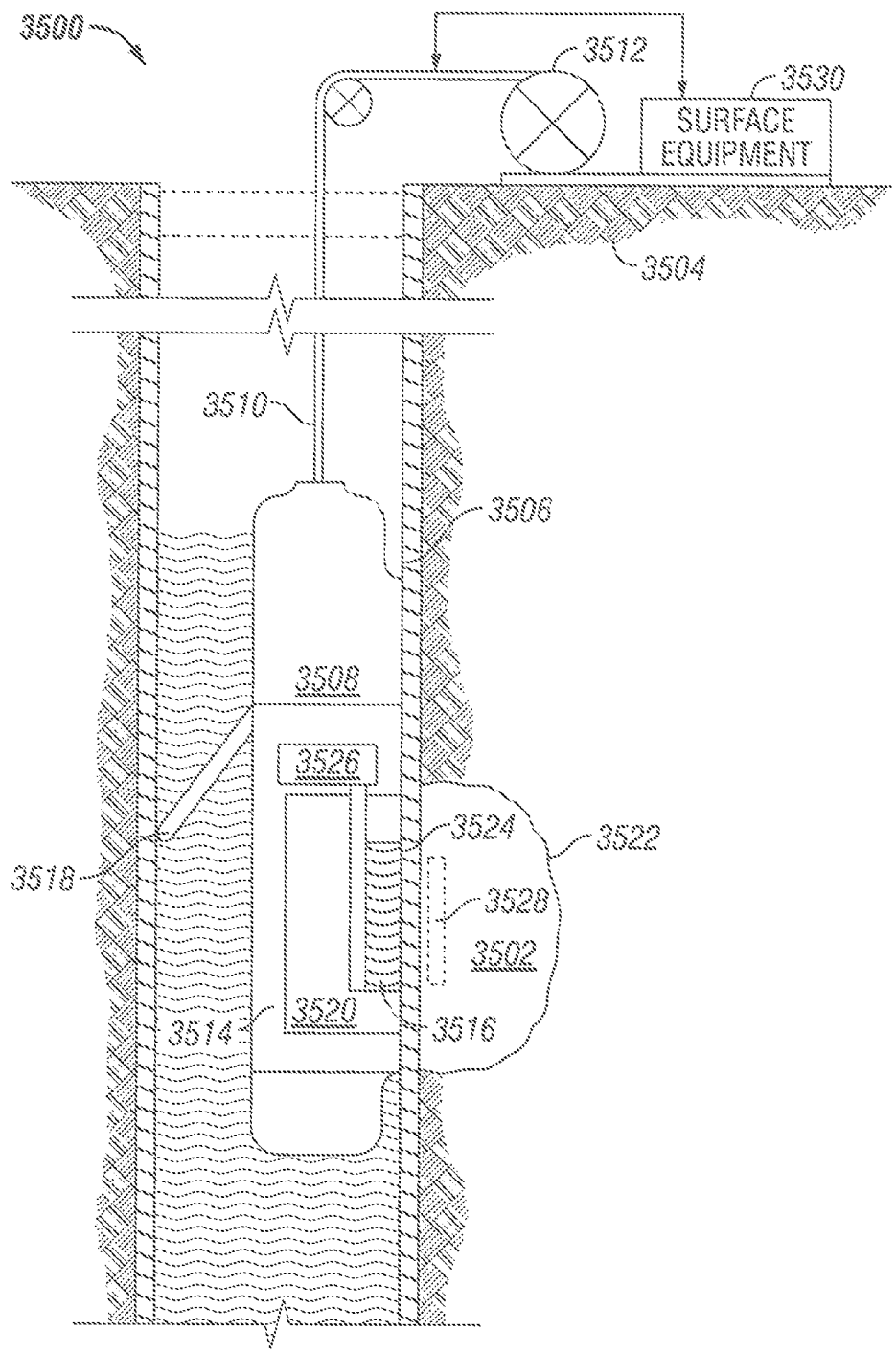
FIG. 35 shows a wireline system for applying NQR sequences to a substance in accordance with one embodiment of the present disclosure.

FIG. 35 shows a wireline system 3500 for applying NQR sequences to a substance 3502 in accordance with one embodiment of the present disclosure. The wireline system 3500 is used to investigate, in situ, a substance 3502 within an earth formation 3504 surrounding a borehole 3506 to determine a characteristic of the substance (e.g., characteristics of solids and liquids within the earth formation). As shown in FIG. 35, a wireline tool 3508 is disposed within the borehole 3506 and suspended on an armored cable 3510. A length of the cable 3510 determines the depth of the wireline tool 3508 within the borehole 3506. The length of cable is controlled by a mechanism at the surface, such as a drum and winch system 3512. Although the wireline tool 3508 is shown as a single body in FIG. 35, the tool may alternatively include separate bodies.

As shown in FIG. 35, the wireline tool 3508 includes an NQR logging module 3514 that can used to apply any of the NQR sequences described herein (e.g., a multi-segment sequence, an interposed segment sequence, SLSE sequence, and/or perturbation-detect sequence). The NQR logging module 3514 includes a face 3516 that is shaped to contact the borehole wall 3506 with minimal gaps or standoff. In some embodiments, a retractable arm 3518 is used to press the body of the wireline tool 3508 and the face 3516 against the borehole wall 3506. In some embodiments, the NQR logging module 3514 also includes an electro-magnetic device 3520 for applying a static magnetic field to a sensitivity zone 3522 within the earth formation 1004. As explained above, in some embodiments, the electro-magnetic device 3520 is a magnet or an array of magnets formed from a magnetic material. In other embodiments, the logging module 3514 lacks the electro-magnetic device 3520.

The NQR logging module 3514 also includes at least one coil 3524 and broadband NQR electronics 3526 electronically coupled to the coil. The coil 3516 and broadband NQR electronics 3526 apply an oscillating field to an area of interest 3528 within the earth formation 3504. The area of interest 3502 is located within the sensitivity zone 3522 of the electro-magnetic device 3520. In accordance with exemplary embodiments of the present disclosure, the oscillating field applied to the earth formation 3504 includes any of the NQR sequences described herein (e.g., a multi-segment sequence, an interposed segment sequence, SLSE sequence, and/or perturbation-detect sequence). The static magnetic field and oscillating field generate resonant signals within the area of interest 3528. These resonant signals are detected by the coil 3524. The detected resonant signals are used to determine characteristics of the substance 3502 within the area of interest 3528.

The wireline system 3500 includes surface equipment 3530 for supporting the wireline tool 3508 within the borehole 3506. In various embodiments, the surface equipment 3530 includes a power supply for providing electrical power to the wireline tool 3508. The surface equipment 3530 also includes an operator interface for communicating with the NQR logging module 3514. Such an operator interface has already been described with reference to FIG. 34. In some embodiments, the NQR logging module 3514 and operator module communicate through the armored cable 3510.

Figure 36:
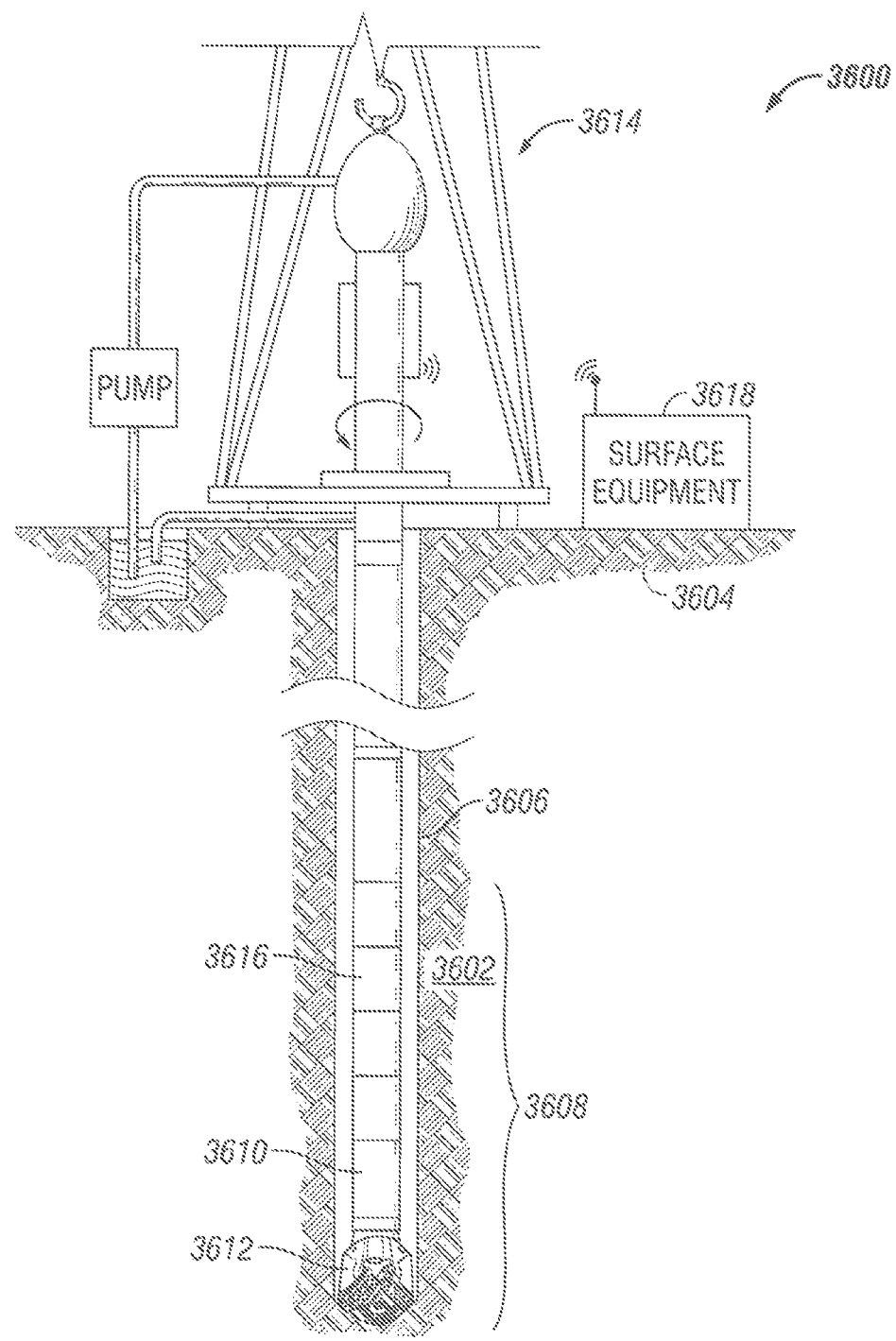
FIG. 36 shows a LWD system for applying multi-segment sequences to a substance in accordance with one embodiment of the present disclosure.

Illustrative embodiments of the present disclosure can also be applied in logging-while-drilling (LWD) systems. FIG. 36 shows a LWD system 3600 for applying NQR sequences to a substance in accordance with one embodiment of the present disclosure. The LWD system 3600 can be used to investigate, in situ, a substance 3602 within an earth formation 3604 surrounding a borehole 3606 to determine a characteristic of the substance, while a drilling operation is performed. The LWD system 3600 includes a drill string 3608 that is suspended within the borehole. The drill string 3608 includes a drill collar 3610 with a drill bit 3612 disposed at the lower-end of the drill collar. The LWD system 3600 also includes a surface system with a derrick assembly and platform assembly 3614 positioned over the borehole 3606. The derrick assembly 3614 rotates the drill string 3608 and, as the drill string rotates, the drill bit 3612 drills deeper into the borehole 3606. An LWD NQR logging module 3616 is disposed within the drill collar 3610 so that the module can log the surrounding earth formation as the drilling operation is performed. The logging module 3616 communicates with surface equipment 3618, which includes an operator interface for communicating with the module. Such an operator interface has already been described with reference to FIG. 34. In various embodiments, the NQR logging module 3616 and operator module can communicate via any one of a wired-drill pipe connection, an acoustic telemetry connection, optical communication and/or electronic communication.

Figure 37:
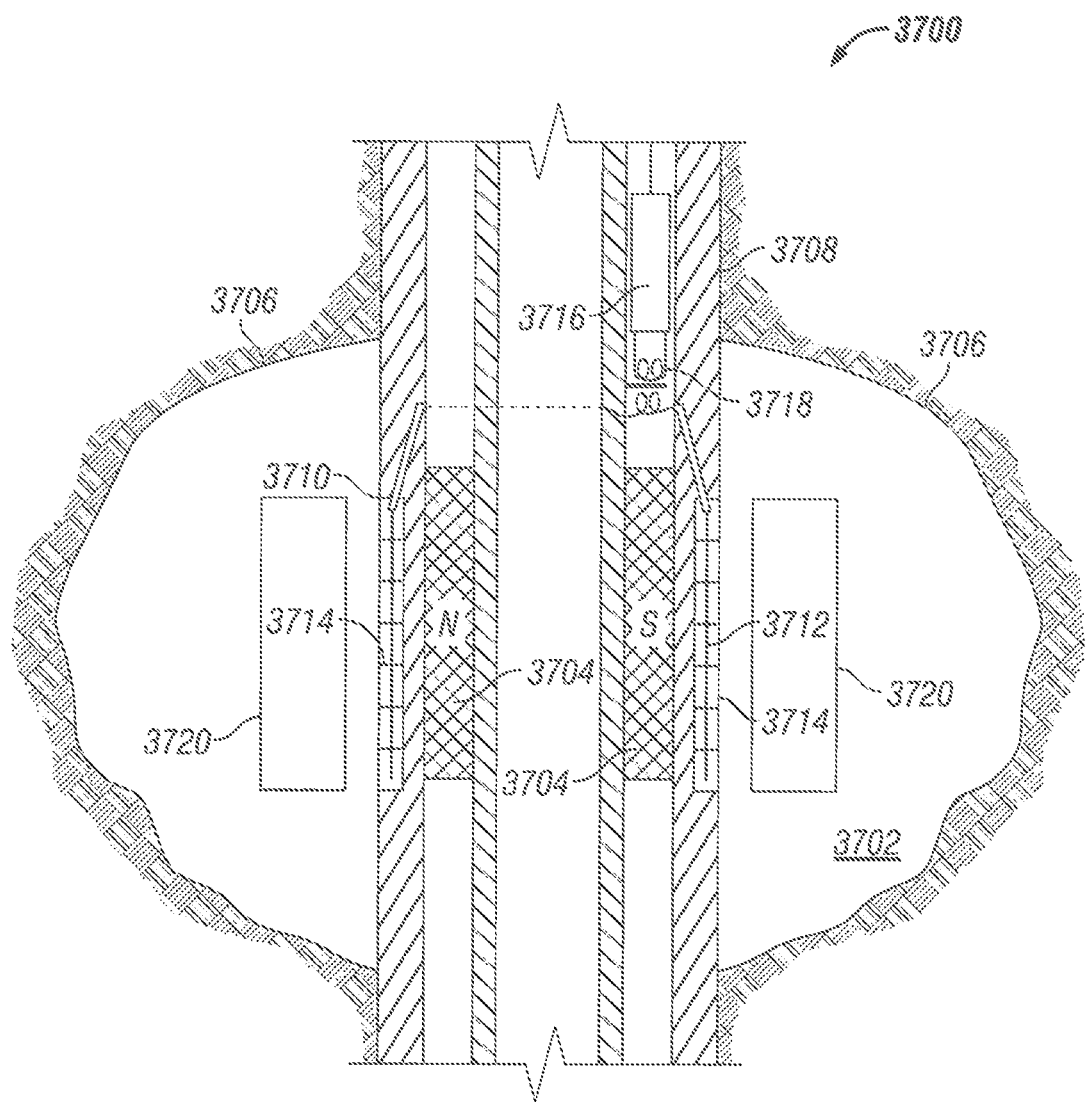
FIG. 37 shows an LWD NQR logging module for applying NQR sequences to a substance in accordance with one embodiment of the present disclosure.

FIG. 37 shows an LWD NQR logging module 3700 for applying NQR sequences to a substance 3702 in accordance with one embodiment of the present disclosure. In some embodiments, the module 3700 includes a cylindrical magnet 3704 that generates a static magnetic field within a zone of sensitivity 3706 within the earth formation. The module 3700 also includes a drill collar 3708 with an axial slot 3710.

A coil 3712 is disposed within the slot 3710 and the slot is filled with a ceramic insulator. The slot 3712 is sealed using a cover 3714. In some embodiments, the cover 3714 is formed from a non-magnetic material. The coil 3712 is composed of at least two diametrically opposed conductors. At one end, the conductors are grounded to the drill collar 3708. At the other end, the conductors are coupled to broadband NQR electronics 3716. The broadband NQR electronics 3716 include a transformer and the conductors are couple to the transformer via, for example, pressure feed-throughs. In one specific example, the transformer 3718 maintains a 180 degree phase difference between the currents in the diametrically opposite conductors. The coil 3712 applies an oscillating magnetic field to an area of interest 3720 within the zone of sensitivity 3706. In some embodiments, the oscillating magnetic field is axially symmetric to facilitate measurements during rotation of the drill string. In accordance with exemplary embodiments of the present disclosure, the oscillating field applied to the earth formation includes any of the NQR sequences described herein (e.g., a multi-segment sequence, an interposed segment sequence, SLSE sequence, and/or perturbation-detect sequence). In additional or alternative embodiments, the coil 3712 can also be configured so that the drill collar itself 3708 produces the oscillating magnetic field.

Although several example embodiments have been described in detail above, those skilled in the art will readily appreciate that many modifications are possible in the example embodiments without materially departing from the scope of this disclosure. Accordingly, all such modifications are intended to be included within the scope of this disclosure.

We claim:

1. A method for determining presence of a chemical species within a substance using nuclear quadrupole resonance (NQR), the method comprising:
    applying a first NQR pulse sequence to the substance using broadband electronics having a non-resonant transmitter circuit;
    detecting a first NQR signal within the substance corresponding to said first NQR pulse sequence;
    applying a plurality of NQR pulse sequences at a plurality of frequencies to the substance using said broadband electronics having said non-resonant transmitter circuit without adjusting said broadband electronics;
    detecting a plurality of NQR signals within the substance corresponding to said plurality of NQR pulse sequences at said plurality of frequencies; and
    determining presence of a chemical species within the substance using the first NQR signal and said plurality of NQR signals.

2. The method according to claim 1, wherein the first NQR pulse sequence is applied at a first set of frequencies selected to match at least one known NQR frequency of a first set of atomic nuclei within the chemical species and the first NQR pulse sequence generates the first NQR signal.

3. The method according to claim 2, wherein the first set of frequencies comprises a first frequency selected to match a first known NQR frequency of the first set of atomic nuclei within the chemical species and
    the second NQR pulse sequence includes:
        at least one pulse at the first frequency; and
        a pulse sequence segment at a second frequency selected to match a second known NQR frequency of the first set of atomic nuclei within the chemical species, wherein the second pulse sequence segment generates a second NQR signal within the substance.

4. The method of claim 3, wherein said determining the presence of the chemical species within the substance is determined by comparing the first NQR signal and the second NQR signal.

5. The method according to claim 4, wherein an amplitude of the first NQR signal and an amplitude of the second NQR signal are compared to determine the presence of the chemical species within the substance.

6. The method according to claim 2, further comprising:
    applying a third NQR pulse sequence to the substance using said broadband electronics having the non-resonant transmitter circuit without adjusting said broadband electronics, wherein the third NQR pulse sequence is applied at a third set of frequencies selected to match at least one known NQR frequency of a second set of atomic nuclei within the chemical species and the third NQR pulse sequence generates a third NQR signal; and
    detecting the third NQR signal.

7. The method of claim 6, wherein the presence of the chemical species within the substance is determined using the first NQR signal and the third NQR signal.

8. The method of claim 7, wherein the first set of atomic nuclei and the second set of atomic nuclei are different chemical elements.

9. The method of claim 7, wherein the first set of atomic nuclei and the second set of atomic nuclei are the same chemical elements located at different sites within the chemical species.

10. The method according to claim 1, wherein the chemical species is a chemical compound.

11. The method according to claim 2, wherein the first set of atomic nuclei is selected from the group consisting of: nitrogen, chlorine and copper.

12. The method according to claim 2, wherein the first set of atomic nuclei is nitrogen and the chemical species is selected from the group consisting of: Glycine, Ammonium Nitrate, TNT, RDX, Cocaine Hydrochloride, and Heroin Hydrochloride.

13. The method according to claim 7, wherein the first set of atomic nuclei is nitrogen, the second set of atomic nuclei is chlorine, and the chemical species is selected from the group consisting of: Cocaine Hydrochloride and Heroin Hydrochloride.

14. The method according to claim 6, wherein the third NQR pulse sequence is applied before the first set of atomic nuclei reach thermal equilibrium.

15. The method according to claim 14, wherein the third NQR pulse sequence is interposed within the first NQR pulse sequence.

16. The method according to claim 2, further comprising:
    applying a plurality NQR pulse sequences at frequencies selected to match known NQR frequencies of a plurality of different atomic nuclei within the chemical species;
    using a plurality of NQR signals from each of the plurality of different atomic nuclei to determine the presence of the chemical species.

17. A method for applying a nuclear quadrupole resonance (NQR) sequence to a substance, the method comprising:
    applying an NQR pulse sequence to the substance using broadband electronics having a non-resonant transmitter circuit, the NQR pulse sequence comprising:
        a first pulse sequence segment at a first frequency selected to match a first known NQR frequency of a first set of atomic nuclei; and a second pulse sequence segment at a second frequency selected to match a second known NQR frequency of a second set of atomic nuclei, wherein the second pulse sequence segment is initiated before the first set of atomic nuclei reach thermal equilibrium, with said first pulse sequence and said second pulse sequence being applied without adjusting said broadband electronics.

18. The method according to claim 17, wherein the second pulse sequence segment is at least partially interposed within the first pulse sequence segment.

19. The method according to claim 17, wherein the NQR pulse sequence includes at least three pulse sequence segments that are applied at different frequencies and configured to generate NQR signals in three different sets of atomic nuclei and at least two of the pulse sequence segments are at least partially interposed within the first pulse sequence segment.

20. A system comprising:
a coil for applying a nuclear magnetic resonance (NQR) pulse sequences to a substance;
a NQR transmitter comprising a broadband electronics circuit including a non-resonant NQR transmitter circuit electronically coupled to the coil; and
a processor;
a memory storing instructions executable by the processor to perform processes that include providing NQR pulse sequences to the NQR transmitter without adjusting said broadband electronics, wherein the NQR pulse sequences comprise a first NQR pulse sequence comprising a first frequency selected to match a known NQR frequency of a first set of atomic nuclei within the chemical species, and
a second NQR pulse sequence comprising a second frequency selected to match a known NQR frequency of a second set of atomic nuclei within the chemical species.

21. The system according to claim 20, further comprising:
a NQR receiver that is configured to receive NQR signals generated within the substance and detected at the coil.

22. The system according to claim 21, wherein the processes further include determining presence of a chemical species within the substance using the NQR signals.

23. The system according to claim 20, wherein the processes further include determining the presence of a chemical species within the substance using the NQR signals generated by the first NQR pulse sequence and the second NQR pulse sequence.

24. The system according to claim 20, wherein the first NQR pulse sequence and the second NQR pulse sequence are interposed.

25. The system according to claim 22, wherein the NQR pulse sequences comprise:
a first NQR pulse sequence comprising a first frequency selected to match a first known NQR frequency of a first set of atomic nuclei within the chemical species; and
a second NQR pulse sequence that includes:
at least one pulse comprising the first frequency; and
a pulse sequence segment comprising a second frequency selected to match a second known NQR frequency of the set of atomic nuclei within the chemical species.

26. The system according to claim 25, wherein the processes further include determining the presence of a chemical species within the substance by comparing the NQR signals generated by the first NQR pulse sequence and the second NQR pulse sequence.

27. The system of claim 20, wherein the system is part of a borehole tool for investigating earth formations.

* * * * *